United States Patent
Eichenberger et al.

(10) Patent No.: US 8,691,002 B2
(45) Date of Patent: Apr. 8, 2014

(54) ORGANIC BLACK PIGMENTS AND THEIR PREPARATION

(75) Inventors: Thomas Eichenberger, Basel (CH); Thomas Ruch, Delémont (CH); Ralf Bauer, Rickenbach-Egg (DE); Christoph Krebs, Prattein (CH); Ursula Luterbacher, Reinach (CH); Marc Maurer, Village-Neuf (FR)

(73) Assignee: BASF SE, Ludwigshafen (DE)

( * ) Notice: Subject to any disclaimer, the term of this patent is extended or adjusted under 35 U.S.C. 154(b) by 264 days.

(21) Appl. No.: 13/144,940

(22) PCT Filed: Dec. 28, 2009

(86) PCT No.: PCT/EP2009/067953
§ 371 (c)(1),
(2), (4) Date: Aug. 17, 2011

(87) PCT Pub. No.: WO2010/081625
PCT Pub. Date: Jul. 22, 2010

(65) Prior Publication Data
US 2011/0294385 A1 Dec. 1, 2011

(30) Foreign Application Priority Data

Jan. 19, 2009 (EP) .................................... 09150817

(51) Int. Cl.
C09D 11/02 (2006.01)
C08K 5/3417 (2006.01)
C07D 405/14 (2006.01)

(52) U.S. Cl.
USPC ......................... 106/31.78; 106/506; 548/456

(58) Field of Classification Search
USPC ........ 106/31.78, 498, 506; 548/456, 463, 492
See application file for complete search history.

(56) References Cited

U.S. PATENT DOCUMENTS

| | | | |
|---|---|---|---|
| 4,965,294 A | 10/1990 | Ohngemach | |
| 6,492,533 B1 * | 12/2002 | Connor et al. | 549/299 |
| 6,503,937 B1 | 1/2003 | Nesvadba et al. | |
| 6,524,382 B1 | 2/2003 | Bujard et al. | |
| 6,566,425 B1 * | 5/2003 | Connor et al. | 524/83 |
| 2010/0119858 A1 | 5/2010 | Benkhoff et al. | |
| 2010/0186891 A1 | 7/2010 | Ruch et al. | |
| 2011/0040018 A1 | 2/2011 | Moeck et al. | |
| 2011/0166284 A1 | 7/2011 | Hu et al. | |
| 2012/0172498 A1 * | 7/2012 | Fontana et al. | 548/456 |

FOREIGN PATENT DOCUMENTS

| | | |
|---|---|---|
| GB | 2014152 A | 8/1979 |
| WO | 00/24736 A | 5/2000 |
| WO | 01/32577 A | 10/2001 |
| WO | 2009/010521 A | 1/2009 |
| WO | WO 2009/010521 A3 * | 1/2009 |
| WO | WO 2010/081756 A1 * | 7/2010 |

OTHER PUBLICATIONS

"Production in Fine Chemical Industry and Application thereof", edited by fine chemical industry teaching and research section, Guangdong Industry University, Guangdong Science and Technology Press, May 2000, 1st Edition, pp. 55-68.

English language translation of "Production in Fine Chemical Industry and Application thereof", edited by fine chemical industry teaching and research section, Guangdong Industry University, Guangdong Science and Technology Press, May 2000, 1st Edition, pp. 1-18.

* cited by examiner

Primary Examiner — Helene Klemanski
(74) Attorney, Agent, or Firm — Shruti Costales

(57) ABSTRACT

A process for preparing a black colorant, preferably a black pigment, characterized in that a compound of the Formula (I) is reacted with a compound of the Formula (II) in a molar ratio of 1:2, in the presence of a catalyst which in water at 25° C. has a pK≤4.5. For the definition of $R_1$ to $R_7$, refer to the description; preferably all are H. Likewise claimed are new crystal polymorphs obtainable by this process, and preferably single-phase mixed crystals. Also claimed are synergistic compositions. These compositions exhibit increased light stability in plastics stabilized with basic light stabilizers when they are pigmented with colorants of the invention rather than with known black pigments such as carbon black. The specification also relates, furthermore, to the use of the black colorants of the invention for coloring paints, printing inks and plastics in the mass, and to mulch film, instrument panels, woven fabrics, garden furniture items or elements for the construction industry that are pigmented with said colorants.

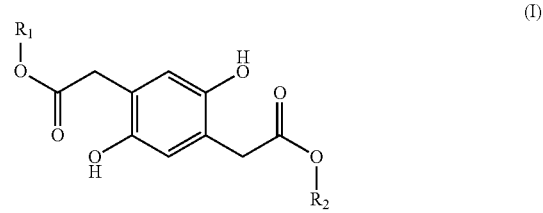

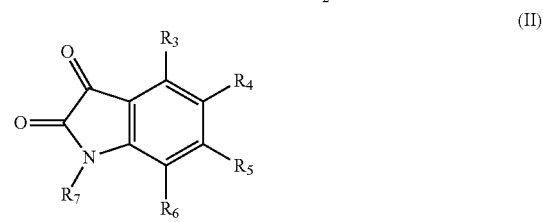

20 Claims, 12 Drawing Sheets

ORGANIC BLACK PIGMENTS AND THEIR PREPARATION

CROSS-REFERENCE TO RELATED APPLICATIONS

This application is the National Stage entry of PCT/EP2009/067953 filed Dec. 28, 2009, which claims priority to EP 09150817.6 filed Jan. 19, 2009, wherein the contents of all applications are herein incorporated by reference.

BACKGROUND OF THE INVENTION

The most commonly used black pigment is carbon black (C. I. Pigment Black 7). Carbon black is cheap and has excellent applications properties, such as light stability and weather stability, high colour strength, blackness, and neutral grey hues in a mixture with white pigments such as titanium dioxide (C. I. Pigment White 6), but also has serious disadvantages, such as problems with dispersibility of very fine particles, excessive electrical conductivity, and high absorption of near-infrared radiation (NIR) from the solar spectrum, which may lead to severe heating and possibly even to the destruction of the pigmented substrate or to the failure of the pigmented article.

In order to solve the problem, mixed metal oxides (MMO) have been proposed. While these oxides reflect the NIR radiation, their colour is weak and they contain heavy metals which are not unobjectionable for humankind and the environment.

There have also already been proposals of organic black pigments, such as C. I. Pigment Black 32, for example. Disadvantages shared by all known organic black pigments, however, are the fact that they are unsatisfactorily pitch-black (inadequate jetness) and that their hues in a mixture with white pigments are not a neutral grey but instead, depending on pigment, have a relatively strong tinge of colour, being tinged green, red, violet or brown, for example.

WO 00/24 736 discloses the compound of the formula

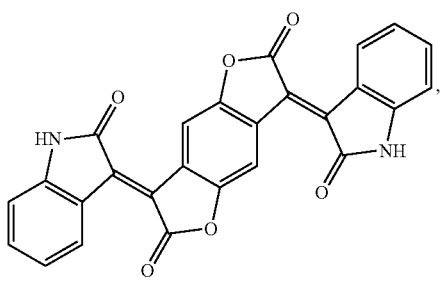 [SMILES: O=C1Nc2ccccc2/C1=C1\C(=O)Oc2cc3c(cc21)OC(=O)/C3=C1/C(=O)Nc2ccccc21]

which is obtained by condensing the bisbenzofuranone of the formula

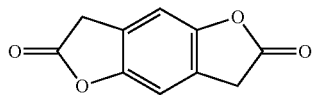

with isatin in acetic acid of unknown strength in the form of a violet powder (Example 12b). US 2003/0 083 407 complains that the yield is suspect. Moreover, no applications properties at all are disclosed, and the violet powder is in a highly aggregated form, whose dispersibility in plastics, for example, is entirely unsatisfactory.

WO 01/32 577 discloses glass-like materials, including (Example 41) a glass plate which is coated with tetraethoxysilane, aqueous nitric acid and the colorant of the formula

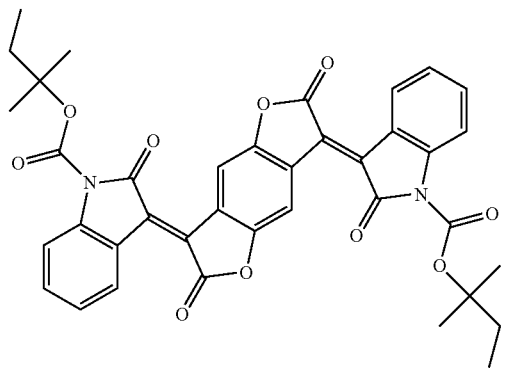 [SMILES: CCC(C)(C)OC(=O)N1C(=O)/C(=C2/C(=O)Oc3cc4c(cc32)OC(=O)/C4=C2/C(=O)N(C(=O)OC(C)(C)CC)c3ccccc32)c2ccccc21]

and which after heating to 200° C. has an absorption maximum at 760-765 nm.

Mixtures of organic colour pigments, which are likewise known, usually lead, like their individual components, to green-, red-, violet- or brown-tinged hues during the necessary dispersing step, since the individual components differ in their dispersibilities. Each dispersion method, therefore, requires extensive formulation work, and can subsequently no longer be changed rapidly as and when required—in actual practice, this is a disadvantage.

What remains, therefore, is the hitherto unfulfilled desire for heavy metal-free, jet-black pigments with high colour strength and good dispersibility, and also with very low conductivity and low absorption of near-infrared radiation.

WO 2009/010 521 is a patent application governed by Art. 54(3) EPC and Rule 64.3 PCT.

It has now been found, surprisingly, that, in a new, single-stage process, highly dispersible, strong, jet-black colorants (almost always pigments) having good fastnesses are obtained. In combination with basic additives, such as hindered amines (HALS) and/or UV absorbers of benzotriazole or triazine type, moreover, the physical durabilities which are obtained in plastics on weathering are, surprisingly, better than with known black pigments such as carbon black.

SUMMARY OF THE INVENTION

The invention accordingly provides a process for preparing a black colorant, preferably a black pigment, characterized in that a compound of the formula

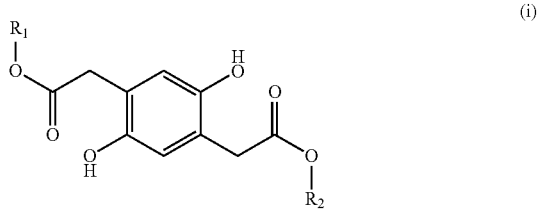

(i)

is reacted with a compound of the formula

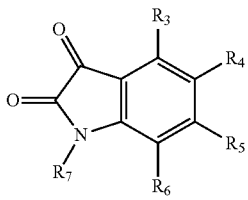

in a molar ratio of 1:2 in the presence of a catalyst which in water at 25° C. has a pK≤4.5, where $R_1$ and $R_2$ independently of one another are H or are $C_1$-$C_{24}$alkyl, $C_3$-$C_{24}$cycloalkyl, $C_2$-$C_{24}$alkenyl, $C_3$-$C_{24}$cycloalkenyl or $C_2$-$C_{24}$alkynyl each unsubstituted or substituted by halogen or $C_1$-$C_8$alkoxy; are $C_7$-$C_{24}$aralkyl which is unsubstituted or substituted one or more times by halogen, nitro, cyano, $C_1$-$C_8$alkyl and/or $C_1$-$C_8$alkoxy; or are $C_6$-$C_{24}$aryl which is unsubstituted or substituted one or more times by halogen, nitro, cyano, $C_1$-$C_8$alkyl and/or $C_1$-$C_8$alkoxy;

$R_3$ is H, F, Cl, $R_8$ or $OR_8$, preferably H or F;

$R_4$, $R_5$ and $R_6$ independently of one another are H, F, Br, Cl, COOH, $COOR_8$, $CONH_2$, $CONHR_8$, $CONR_8R_8$, CN, $COR_8$, $SO_3H$, $SO_2Cl$, $SO_2NH_2$, $SO_2NHR_8$, $SO_2NR_8R_8$, $SO_2R_8$, $NO_2$, $R_8$, $OR_8$, $SR_8$, $NR_8R_8$, $NHCOR_8$ or

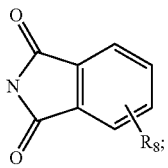

or $R_3$ and $R_4$, $R_4$ and $R_5$ or $R_5$ and $R_6$ in pairs together form a $C_1$-$C_6$alkylenedioxy, $C_3$-$C_6$alkylene, $C_3$-$C_6$alkenylene or 1,4-butadienylene radical, each unsubstituted or substituted one or more times by F, $OR_8$, $NO_2$, oxo, thioxo or $SO_3H$;

$R_7$ is H or is $C_1$-$C_{24}$alkyl, $C_3$-$C_{24}$cycloalkyl, $C_2$-$C_{24}$alkenyl, $C_3$-$C_{24}$cycloalkenyl, $C_2$-$C_{24}$alkynyl or $C_2$-$C_{12}$heterocycloalkyl, each unsubstituted or substituted one or more times by F, oxo or thioxo and uninterrupted or interrupted one or more times by O, S or $NR_8$; or is $C_7$-$C_{24}$aralkyl, $C_1$-$C_{12}$heteroaryl-$C_1$-$C_8$alkyl, $C_6$-$C_{24}$aryl or $C_1$-$C_{12}$heteroaryl, each unsubstituted or substituted one or more times by oxo, thioxo, F, Br, Cl, COOH, $COOR_8$, $CONH_2$, $CONHR_8$, $CONR_8R_8$, CN, $COR_8$, $SO_3H$, $SO_2Cl$, $SO_2NH_2$, $SO_2NHR_8$, $SO_2NR_8R_8$, $SO_2R_8$, $NO_2$, $R_8$, $OR_8$, $SR_8$, $NR_8R_8$, $NHCOR_8$ or

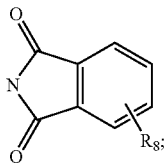

and each $R_8$, independently of all other $R_8$s, is $C_1$-$C_{24}$alkyl, $C_3$-$C_{24}$cycloalkyl, $C_2$-$C_{24}$alkenyl, $C_3$-$C_{24}$cycloalkenyl, $C_2$-$C_{24}$alkynyl or $C_2$-$C_{12}$heterocycloalkyl, each unsubstituted or substituted one or more times by F, oxo, thioxo, $OR_9$, $SR_9$ or $NR_9R_9$; or is $C_7$-$C_{24}$aralkyl, $C_1$-$C_{12}$heteroaryl-$C_1$-$C_8$alkyl, $C_6$-$C_{24}$aryl or $C_1$-$C_{12}$heteroaryl, each unsubstituted or substituted one or more times by oxo, F, Br, Cl, COOH, $CONH_2$, $CONHR_9$, $CONR_9R_9$, $SO_3H$, $SO_2Cl$, $SO_2NH_2$, $SO_2NHR_9$, $SO_2NR_9R_9$, CN, $NO_2$, $OR_9$, $SR_9$, $NR_9R_9$, $NHCOR_9$ or

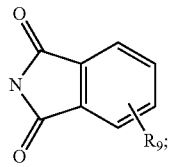

or two vicinal $R_8$s together form —O—CO—O—, —O—CS—O—, —CO—N—CO—, —N—CO—N—, —N=S=N—, —N=C=C—, —O=C=C—, —S=C=C—, —O—C=N—, —S—C=N—, —N=N=N—, —N=C—C=C—, —C=N—C=C—, —N=C—C=N—, —C=N—N=C— or —C=N—C=N— or —C=C—C=C—, in which each —C= and —N—, independently of all other —C= and —N—, is substituted by H or $R_9$;

or two geminal or vicinal $R_8$s together form a $C_3$-$C_8$alkylene or $C_3$-$C_8$alkenylene radical, each unsubstituted or substituted one or more times by F, oxo or thioxo, and in which 0, 1 or 2 non-vicinal methylene units may be replaced by O, S or $NR_9$; and each $R_9$, independently of all other $R_9$s, is $C_1$-$C_8$alkyl, $C_3$-$C_6$cycloalkyl or benzyl, each unsubstituted or substituted one or more times by oxo, thioxo, F and/or O—$C_1$-$C_8$alkyl; or is phenyl or $C_1$-$C_5$heteroaryl, each unsubstituted or substituted one or more times by F, Br, Cl, CO—$C_1$-$C_8$alkyl, COOH, $CONH_2$, $CONHC_1$-$C_8$alkyl, $CON(C_1$-$C_8$alkyl$)_2$, $SO_3H$, $SO_2Cl$, $SO_2NH_2$, $SO_2NHC_1$-$C_8$alkyl, $SO_2N(C_1$-$C_8$alkyl$)_2$, CN, $NO_2$, $C_1$-$C_8$alkyl, $OC_1$-$C_8$alkyl, $SC_1$-$C_8$alkyl or $N(C_1$-$C_8$alkyl$)_2$;

or two vicinal $R_9$s together form —O—CO—O—, —O—CS—O—, —CO—N—CO—, —N—CO—N—, —N=S=N—, —N=C=C—, —O=C=C—, —S=C=C—, —O—C=N—, —S—C=N—, —N=N=N—, —N=C—C=C—, —C=N—C=C—, —N=C—C=N—, —C=N—N=C— or —C=N—C=N— or —C=C—C=C—, in which each —C= and —N— independently of all other —C= and —N— is substituted by H, F, oxo, thioxo, $C_1$-$C_8$alkyl or $OC_1$-$C_8$alkyl;

or two geminal or vicinal $R_9$s together form a $C_3$-$C_8$alkylene or $C_3$-$C_8$alkenylene radical, each unsubstituted or substituted one or more times by oxo or thioxo, and in which 0, 1 or 2 non-vicinal methylene units may be replaced by O, S or $N(C_1$-$C_8$alkyl).

DETAILED DESCRIPTION OF THE INVENTION

Figure 1:
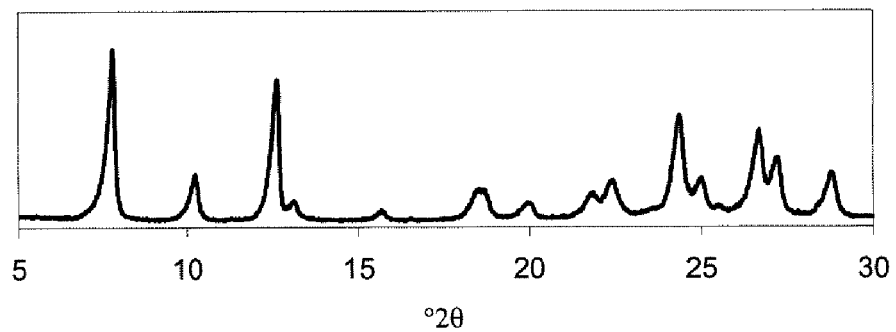
FIG. 1 represents an X-ray powder diagram of the product obtained in Example 1.

Colorants considered black are those which in the masstone in dispersion in a transparent, substantially colourless substrate (for example, polyester/cellulose acetobutyrate varnish, PVC film or polyester plaque) have a colour saturation $C^* \leq 5$ at full opacity (CIE 1976 L*C*h colour space). In general, the opacity (<1% transmittance) that is satisfactory for colorimetry can be achieved readily, in accordance with customary test methods, with a colorant concentration of around 2 g/m², otherwise, the concentration of colorant in the substrate should be increased.

The reaction proceeds in a completely satisfactory manner, possibly even in spite of steric hindrance by substituents $R_3$ such as chlorine or methyl, for example. The colorants in which $R_3$ is H, however, are particularly preferred on account of their even blacker shade, lower migration and better light stability, also in combination with all further preferences for $R_4$, $R_5$, $R_6$ and $R_7$.

$R_1$ and $R_2$ are preferably hydrogen or unsubstituted or substituted $C_1$-$C_8$alkyl or $C_5$-$C_8$cyclo-alkyl, more particularly hydrogen, unsubstituted $C_1$-$C_8$alkyl or $C_5$-$C_8$cycloalkyl, more preferably hydrogen, $C_1$-$C_4$alkyl or cyclohexyl, especially hydrogen, methyl, ethyl and isobutyl.

It is preferred to react a compound of the formula

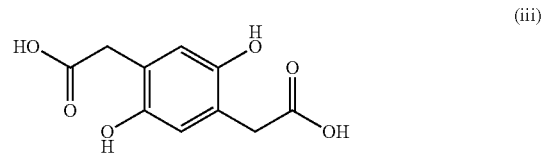 [SMILES: O=C(O)Cc1cc(O)c(CC(=O)O)cc1O]
(iii)

with a compound of the formula

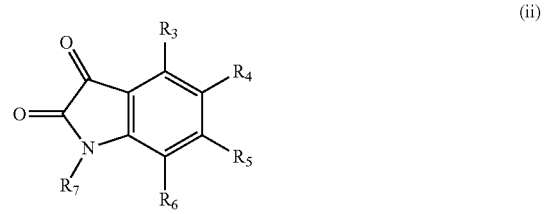
(ii)

in a molar ratio of 1:2.

With particular preference $R_3$, $R_5$ and $R_7$ are H and $R_4$ and $R_6$ independently of one another are H, F, Br, Cl, COOH, $COOR_8$, $CONH_2$, $CONHR_8$, $CONR_8R_8$, CN, $COR_8$, $SO_3H$, $SO_2Cl$, $SO_2NH_2$, $SO_2NHR_8$, $SO_2NR_8R_8$, $SO_2R_8$, $NO_2$, $R_8$, $OR_8$ or $NHCOR_8$, or $R_5$ and $R_6$ together form a 1,4-butadienylene radical.

Especially preferred are reaction products of a compound of the formula

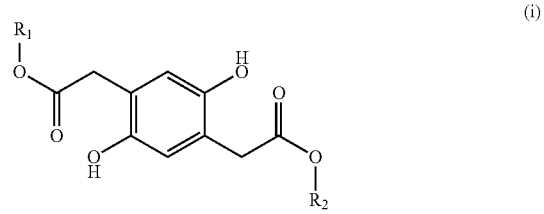
(i)

with a compound of the formula

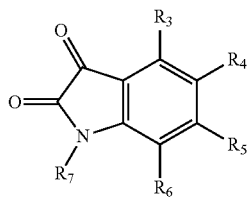

(ii)

in a molar ratio of 1:2, the compound of the formula (ii) being selected from the group consisting of compounds having the following substitution patterns:
- $R_3=R_4=R_5=R_6=R_7=H$;
- $R_3=R_5=R_6=R_7=H$, $R_4=NO_2$;
- $R_3=R_5=R_6=R_7=H$, $R_4=OCH_3$;
- $R_3=R_5=R_6=R_7=H$, $R_4=Cl$;
- $R_3=R_5=R_6=R_7=H$, $R_4=F$;
- $R_3=R_5=R_6=R_7=H$, $R_4=Br$;
- $R_3=R_5=R_6=R_7=H$, $R_4=SO_3H$;
- $R_3=R_5=R_6=R_7=H$, $R_4=COOH$;
- $R_3=R_5=R_6=R_7=H$, $R_4=N(CH_3)_2$;
- $R_3=R_5=R_6=R_7=H$, $R_4=NHCOC_1$-$C_{18}$alkyl, more particularly NHCOC$_1$-C$_{12}$alkyl;
- $R_3=R_5=R_6=R_7=H$, $R_4=C_1$-$C_{20}$alkyl, more particularly $C_1$-$C_{14}$alkyl;
- $R_3=R_5=R_6=R_7=H$, $R_4=C_2$-$C_{20}$alkoxy, more particularly $C_2$-$C_{14}$alkoxy;
- $R_3=R_5=R_7=H$, $R_4=R_6=CH_3$;
- $R_3=R_5=R_7=H$, $R_4=R_6=Cl$;
- $R_3=R_5=R_7=H$, $R_4=Cl$, $R_6=CH_3$;
- $R_3=R_4=R_5=R_6=H$, $R_7=CH_3$;
- $R_3=R_4=R_5=R_6=H$, $R_7=C_6H_5$; and
- $R_3=R_4=R_7=H$, $R_5$ and $R_6$ together=1,4-butadienylene.

In the case of simultaneous or sequential use of two or more compounds of the formula

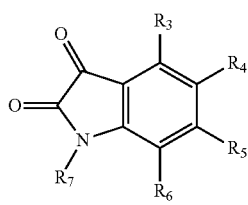

(ii)

(as disclosed later on below), this preferred substitution pattern also applies for one or more of the further compounds of the formula (ii), more preferably for all further compounds of the formula (ii).

The catalyst in water at 25° C. advantageously has a pK≤4.5, preferably a pK≤2.0. The amount of catalyst is not essential per se; for example, $5 \cdot 10^{-3}$ to 5 mol of catalyst, preferably from 0.1 to 1 mol of catalyst, per mole of compound of the formula (i), is rational. It should be noted here that, depending on catalyst and reaction medium (and/or solvent), it may be costly and inconvenient to remove the catalyst quantitatively from the desired black colorant by usual washing methods. A small residual amount of catalyst, of 1 ppb to 5% by weight catalyst, for example, preferably of 1 ppm to 0.5% by weight catalyst, based on the product as a whole, is usually acceptable in practice, however, since it is favourable to the properties of the colorants, or at least not detrimental. For particularly exacting requirements, the colorant can be subjected to the conventional procedures of repeated slurrying with water and customary solvents, filtration and washing until the catalyst is removed entirely or until the residual amount of catalyst is no longer detectable (<1 ppb).

The reaction takes place usually, approximately, at a pressure of $2 \cdot 10^2$ to $2 \cdot 10^6$ Pa and at a temperature of 20 to 250° C., preferably at a temperature of 50 to 220° C. The reaction is generally at an end, in a discontinuous apparatus, after ½ to 100 hours. In a continuous apparatus, the reaction time may be substantially shorter, as in the case, for example, of passage through a reaction zone, at a temperature of up to 300° C., of a reactor or microreactor.

As a reaction medium it is possible to use any compositions or substances that are inert with respect to the reactants, the reaction product and the catalyst and which are acidic or neutral and are liquid at the reaction temperature. Anhydrous reaction media are advantageous, as are also mixtures thereof with up to 50% by weight of water, based on the amount of anhydrous reaction medium. Preference is given to anhydrous reaction media which are hygroscopic or form azeotropes with water, optionally in mixtures with one another and/or in a mixture with water.

Suitable inert reaction media are, for example, alcohols, ethers, acids, esters, amides, nitriles, optionally unsaturated or halogenated hydrocarbons, nitro, thio or corresponding polyfunctional compounds, such as methanol, ethanol, 2,2,2-trifluoroethanol, n-propanol, 2,2,3,3-tetrafluoro-1-propanol, isopropanol, n-butanol, sec-butanol, tert-butanol, isobutanol, sec-amyl alcohol, tert-amyl alcohol, 2-methoxyethanol, 1-methoxypropan-2-ol, ethylene glycol, propylene glycol, butylene glycol, 1,5-pentanediol, hexylene glycol, thiodiglycol, low molecular weight polyethylene glycols or polypropylene glycols, preferably with a molecular weight of 100 to 800 (diethylene glycol, triethylene glycol, tetraethylene glycol, polyethylene glycol 200, polyethylene glycol 300, polyethylene glycol 400, polyethylene glycol 600, dipropylene glycol, tripropylene glycol, polypropylene glycol P 400, polypropylene glycol P 425) and their ethers (e.g. propylene oxide monomethyl ether, dipropylene oxide monomethyl ether), glycerol, 1,2,6-hexanetriol, 1,2-dimethoxyethane, 1,2-diethoxyethane, 2-n-butoxyethanol, 2-methoxyethanol, 2-ethoxyethanol, diethylene glycol monobutyl ether, 2-(2-methoxyethoxy)ethanol, 2-(2-ethoxyethoxy)ethanol, 2-[2-(2-methoxyethoxy)ethoxy]ethanol or 2-[2-(2-ethoxyethoxy) ethoxy]-ethanol; diethyl ether, dibutyl ether, tetrahydrofuran, dioxane, Dowtherm™ (e.g. A, G, J, MX, Q, RP or T), formic acid, acetic acid, propionic acid, isobutyric acid, lactic acid, 2-ethylhexanoic acid; methyl acetate, ethyl acetate, n-propyl acetate, isopropyl acetate, butyl acetate, methyl propionate, ethyl propionate, n-propyl propionate, isopropyl propionate, butyl propionate, methyl lactate, methyl isobutyrate, ethylene carbonate, caprolactone, polycaprolactone; acetamide, formamide, methylacetamide, methylformamide, N,N-dimethylformamide, N,N-dimethylacetamide, N-methylpyrrolidone, 1,3-dimethyl-2-imidazolidone, caprolactam, valerolactam, 1,1,2,2-tetramethylurea; acetonitrile, benzonitrile; pentane, n-hexane, cyclohexane, methylcyclohexane, 1,2-dimethylcyclohexane, ethylcyclohexane, decalin, aromatic-free, low-aromatic or aromatic-rich hydrocarbon distillates (e.g. light or heavy petroleum fractions, petroleum ether, Solvesso™ 100, 150, 200, Shellsol™ D38, D40, D43, D60, DSC, D70, D80, D90, D100, D100 S); dichloroethane, trichloroethane, trichloroethylene, tetrachloroethylene, benzene, toluene, xylene, anisole, chlorobenzene, dichlorobenzene, trichlorobenzene, o-cymene, m-cymene, p-cymene, sec-butylbenzene, tert-butylbenzene, 2-pentylbenzene, isopent-2-ylbenzene, tert-amylbenzene, tetralin; nitrobenzene;

dimethyl sulfoxide, sulfolane; or polyphosphoric acid; and also mixtures thereof with one another and/or with water.

Preferred reaction media are aqueous acetic acid, glacial acetic acid, toluene, xylene, chlorobenzene, dichlorobenzene, nitrobenzene, and saturated or aromatic hydrocarbons which boil at 150 to 300° C., and also polyphosphoric acid.

Water can optionally be removed from the reaction mixture, preferably azeotropically. Surprisingly, however, it has proved to be the case that the reaction proceeds entirely satisfactorily even without removal of water from the reaction medium. The addition of agents which react with water, such as carboxylic anhydrides or carbonyl chlorides, on the other hand, is generally undesirable, since these agents disrupt the course of the reaction and lead to the formation of unwanted by-products. An exception to this is polyphosphoric acid, since its reaction with water is sufficiently slow. Advantageously, of course, any substances which lead to the formation of unwanted by-products with isatin are avoided as well.

The black pigments of the invention are generally isolated in a manner conventional in the art, by filtration and washing of the filter residue, followed by drying at −30° C. to 200° C., optionally under reduced pressure. Black colorants of the invention which are soluble in the reaction medium are advantageously converted beforehand into insoluble salts or transferred to a liquid, neutral or acidic medium with low or no solvency.

The black colorants obtainable in accordance with the invention are characterized by their empirical formula, conforming to $C_{10}H_2O_2$ plus two times the empirical formula of the compound of the formula (ii). In the infrared, moreover, they exhibit carbonyl vibrations, generally from 2 to 4, often overlapping vibrations at approximately between 1610 cm$^{-1}$ and 1780 cm$^{-1}$. The empirical formula may be derived from the exact mass of the molecular ion in the mass spectrum (e.g. LDI-MS) and/or from the elemental analysis. It is assumed, but has not so far been proved, that the black colorants obtainable in accordance with the invention are of the formula

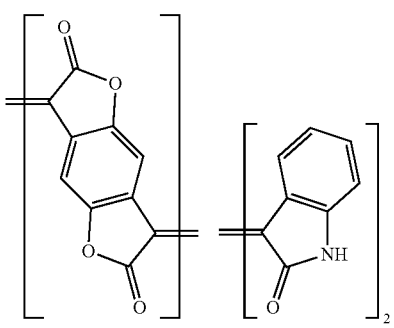

or tautomers thereof, it being possible for each of the two exocyclic double bonds, independently of one another, to have the E or Z isomerism (the former is more sterically favourable).

The black colorants obtainable in accordance with the invention are preferably composed of non-aggregated pigment particles, characterized by an average particle size L of 10 nm to 10 μm, with preferably 60%-100% by weight, more preferably 80%-100% by weight, of the particles having a particle size of L±½ L. The particle size is the diameter of the equivalent sphere ("Equivalent Settling Rate Diameter" $x_w$). The particle sizes are to be averaged according to the weight of the particles of each size fraction.

Different fractions are of particular interest according to the particular application. Where transparency is desired, for ink, paint or electronics applications, for example, it is preferred to use pigment particles having an average particle size L of ~10 nm to ~200 nm. Semi-opacity, for the mass colouring of thermoplastics, for example, is obtained preferably with pigment particles having an average particle size L of ~201 nm to ~400 nm. Opaque pigmentations are obtained, independently of the application, preferably with pigment particles having an average particle size L of ~401 nm to ~999 nm. For effect pigmentations, particular suitability is possessed by pigment particles having an average particle size L of ~1 μm to ~10 μm. In this context, an aspect ratio ≥5, particularly in the case of an average particle size L≥400 nm, results in surprising optical and thermal effects, such as a high NIR reflectivity. The aspect ratio is the ratio of the particle length (greatest dimension) to the particle height (smallest dimension). The aspect ratio can be determined in accordance with methods that are known per se to the skilled person—for example, in the manner disclosed in PCT/EP 2008/067 011.

Alkyl, alkenyl or alkynyl may be straight-chain or branched. Alkenyl is a mono- or polyunsaturated alkyl, it being possible for two or more double bonds to be optionally isolated or conjugated. Alkynyl is alkyl or alkenyl with one or more instances of double unsaturation, it being possible for the triple bonds to be optionally in isolation or to be conjugated with one another or with double bonds. Cycloalkyl or cycloalkenyl is monocyclic or polycyclic alkyl or alkenyl, respectively.

$C_1$-$C_{24}$Alkyl may therefore be, for example, methyl, ethyl, n-propyl, isopropyl, n-butyl, sec-butyl, isobutyl, tert-butyl, 2-methylbutyl, 2,2-dimethylpropyl, n-pentyl, 2-pentyl, 3-pentyl, n-hexyl, heptyl, n-octyl, 1,1,3,3-tetramethylbutyl, 2-ethylhexyl, nonyl, decyl, undecyl, dodecyl, tridecyl, tetradecyl, pentadecyl, hexadecyl, heptadecyl, octadecyl, nonadecyl, eicosyl, heneicosyl, docosyl or tetracosyl.

$C_3$-$C_{24}$Cycloalkyl may therefore be, for example, cyclopropyl, cyclopropylmethyl, cyclobutyl, cyclopentyl, cyclohexyl, cyclohexylmethyl, trimethylcyclohexyl, thujyl, norbornyl, bornyl, norcaryl, caryl, menthyl, norpinyl, pinyl, 1-adamantyl, 2-adamantyl, 5α-gonyl or 5ξ-pregnyl.

$C_2$-$C_{24}$Alkenyl is, for example, vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, or any isomer of hexenyl, octenyl, nonenyl, decenyl, dodecenyl, tetradecenyl, hexadecenyl, octadecenyl, eicosenyl, heneicosenyl, docosenyl, tetracosenyl, hexadienyl, octadienyl, nonadienyl, decadienyl, dodecadienyl, tetradecadienyl, hexadecadienyl, octadecadienyl or eicosadienyl.

$C_3$-$C_{24}$Cycloalkenyl is, for example, 2-cyclobuten-1-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or camphenyl.

$C_2$-$C_{24}$Alkynyl is, for example, 1-propyn-3-yl, 1-butyn-4-yl, 1-pentyn-5-yl, 2-methyl-3 butyn-2-yl, 1,4-pentadiyn-3-yl, 1,3-pentadiyn-5-yl, 1-hexyn-6-yl, cis-3-methyl-2 penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl or 1-tetracosyn-24-yl.

$C_7$-$C_{24}$Aralkyl is, for example, benzyl, 2-benzyl-2-propyl, β-phenylethyl, 9-fluorenyl, α,α-dimethylbenzyl, ω-phenylbutyl, ω-phenyloctyl, ω-phenyldodecyl or 3-methyl-5-(1',1', 3',3'-tetramethylbutyl)benzyl. $C_7$-$C_{24}$Aralkyl may also be, for example, 2,4,6-tri-tert-butylbenzyl or 1-(3,5-dibenzylphenyl)-3-methyl-2-propyl. If $C_7$-$C_{24}$aralkyl is substituted, then not only the alkyl moiety but also the aryl moiety of the aralkyl group may be substituted, the latter alternative being preferred.

$C_6$-$C_{24}$Aryl is, for example, phenyl, naphthyl, biphenylyl, 2-fluorenyl, phenanthryl, anthracenyl or terphenylyl.

Halogen is chlorine, bromine, fluorine or iodine, preferably fluorine on alkyl and fluorine or chlorine on aryl.

$C_1$-$C_{12}$Heteroaryl is an unsaturated or aromatic radical having 4n+2 conjugated π electrons, examples being 2-thienyl, 2-furyl, 1-pyrazolyl, 2-pyridyl, 2-thiazolyl, 2-oxazolyl, 2-imidazolyl, isothiazolyl, triazinyl, triazolyl, tetrazolyl or any other ring system which is composed of thiophene, furan, pyridine, thiazole, oxazole, imidazole, isothiazole, thiadiazole, triazole, pyridine and benzene rings and which is unsubstituted or substituted by 1 to 6 ethyl, methyl, ethylene and/or methylene groups.

$C_2$-$C_{12}$Heterocycloalkyl is an unsaturated or partially unsaturated ring system radical, for example an epoxidyl, oxetanyl, aziridinyl; pyrrolidyl, piperidyl, piperazinyl, imidazolinyl, pyrazolidinyl, pyrazolinyl, morpholinyl, quinuclidinyl; or another $C_4$-$C_{12}$heteroaryl which is singly or multiply hydrogenated.

Examples of 5- to 12-membered rings include cyclopentyl, cyclohexyl, cycloheptyl or cyclooctyl, preferably cyclopentyl and more particularly cyclohexyl.

Unsubstituted or substituted $C_1$-$C_6$alkylenedioxy radicals are, for example,

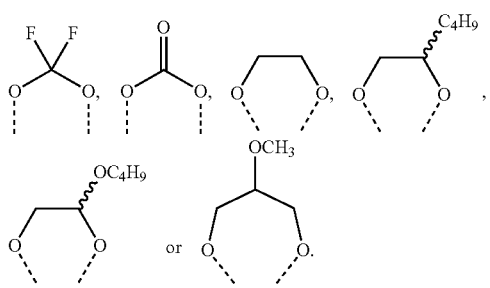

More times is, for example, two to ten times. Accordingly, alkyl interrupted and/or substituted one or more times by F and/or oxo can be, for example, $CF_3$, $COCH_3$, $COCF_3$, $(CF_2)_5CH_3$, $CH_2OCH_3$, $CH_2CH_2OH$, $CH_2CH_2OCOCH_3$, $CH_2COCH_2OH$ or $CH_2(CH_2OCH_2)_{10}CH_3$. The number of possible substituents is of course limited by the number of H atoms which can be substituted, and in groups which are interrupted more times the interrupting O atoms are advantageously separated from one another by at least 2 C atoms. In $C_7$-$C_{24}$aralkyl or $C_1$-$C_{12}$heteroaryl-$C_1$-$C_8$alkyl, the alkyl moiety is optionally substituted by oxo and thioxo.

The particle size is advantageously determined using a well-dispersed pigment suspension and a Joyce-Löbl disc centrifuge, the particles being assigned on the basis of weight, for example, to fractions each with a span of 20 nm. The particle size in this context is considered to be the diameter of the equivalent sphere ("Equivalent Settling Rate Diameter" $x_w$). The particle sizes are to be averaged in accordance with the weight of the particles of each size fraction. Of course, many parameters can affect the results, and so, given an inappropriate experimental procedure, it would even be possible to obtain incorrect results. The methodology described below, however, has proved to be particularly advantageous and of good reproducibility.

For the dispersion and deagglomeration of the pigment, 2 g of pigment are incorporated, in a standard 200 ml glass vessel with screw lid, into 48 g of alkyd varnish, consisting of 34.272 g of Alkydal® F310 (Bayer AG, D-Leverkusen, 60% by weight in Solventnaphtol™), 10.848 g of xylene, 1.152 g of n-butanol, 1.152 g of 1-methoxy-2-propanol and 0.576 g of a solution of 1 part by weight of low molecular weight methylpolysiloxane with a high fraction of volatile siloxanes (Baysilone® paint additive MA, Borchers GmbH, D-40764 Langenfeld) in 99 parts by weight of xylene.

Then 100 g of 2 mm glass beads are added, and the vessel is shaken in a shaker device (Skandex® type, for example) until it is found by optical microscopy that the number of remaining agglomerates bigger than about 2 μm has become so small that they have no substantial effect on the results of measurement. It is preferred to use a 620 W BAS instrument (Lau GmbH, D-58675 Hemer), which allows a large number of samples to be dispersed and deagglomerated at the same time. This instrument has a shaking frequency of around 619 per minute for a displacement of 32 to 45 mm (depending on charge). The dispersing and deagglomerating time in this case is typically from 1 to 6 hours, preferably from 2 to 4 hours, more particularly 3 hours. When dispersing and deagglomeration are complete, any unnecessary lengthening of the dispersing and deagglomerating time is to be avoided. By cooling with a stream of air, the temperature is kept advantageously in the range from about 20 to 50° C.

1 g of the resultant alkyd varnish dispersion is then introduced into 19 g of a liquid mixture which is composed of 323 mg of nitrocellulose containing 20% by weight plasticizer (low-viscosity printing-ink grade, degree of substitution ~2.0, ~11.1% N, 30% by weight in acetone produces, according to ISO 14446, a Höppler viscosity of 400 mPa·s; for example, NC AH 27 chips containing 20% by weight acetyl tributyl citrate, Hagedorn NC GmbH/Osnabrück DE), 133 mg of ethylcellulose (low-viscosity grade, 5% in toluene/ethanol 4:1 produces a viscosity of 3-5.5 mPa·s in the Ubbelohde viscosimeter; for example ETHOCEL® Std. 4, Dow Europe GmbH/Horgen CH), 11.704 g of ethyl acetate, 2.223 g of 1-acetoxy-2-ethoxyethane and 4.617 g of toluene and typically has a viscosity of 1.870 cP and a density of 0.932 g/cm³. After 5 minutes of stirring, the mixture is treated with 100 W of ultrasound for 1 minute at about 20-30° C., preferably using a Sonifier® B12 (Branson, Danbury Conn./USA), with external ice-water cooling.

For the purpose of measurement, 0.5 ml of the resulting suspension is injected in the usual way into a Joyce-Löbl disc centrifuge having a cavity of 10±1 cm in diameter and 6±1 mm in thickness, at 10 000 revolutions per minute, the cavity being largely filled with a liquid (spin fluid) consisting of 1.17% by weight of nitrocellulose (as above), 0.48% by weight of ethylcellulose (as above), 42.41% by weight of ethyl acetate, 8.06% by weight of 1-acetoxy-2-ethoxyethane, 16.73% by weight of toluene and 31.15% by weight of perchloroethylene (viscosity ~1.7 cP/specific weight ~1.08 g/cm³). By spectrophotometry the particles are quantitized with the disc in a virtually peripheral position. The particle size is determined using the Stokes equation $$T = \frac{6.299 \times 10^9 \cdot \eta}{d^2 \cdot N^2 \cdot p} \cdot \log_{10} \frac{R''}{R'}$$

in which
T=centrifuging time in minutes;
d=particle size in μm;
N=number of revolutions per minute (=10 000);

p=density difference between particles and initial fluid fill, in mg/cm³;

η=viscosity of the fluid in poise;

R"=radius at the peripheral measuring position of the disc, in cm;

R'=radius at the near-centre injection position of the disc, in cm.

Such conditions are familiar to the skilled analyst. The specific weight of the colorants obtainable in accordance with the invention can be determined experimentally, such as with a pycnometer, for example.

Alternatively the particle size can also be determined by laser scattering. This technique is well known per se, and precision instruments are available, for example, from Malvern Instruments Ltd (Malvern, Worcestershire/UK). In general the solid is suspended at about 1% in water together with one drop of a soluble copolymer (for example Luviskol® W73/BASF/polyvinyl-pyrrolidone/vinyl acetate) and dispersed in an ultrasound bath at room temperature for about 5-10 minutes prior to measurement.

The process of the invention provides the desired black colorants in a very good yield. A very particular advantage of the process of the invention, moreover, is that, through the choice of the reaction medium, it is extremely easy to influence the crystal polymorph and crystallinity. This opens up a direct route to new crystal polymorphs. The latter differ slightly in dispersibility and fastnesses, and sometimes also in their jet-black shade.

Furthermore, starting from a compound of the formula (i), the process of the invention leads, surprisingly, to a smaller amount of relatively soluble by-products than the process of WO 00/24736 that starts from the bisbenzofuranone of the formula

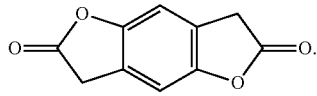

As a result, the migration and bleeding, and the yellowing tendency as well, are improved.

Through recrystallization (for example, from another solvent) and/or mechanical treatment (for example, in a wet mill or in a kneading apparatus), optionally in the presence of seed crystals and/or grinding assistants (for example, pulverized sodium chloride or sodium sulphate), some of these crystal polymorphs can be subsequently converted to others, although generally speaking this is neither necessary nor advantageous. Recrystallization for the purpose of increasing the crystallinity and optimizing the particle size distribution, however, is sensible.

For the purpose of optimizing the particle size distribution it is also possible to employ wet grinding or salt kneading. Both techniques are known per se, for example from WO 01/04 215 (the amorphization, however, is optional for the pigments of the invention) or WO 02/68 541 (in which case the power density may also amount, for example, to 3.0 kJ·s⁻¹ or more per liter of grinding space).

The invention accordingly also provides the following crystal polymorphs (°2θ/CuK$_\alpha$; the lines in the X-ray powder diagrams are identified, in addition to the gloss number, in accordance with their relative intensity: <33⅓%=w, 33⅓-66⅔%=m or 66⅔-100%=s; very weak, broad lines and humps are generally not included):

The reaction product obtainable by acidic catalysis from

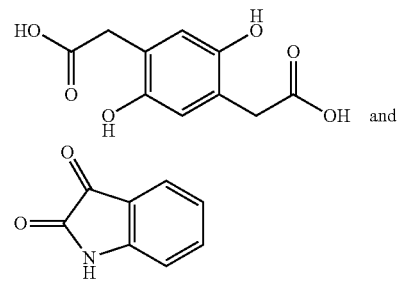

in a molar ratio of 1:2, of empirical formula C$_{26}$H$_{12}$N$_2$O$_6$, characterized by an X-ray powder diagram with lines at 7.8 s, 10.2 w, 12.6 s, 18.6 w, 21.8 w, 22.4 w, 24.4 m, 25.0 w, 26.7 m, 27.2 m and 28.8 w °2θ (FIG. 1). This crystal polymorph is obtained, for example, in low molecular weight polycaprolactone or toluene, in each case with p-toluene-sulphonic acid as catalyst.

The reaction product obtainable by acidic catalysis from

Figure 2:
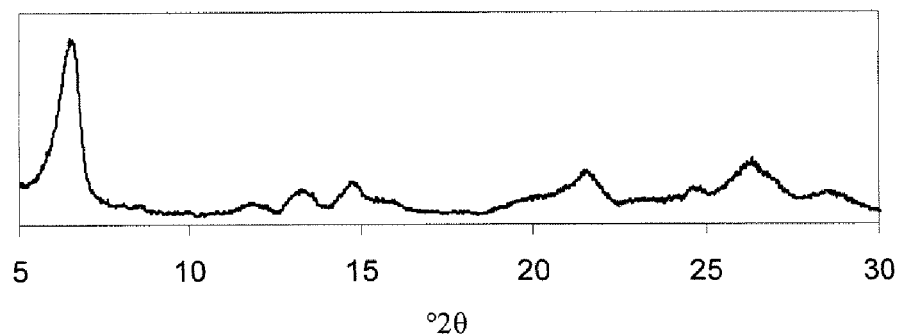
FIG. 2 represents an X-ray powder diagram of the product obtained in Example 2.

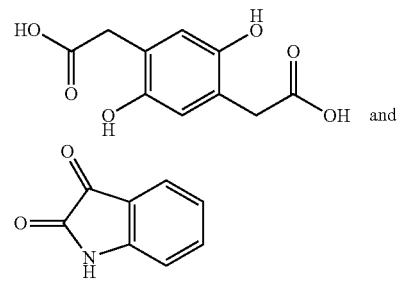

in a molar ratio of 1:2, of empirical formula C$_{26}$H$_{12}$N$_2$O$_6$, characterized by an X-ray powder diagram with lines at 6.6 s, 13.3 w, 14.8 w, 21.6 w, 24.5 w, 26.4 m and 28.7 w °2θ (FIG. 2). All of these lines are fairly broad, which suggests very fine primary particles. This crystal polymorph is obtained, for example, in aqueous acetic acid (60-90% by weight) with p-toluene-sulphonic acid as catalyst.

The reaction product obtainable by acidic catalysis from

Figure 3:
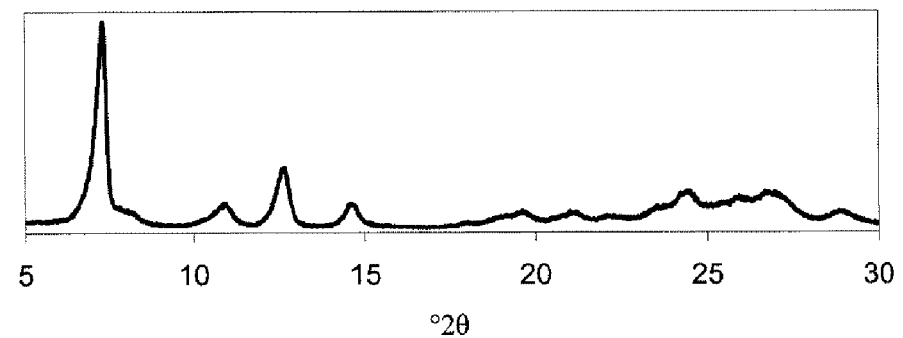
FIG. 3 represents an X-ray powder diagram of the product obtained in Example 3.

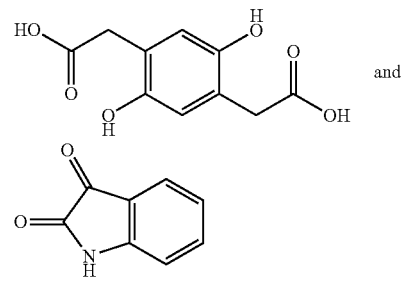

in a molar ratio of 1:2, of empirical formula C$_{26}$H$_{12}$N$_2$O$_6$, characterized by an X-ray powder diagram with lines at 7.3 s, 10.9 w, 12.7 w, 14.6 w, 24.5 w, 26.4 m and 28.7 w °2θ (FIG. 3). This crystal polymorph is obtained, for example, by recrystallization of the above-described crystal polymorph characterized by an X-ray powder diagram with lines at 6.6 s, 13.3 w, 14.8 w, 21.6 w, 24.5 w, 26.4 m and 28.7 w °2θ, from dimethyl sulphoxide.

The reaction product obtainable by acidic catalysis from

Figure 4:
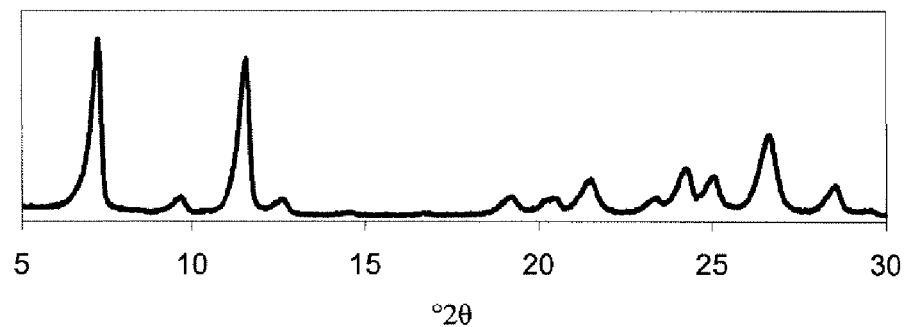
FIG. 4 represents an X-ray powder diagram of the product obtained in Example 7.

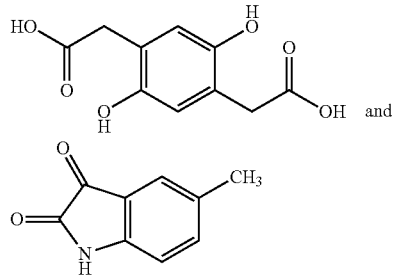

and in a molar ratio of 1:2, of empirical formula $C_{28}H_{16}N_2O_6$, characterized by an X-ray powder diagram with lines at 7.2 s, 9.7 w, 11.6 s, 12.7 w, 19.2 w, 20.4 w, 21.5 w, 24.3 w, 25.0 w, 26.6 w and 28.5 w °2θ (FIG. 4). This crystal polymorph is obtained, for example, in toluene with p-toluenesulphonic acid as catalyst.

The reaction product obtainable by acidic catalysis from

Figure 5:
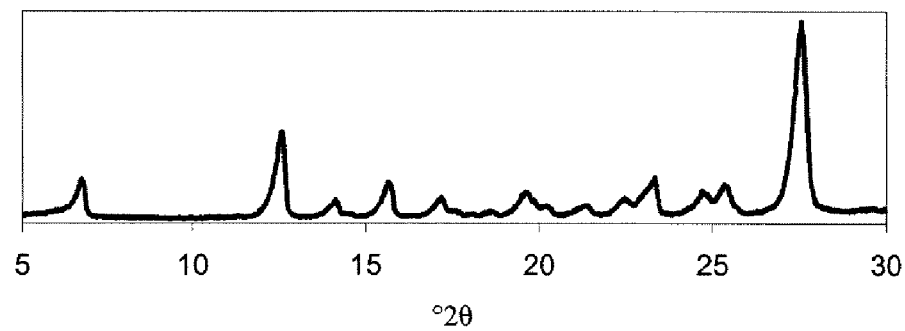
FIG. 5 represents an X-ray powder diagram of the product obtained in Example 8.

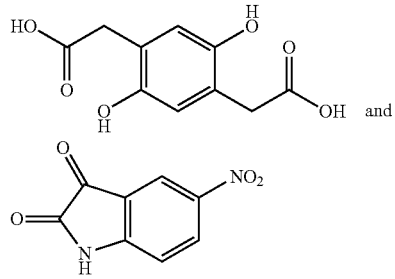

and in a molar ratio of 1:2, of empirical formula $C_{26}H_{10}N_4O_{10}$, characterized by an X-ray powder diagram with lines at 6.7 w, 12.6 m, 14.1 w, 15.7 w, 17.2 w, 19.6 w, 23.3 w, 24.8 w, 25.4 w, 27.6 s, 31.0 w and 34.3 w °2θ (FIG. 5). This crystal polymorph is obtained, for example, in glacial acetic acid with p-toluenesulphonic acid as catalyst.

The reaction product obtainable by acidic catalysis from

Figure 6:
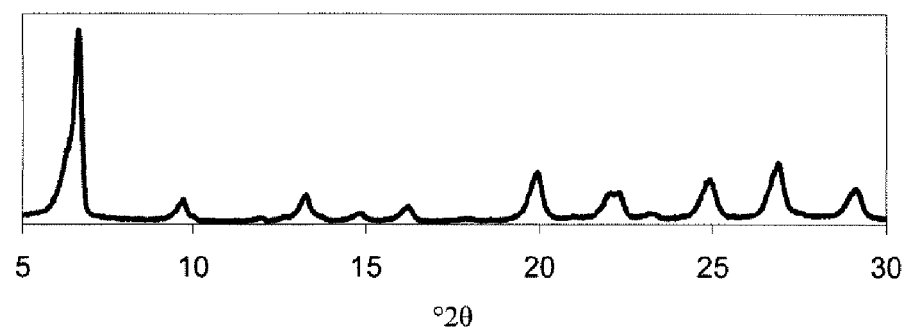
FIG. 6 represents an X-ray powder diagram of the product obtained in Example 9.

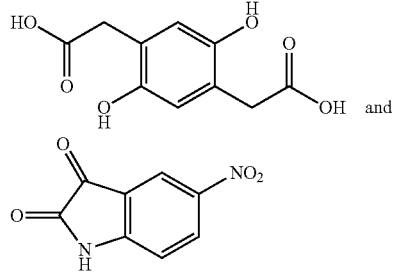

and in a molar ratio of 1:2, of empirical formula $C_{26}H_{10}N_4O_{10}$, characterized by an X-ray powder diagram with lines at 6.6 s, 9.7 w, 13.3 w, 16.2 w, 19.9 w, 22.1 w, 24.9 w, 26.9 w and 29.1 w °2θ (FIG. 6). At ~22.1 °2θ, a number of lines are poorly resolved. This crystal polymorph is obtained, for example, in aqueous acetic acid (60-90% by weight) with p-toluenesulphonic acid as catalyst.

The reaction product obtainable by acidic catalysis from

Figure 7:
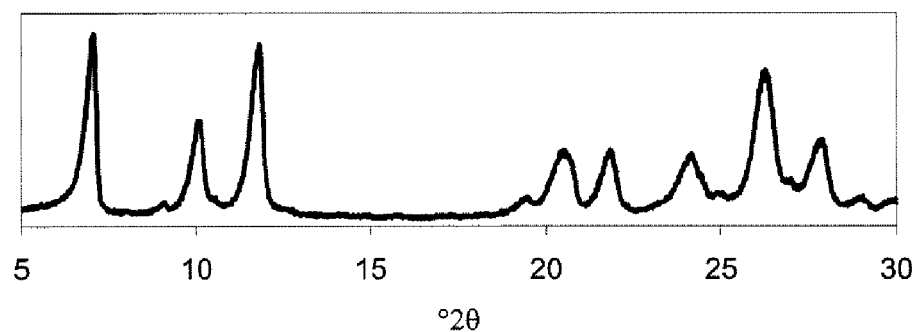
FIG. 7 represents an X-ray powder diagram of the product obtained in Example 10.

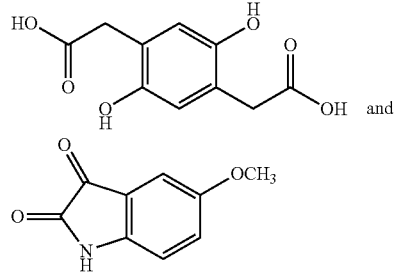

and in a molar ratio of 1:2, of empirical formula $C_{28}H_{16}N_2O_8$, characterized by an X-ray powder diagram with lines at 7.0 s, 10.1 m, 11.8 s, 20.5 m, 21.8 m, 24.2 m, 26.3 s and 27.9 m °2θ (FIG. 7). This crystal polymorph is obtained, for example, in glacial acetic acid with p-toluenesulphonic acid as catalyst.

The reaction product obtainable by acidic catalysis from

Figure 8:
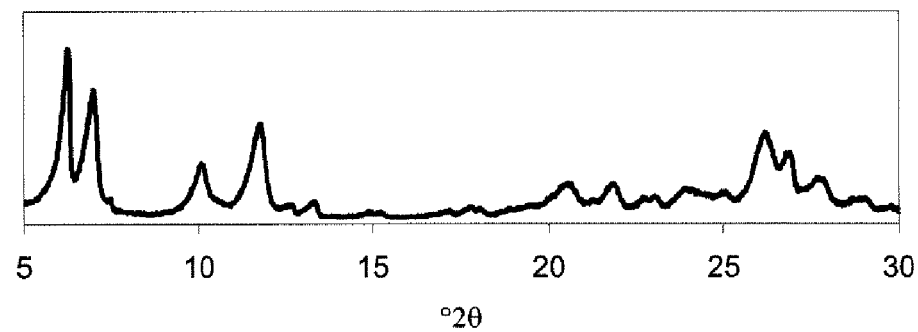
FIG. 8 represents an X-ray powder diagram of the product obtained in Example 11.

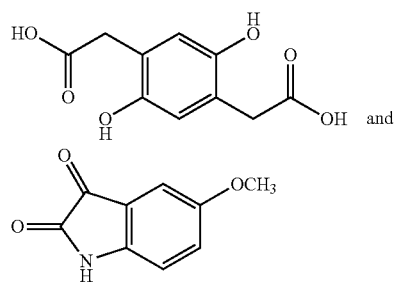

and in a molar ratio of 1:2, of empirical formula $C_{28}H_{16}N_2O_8$, characterized by an X-ray powder diagram with lines at 6.2 s, 7.0 s, 10.1 m, 11.8 m, 20.5 w, 21.8 w, 26.3 w, 26.9 m and 27.8 w °2θ (FIG. 8), this product containing, in comparison to the previous product, an additional crystal polymorph, characterized by an X-ray powder diagram with lines at 6.2 s, 13.3 m, 17.8 w, 22.8 w, 23.0 w, 25.0 w and 26.9 m °2θ. This product is obtained, for example, in aqueous acetic acid (60-90% by weight) with p-toluenesulphonic acid as catalyst.

The reaction product obtainable by acidic catalysis from

Figure 9:
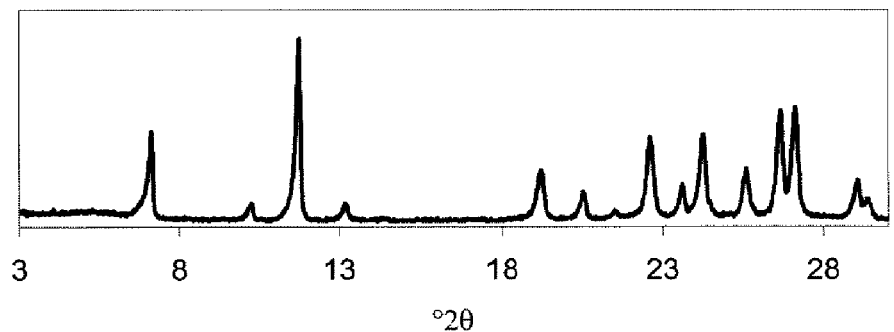
FIG. 9 represents an X-ray powder diagram of the product obtained in Example 12.

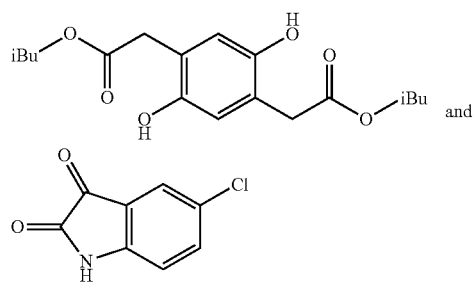

and in a molar ratio of 1:2, of empirical formula $C_{26}H_{10}N_2O_6Cl_2$, characterized by an X-ray powder diagram with lines at 7.1 m, 11.7 w, 19.2 w, 20.5 w, 22.6 m, 24.3 m, 25.6 w, 26.7 m, 27.1 m and 29.0 w °2θ (FIG. 9). This crystal polymorph is obtained, for example, in toluene with p-toluenesulphonic acid as catalyst.

The reaction product obtainable by acidic catalysis from

Figure 10:
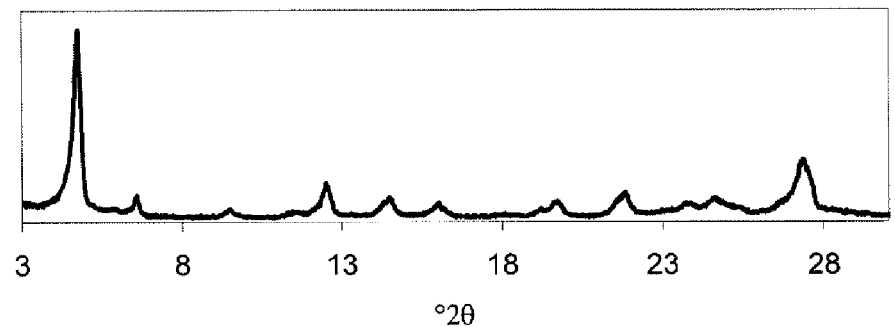
FIG. 10 represents an X-ray powder diagram of the product obtained in Example 13.

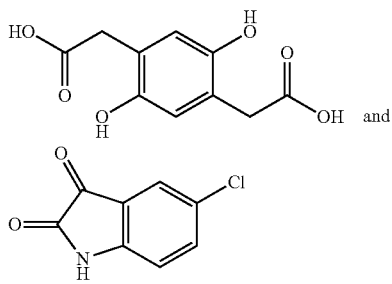
and in a molar ratio of 1:2, of empirical formula $C_{26}H_{10}N_2O_6Cl_2$, characterized by an X-ray powder diagram with lines at 4.7 s, 6.6 w, 9.3 w, 12.5 w, 14.5 w, 16.0 w, 19.7 w, 21.8 w, 24.6 w and 27.4 w °2θ (FIG. 10). This crystal polymorph is obtained, for example, in aqueous acetic acid (60-90% by weight) with p-toluenesulphonic acid as catalyst. In comparison to the preceding crystal polymorph, an additional crystal polymorph is present, characterized by an X-ray powder diagram with lines at 4.7 s, 9.3 w, 14.5 w, 16.0 w, 19.7 w and 24.6 w °2θ.

The reaction product obtainable by acidic catalysis from

Figure 11:
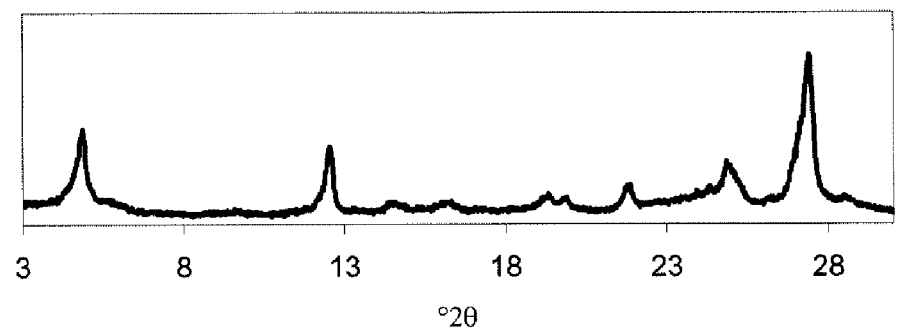
FIG. 11 represents an X-ray powder diagram of the product obtained in Example 14.

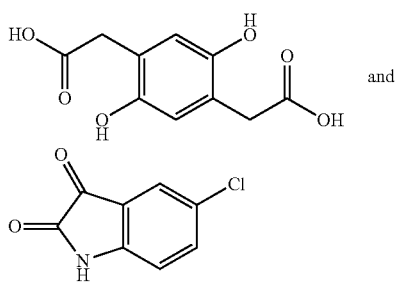
and in a molar ratio of 1:2, of empirical formula $C_{26}H_{10}N_2O_6Cl_2$, characterized by an X-ray powder diagram with lines at 4.8 m, 12.6 m, 21.8 w, 24.9 m and 27.4 s °2θ (FIG. 11). This crystal polymorph is obtained, for example, in toluene with p-toluene-sulphonic acid as catalyst, and is different from the crystal polymorph which is formed when the diisobutyl ester is used as a reactant (likewise in toluene).

The reaction product obtainable by acidic catalysis from

Figure 12:
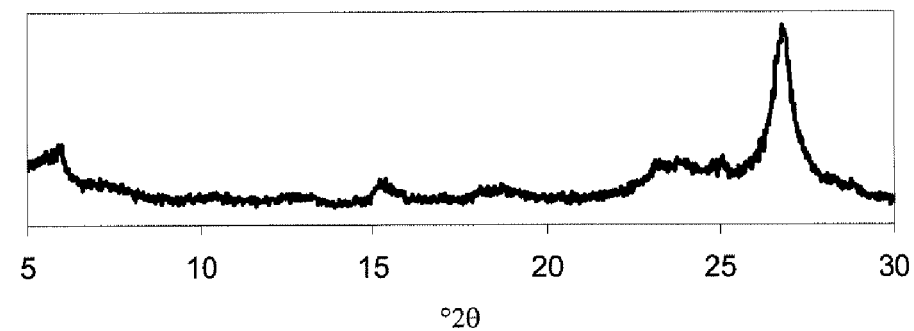
FIG. 12 represents an X-ray powder diagram of the product obtained in Example 15.

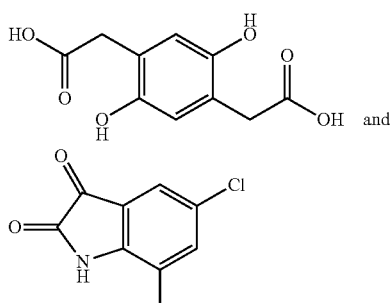
and in a molar ratio of 1:2, of empirical formula $C_{26}H_8N_2O_6Cl_4$, characterized by an X-ray powder diagram with lines at 5.9 w, 15.2 w, 23.9 w, 25.1 m and 26.8 s °2θ (FIG. 12). This crystal polymorph is obtained, for example, in toluene with p-toluene-sulphonic acid as catalyst.

The reaction product obtainable by acidic catalysis from

Figure 13:
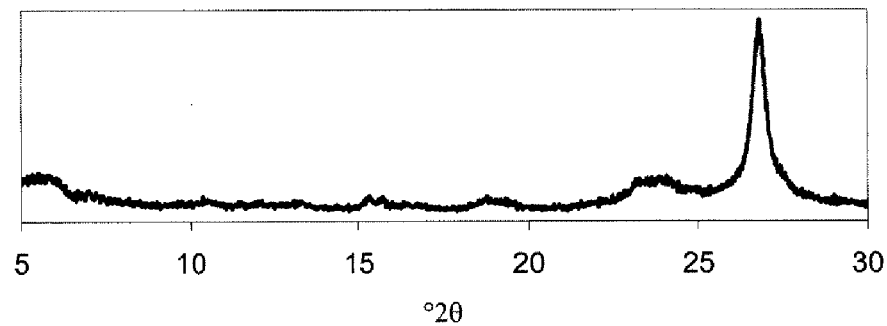
FIG. 13 represents an X-ray powder diagram of the product obtained in Example 16.

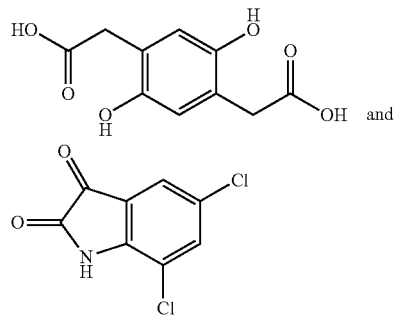
and in a molar ratio of 1:2, of empirical formula $C_{26}H_8N_2O_6Cl_4$, characterized by an X-ray powder diagram with lines at 23.9 w and 26.9 s °2θ (FIG. 13). This crystal polymorph is obtained, for example, in aqueous acetic acid (60-90% by weight) with p-toluenesulphonic acid as catalyst.

The reaction product obtainable by acidic catalysis from

Figure 14:
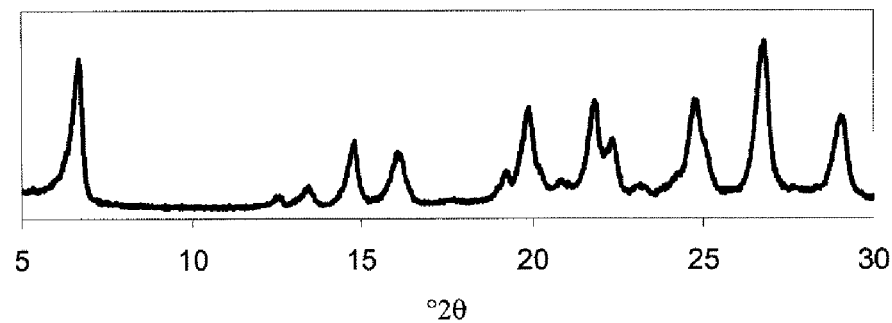
FIG. 14 represents an X-ray powder diagram of the product obtained in Example 17.

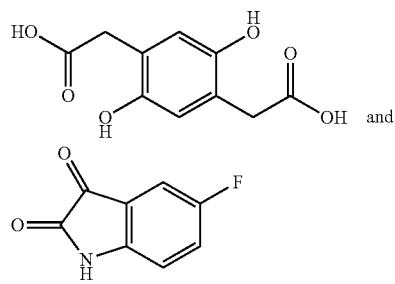
and in a molar ratio of 1:2, of empirical formula $C_{26}H_{10}N_2O_6F_2$, characterized by an X-ray powder diagram with lines at 6.7 s, 14.8 m, 16.1 m, 19.9 m, 21.8 m, 22.3 m, 24.8 m, 26.8 s and 29.1 m °2θ (FIG. 14). This crystal polymorph is obtained, for example, in toluene with p-toluenesulphonic acid as catalyst.

The reaction product obtainable by acidic catalysis from

Figure 15:
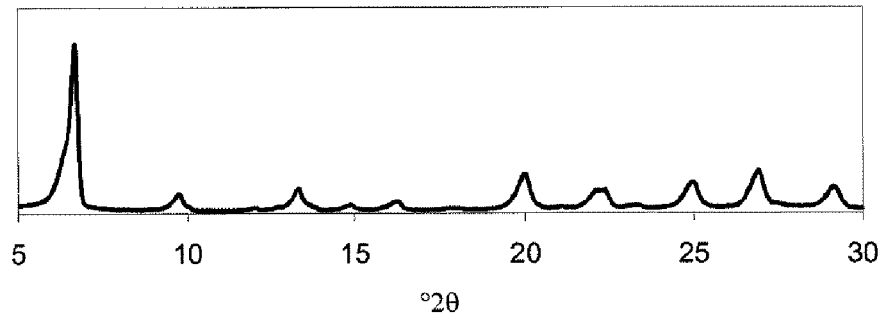
FIG. 15 represents an X-ray powder diagram of the product obtained in Example 18.

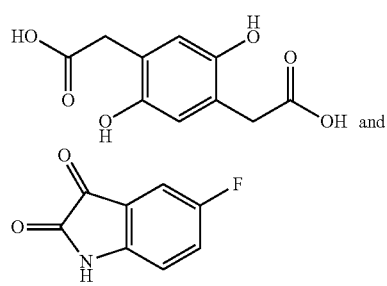
and in a molar ratio of 1:2, of empirical formula $C_{26}H_{10}N_2O_6F_2$, characterized by an X-ray powder diagram with lines at 6.7 s, 9.7 w, 13.3 w, 14.9 w, 16.3 w, 20.0 w, 22.3 w, 25.0 w, 26.9 w and 29.2 w °2θ (FIG. 15). At ~22.3 °2θ, a number of lines are poorly resolved. This crystal polymorph is obtained, for example, in aqueous acetic acid (60-90% by weight) with p-toluenesulphonic acid as catalyst.

The reaction product obtainable by acidic catalysis from

Figure 16:
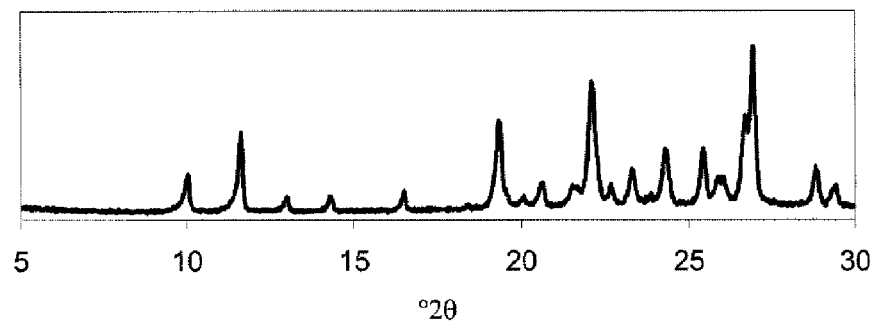
FIG. 16 represents an X-ray powder diagram of the product obtained in Example 19.

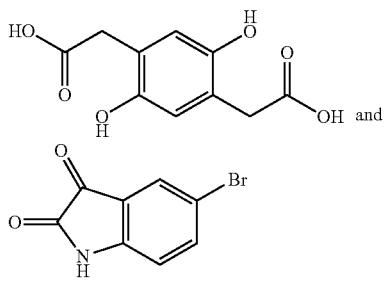

in a molar ratio of 1:2, of empirical formula $C_{26}H_{10}N_2O_6Br_2$, characterized by an X-ray powder diagram with lines at 10.0 w, 11.6 m, 19.3 m, 20.6 w, 22.1 s, 23.3 w, 24.3 m, 25.4 m, 26.0 w, 26.8 w, 26.9 s, 28.8 w and 31.3 w °2θ (FIG. 16). This crystal polymorph is obtained, for example, in chlorobenzene with p-toluenesulphonic acid as catalyst.

The reaction product obtainable by acidic catalysis from

Figure 17:
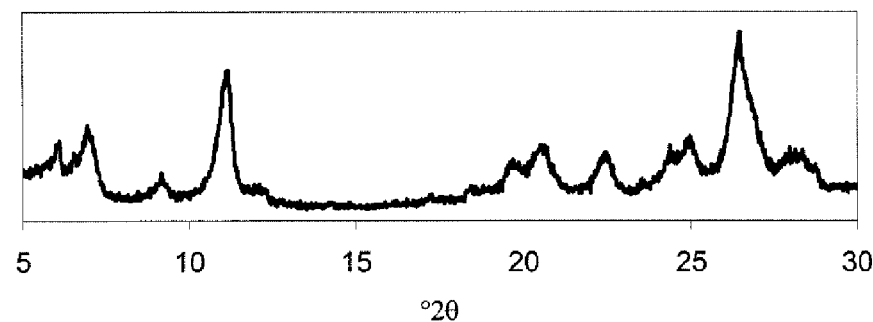
FIG. 17 represents an X-ray powder diagram of the product obtained in Example 20.

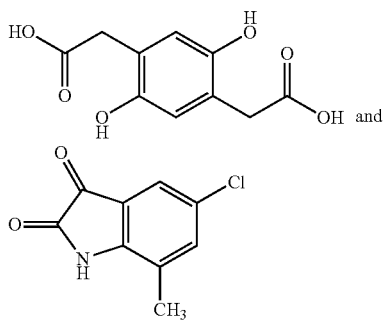

in a molar ratio of 1:2, of empirical formula $C_{28}H_{14}N_2O_6Cl_2$, characterized by an X-ray powder diagram with lines at 6.0 m, 7.0 m, 9.2 w, 11.1 s, 19.7 w, 20.6 m, 22.4 w, 25.0 m, 26.5 s and 28.3 w °2θ (FIG. 17). This crystal polymorph is obtained, for example, in toluene with p-toluenesulphonic acid as catalyst.

The reaction product obtainable by acidic catalysis from

Figure 18:
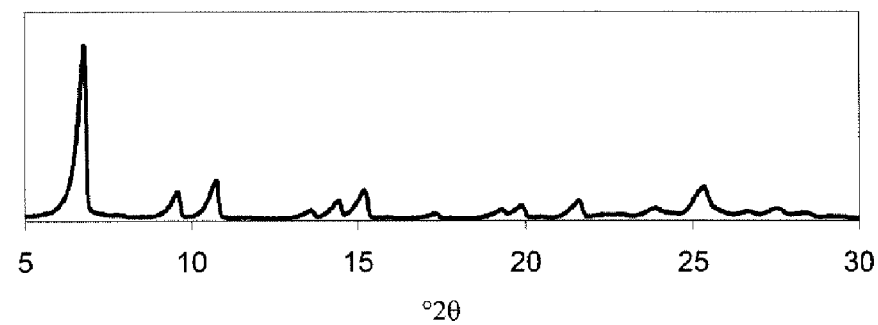
FIG. 18 represents an X-ray powder diagram of the product obtained in Example 21.

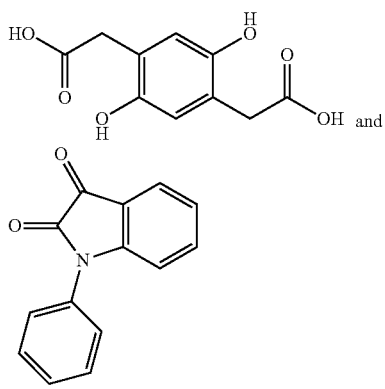

in a molar ratio of 1:2, of empirical formula $C_{38}H_{20}N_2O_6$, characterized by an X-ray powder diagram with lines at 6.7 s, 9.6 w, 10.7 w, 14.4 w, 15.2 w, 19.9 w, 21.6 w and 25.3 w °2θ (FIG. 18). This crystal polymorph is obtained, for example, in chlorobenzene with p-toluenesulphonic acid as catalyst.

The reaction product obtainable by acidic catalysis from

Figure 19:
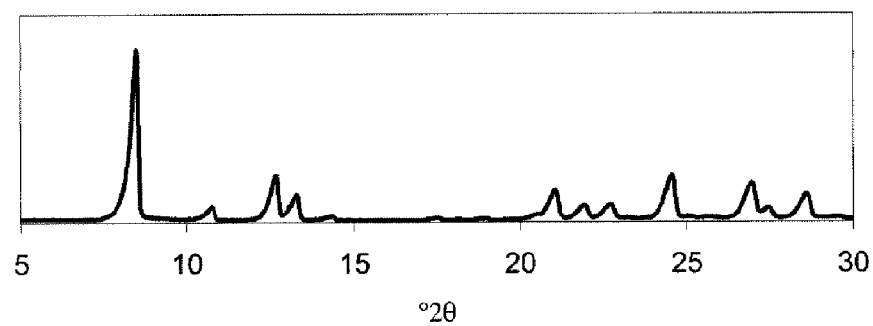
FIG. 19 represents an X-ray powder diagram of the product obtained in Example 22.

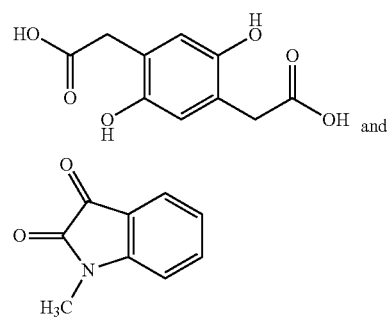

in a molar ratio of 1:2, of empirical formula $C_{28}H_{16}N_2O_6$, characterized by an X-ray powder diagram with lines at 8.5 s, 10.7 w, 12.6 w, 13.2 w, 21.0 w, 21.9 w, 22.7 w, 24.5 w, 26.9 w and 28.6 w °2θ (FIG. 19). This crystal polymorph is obtained, for example, in chlorobenzene with p-toluenesulphonic acid as catalyst.

The reaction product obtainable by acidic catalysis from

Figure 20:
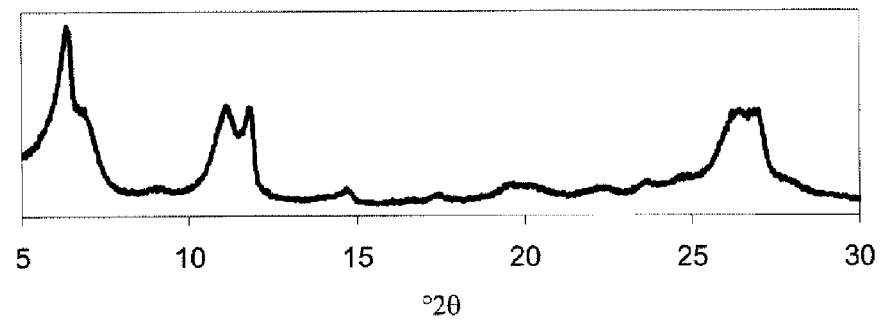
FIG. 20 represents an X-ray powder diagram of the product obtained in Example 23.

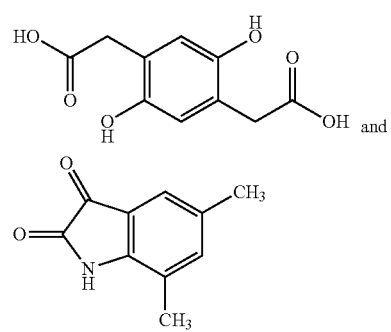

in a molar ratio of 1:2, of empirical formula $C_{30}H_{20}N_2O_6$, characterized by an X-ray powder diagram with lines at 6.4 s, 11.1 m, 11.8 m, 26.4 m and 26.9 m °2θ. At 6.9 and 26.2-27.0 °2θ, the lines are poorly resolved (FIG. 20). This probable mixture of the two preceding crystal polymorphs is obtained, for example, in toluene with p-toluene-sulphonic acid as catalyst.

The reaction product obtainable by acidic catalysis from

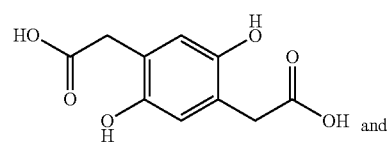

-continued

Figure 21:
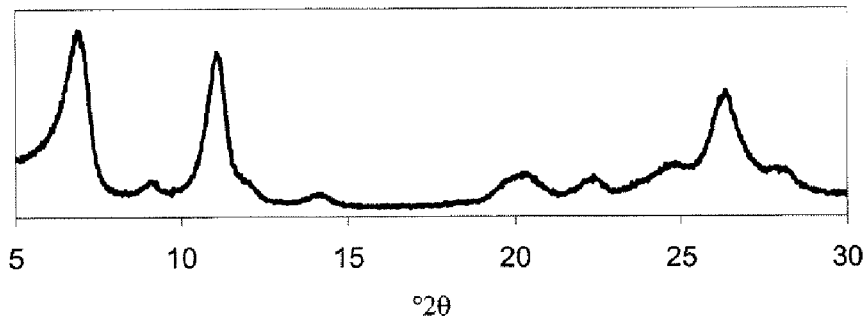
FIG. 21 represents an X-ray powder diagram of the product obtained in Example 24.

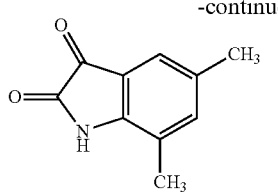

in a molar ratio of 1:2 in toluene with p-toluenesulphonic acid, followed by recrystallization from glacial acetic acid or N-methylpyrrolidone, of empirical formula $C_{30}H_{20}N_2O_6$, characterized by an X-ray powder diagram with lines at 6.9 s, 9.2 w, 11.1 s, 14.2 w, 20.3 w, 22.4 w and 26.3 m °2θ (FIG. 21).

The reaction product obtainable by acidic catalysis from

Figure 22:
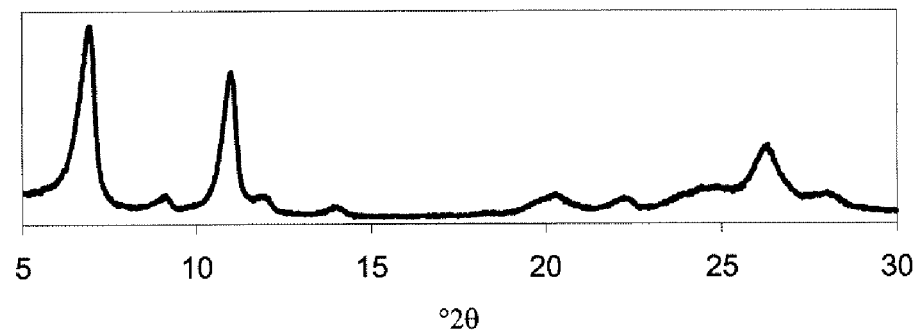
FIG. 22 represents an X-ray powder diagram of the product obtained in Example 25.

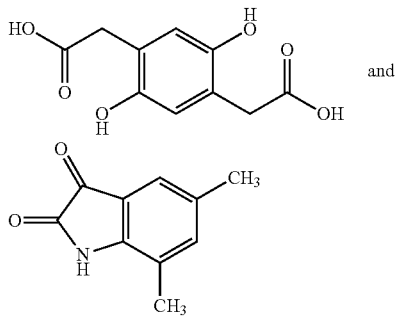

in a molar ratio of 1:2, of empirical formula $C_{30}H_{20}N_2O_6$, characterized by an X-ray powder diagram with lines at 6.9 s, 11.0 s, 20.3 w and 26.3 m °2θ (FIG. 22). This crystal polymorph is obtained, for example, in aqueous acetic acid (60-90% by weight) with p-toluenesulphonic acid as catalyst, and appears to contain a trace of the preceding crystal polymorph.

The reaction product obtainable by acidic catalysis from

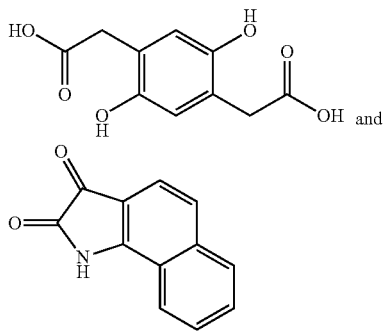

in a molar ratio of 1:2, of empirical formula $C_{34}H_{16}N_2O_6$, characterized by a mass spectrum with molecular ion m/z 548.1 (MALDI). This crystal polymorph is obtained, for example, in aqueous acetic acid (60-90% by weight) with p-toluenesulphonic acid as catalyst.

The reaction product obtainable by acidic catalysis from

Figure 23:
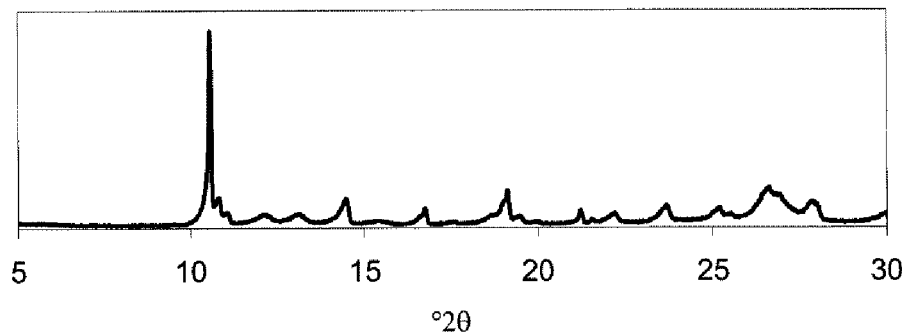
FIG. 23 represents an X-ray powder diagram of the product obtained in Example 27.

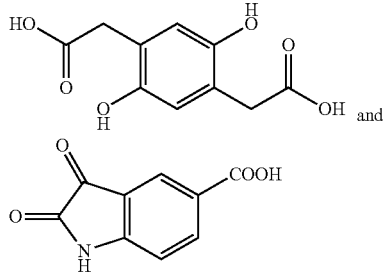

in a molar ratio of 1:2 with p-toluenesulphonic acid, of empirical formula $C_{30}H_{16}N_2O_{10}$, characterized by an X-ray powder diagram with lines at 10.6 s, 14.4 w, 16.7 w, 19.1 w, 23.7 w, 25.2 w, 26.6 w and 27.9 w °2θ (FIG. 23). This crystal polymorph is obtained, for example, in toluene with p-toluenesulphonic acid as catalyst.

The reaction product obtainable by acidic catalysis from

Figure 24:
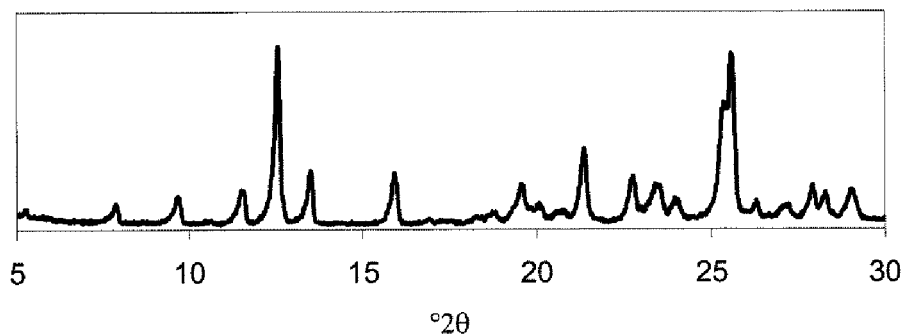
FIG. 24 represents an X-ray powder diagram of the product obtained in Example 28.

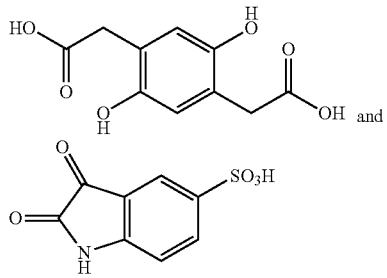

in a molar ratio of 1:2 with p-toluenesulphonic acid, of empirical formula $C_{28}H_{16}N_2O_{12}S_2$, characterized by an X-ray powder diagram with lines at 7.9 w, 9.7 w, 11.5 w, 12.6 s, 13.5 w, 15.9 w, 19.6 w, 21.4 m, 22.8 w, 23.5 w, 24.0 w, 25.4 m, 25.6 s, 27.9 w, 28.3 w, 29.1 w and 30.7 w °2θ (FIG. 24). This crystal polymorph is obtained, for example, in aqueous acetic acid (60-90% by weight) with p-toluenesulphonic acid as catalyst.

Lines with a weak relative intensity (<33⅓%=w) are not always characteristic and may sometimes vary in intensity or be entirely absent, depending on crystal form, sample preparation and recording method or degree of purity. In order to ascertain the identity of samples, therefore, it is usually sufficient to compare the lines of medium or strong relative intensity (33⅓-66⅔%=m or 66⅔-100%=s). The reported absolute values of the gloss numbers, obtainable by means of customary, routine measurements, may carry an inaccuracy of up to around ±0.2 °2θ, depending on sample preparation and on measuring conditions, and the scale of the spectra, relative to the absolute values, may not only be slightly shifted but also be narrowed or stretched in its extent. The line width reflects the crystallite size and the degree of crystallinity.

A suitable instrument is, for example, a Siemens D500/501 diffractometer. It is advantageous to produce a tablet in customary manner, as disclosed for example in U.S. Geological Survey Open-File Report 01-041/A Laboratory Manual for X-Ray Powder Diffraction/Randomly Oriented Powder Mounts For X-Ray Powder Diffraction (http://pubs.usgs.gov/of/2001/of01-041/htmldocs/methods/romount.htm).

Usually these crystal polymorphs are present preferably in substantially single-phase form. By this is meant that other crystal polymorphs are present in an amount of less than 20% by weight, preferably less than 10% by weight, based on the total amount of all crystal polymorphs. The relative amounts of different crystal polymorphs in a sample can be estimated from the areas of the most intense different lines, following subtraction of the baseline first. Alternatively the X-ray powder diagram can be compared with X-ray powder diagrams of physical mixtures of known composition.

If an aqueous reaction medium is used, for example a reaction medium containing from 5% to 50% by weight of water, based on the amount of water-free reaction medium, then the crystal polymorphs obtained are generally different from those obtained when an anhydrous reaction medium is used, such as toluene or glacial acetic acid. The crystal polymorphs obtainable in the presence of water are notable, especially in polyolefins, for good light fastness, better dispersibility and outstandingly jet-black shades in the masstone, and also useful, somewhat greenish grey shades when reduced with titanium oxide. Moreover, they can, with particular advantage, be converted into even more stable crystal polymorphs by means of recrystallization from polar solvents.

The crystal polymorphs that are obtainable in anhydrous reaction media, in contrast, are notable in particular for higher light fastness in varnishes (particularly in polyester/cellulose acetobutyrate varnishes). When reduced with titanium oxide, they typically produce outstandingly neutral grey shades.

Surprisingly it is also possible in accordance with the process of the invention to prepare solid solutions and mixed crystals by reacting a compound of the formula

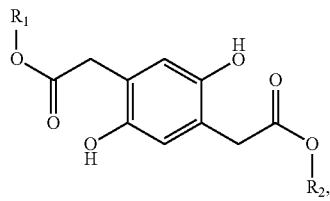

preferably of the formula

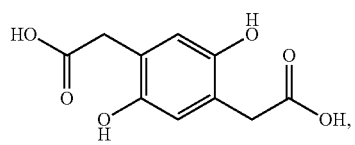

with two or more compounds of the formula

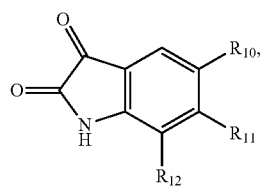

in an overall molar ratio (i):(iv) of 1:2, in the presence of an acidic catalyst which in water at 25° C. has a pK≤4.5. In this case, either polyphase or single-phase pigments may be obtained, the latter being preferred. Suitability for forming solid solutions and mixed crystals, however, is possessed only by isatin and certain substituted isatins of the formula

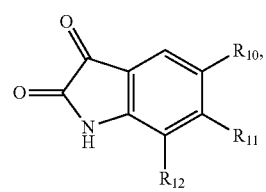

and, in addition, a defined amount of the main component must be maintained.

The invention therefore also provides a process for preparing a black colorant, characterized in that a compound of the formula

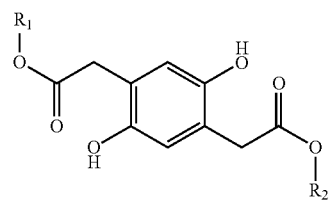

is reacted with 2 to 5 compounds of the formula

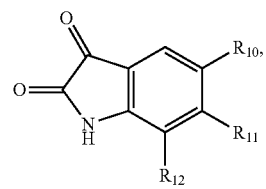

in which $R_{10}$ is H, $CH_3$, $C_2H_5$, $OCH_3$, $OC_2H_5$, F, Cl, Br, $NO_2$, CN, COOH or $SO_3H$, $R_{11}$ is H, $NO_2$, CN, COOH or $SO_3H$, and $R_{12}$ is H, $CH_3$, $C_2H_5$, $OCH_3$, $OC_2H_5$, F, or Cl, in an overall molar ratio (i):(iv) of 1:2 in the presence of a catalyst which in water at 25° C. has a pK≤4.5, the amount of one of the compounds of the formula (iv) being from 50% to 80% by weight, based on the total amount of all compounds of the formula (iv).

Preferably $R_{10}$ is H, $CH_3$, $OCH_3$, F, Cl, Br, $NO_2$ or $SO_3H$, $R_{11}$ is H or $SO_3H$, and $R_{12}$ is H, $CH_3$ or Cl. With particular preference $R_{10}$ is H, $CH_3$ or $C_1$, $R_{11}$ is H, and $R_{12}$ is H, $CH_3$ or Cl. Very particular preference is given to the compounds of the formula (iv), in which $R_{10}=R_{11}=R_{12}=H$, $R_{10}=CH_3/R_{11}=R_{12}=H$, $R_{10}=Cl/R_{11}=R_{12}=H$, $R_{10}=OCH_3/R_{11}=R_{12}=H$, $R_{10}=NO_2/R_{11}=R_{12}=H$, $R_{11}=H/R_{10}=R_{12}=CH_3$ or $R_{11}=H/R_{10}=R_{12}=Cl$.

The compounds (i) and (iv) for reaction, preferably (iii) and (iv), may all be included in the initial charge or may be added simultaneously or in any order. Where not all of the compounds (iv) are included in the initial charge, it is generally favourable to maintain the final ratio indicated above for the compounds of the formula (iv) throughout the reaction. Thus, for example, the reaction may begin with a mixture of two compounds of the formula (iv) in a weight ratio of 50:50, to produce a particular crystal polymorph, and may then be continued with a weight ratio of 80:20, in which case the crystal polymorph no longer undergoes any change.

Surprisingly, in many cases, depending on the reaction medium, crystal polymorphs are formed which differ significantly from the crystal phases of the products that are formed when only a single one of the same compounds of the formula (iv) is reacted. In other words, advantageously, new, more stable crystal polymorphs are formed, preferably single-phase crystal polymorphs or single-phase mixed crystals, whose crystal lattice is able to serve as a host for guest molecules which are possibly stoichiometrically superfluous in the ideal single-phase crystal lattice.

As a main component of the formula (iv), the compound of the formula

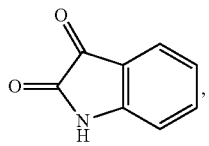

and as a secondary component of the formula (iv), a compound of the formula

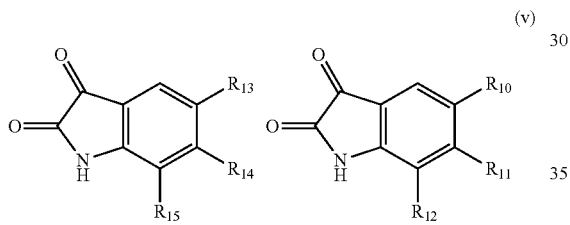

(v)

are preferably reacted with the compound of the formula (i), where $R_{13}$ is H, $C_1$-$C_8$alkyl, $OC_1$-$C_8$alkoxy, F, Cl, Br, $NO_2$, CN, COOH or $SO_3H$, $R_{14}$ is H, $NO_2$, CN, COOH or $SO_3H$, and $R_{15}$ is H, Cl or $C_1$-$C_8$alkyl.

With particular preference $R_{13}$ is H or $C_1$-$C_4$alkyl, $R_{14}$ is H, and $R_{15}$ is H, Cl or $C_1$-$C_8$alkyl.

The mixed crystals and solid solutions of the invention are notable especially for high dispersibility, high colour strength, advantageous black shades and high fastnesses (in particular, better weather fastness). They are particularly advantageous in paint applications (especially in polyester/cellulose acetobutyrate varnishes).

The invention accordingly also provides the following crystal polymorphs (°2θ/CuK$_\alpha$; the lines in the X-ray powder diagrams are identified, in addition to the gloss number, in accordance with their relative intensity: <33⅓%=w, 33⅓-66⅔%=m or 66⅔-100%=s; very weak, broad lines and humps are generally not included):

The reaction product obtainable by acidic catalysis from

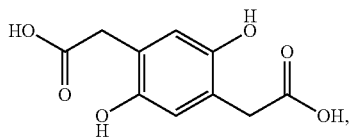

Figure 25:
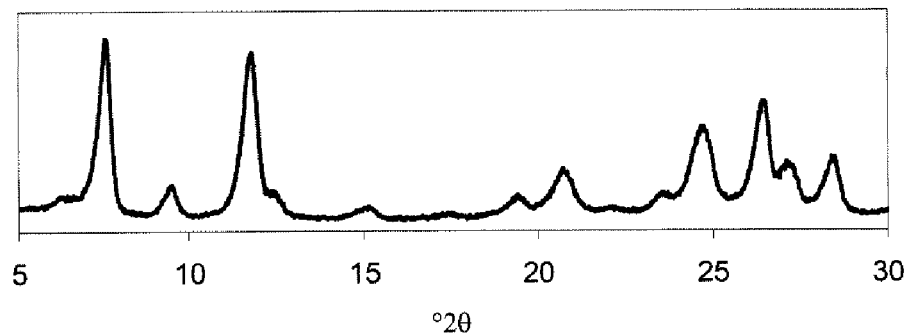
FIG. 25 represents an X-ray powder diagram of the product obtained in Example 29.

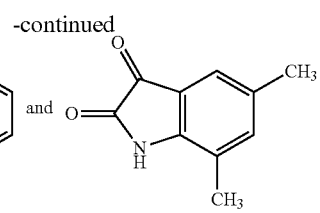

in a molar ratio of 1:1:1, comprising compounds of empirical formulae $C_{26}H_{12}N_2O_6$, $C_{28}H_{16}N_2O_6$ and $C_{30}H_{20}N_2O_6$, characterized by an X-ray powder diagram with lines at 7.6 s, 9.5 w, 11.8 s, 20.7 w, 24.7 m, 26.4 m and 28.4 m °2θ (FIG. 25). This crystal polymorph is different from those of the pure compounds of empirical formulae $C_{26}H_{12}N_2O_6$ and $C_{30}H_{20}N_2O_6$, and is obtained, for example, in toluene, chlorobenzene or glacial acetic acid with p-toluenesulphonic acid as catalyst.

The reaction product obtainable by acidic catalysis from

Figure 26:
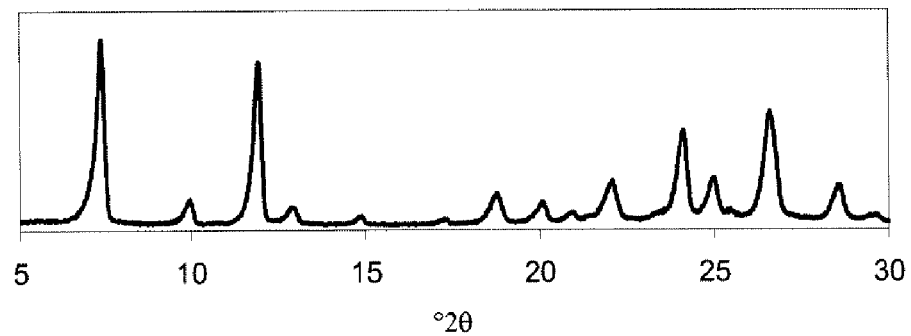
FIG. 26 represents an X-ray powder diagram of the product obtained in Example 30.

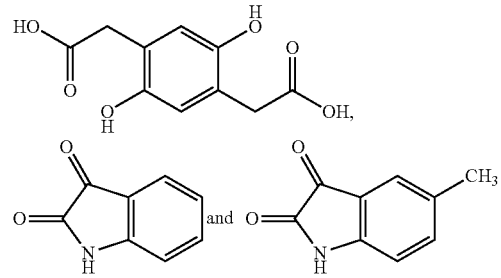

in a molar ratio of 1:1:1, comprising compounds of empirical formulae $C_{26}H_{12}N_2O_6$, $C_{27}H_{14}N_2O_6$ and $C_{28}H_{16}N_2O_6$, characterized by an X-ray powder diagram with lines at 7.4 s, 10.0 w, 11.9 s, 18.8 w, 20.1 w, 22.1 w, 24.1 m, 25.0 w, 26.6 m and 28.6 w °2θ (FIG. 26). This crystal polymorph is different from those of the pure compounds of empirical formulae $C_{26}H_{12}N_2O_6$ and $C_{28}H_{16}N_2O_6$, and corresponds essentially to that of the pure compound of empirical formula $C_{28}H_{16}N_2O_6$ (FIG. 4). It is obtained, for example, in chlorobenzene with p-toluene-sulphonic acid as catalyst.

The reaction product obtainable by acidic catalysis from

Figure 27:
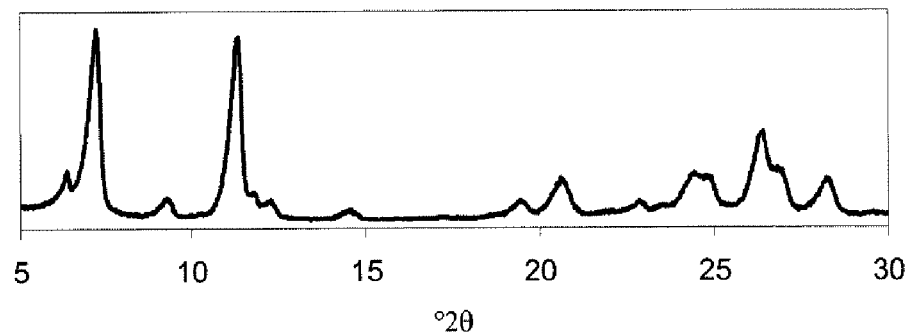
FIG. 27 represents an X-ray powder diagram of the product obtained in Example 32.

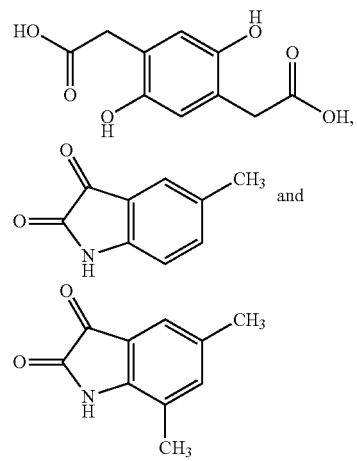

in a molar ratio of 1:1:1, comprising compounds of empirical formulae $C_{28}H_{16}N_2O_6$, $C_{29}H_{18}N_2O_6$ and $C_{30}H_{20}N_2O_6$, characterized by an X-ray powder diagram with lines at 7.2 s, 9.3 w, 11.3 s, 19.4 w, 20.6 w, 24.5 w, 26.4 m, 26.9 w and 28.3 w °2θ (FIG. 27). This crystal polymorph is different from those of the pure compounds of empirical formulae $C_{28}H_{16}N_2O_6$ and $C_{30}H_{20}N_2O_6$ and is obtained, for example, in toluene with p-toluenesulphonic acid as catalyst. It is also different to the crystal polymorph of the product of the same composition which is obtained in glacial acetic acid.

The reaction product obtainable by acidic catalysis from

Figure 28:
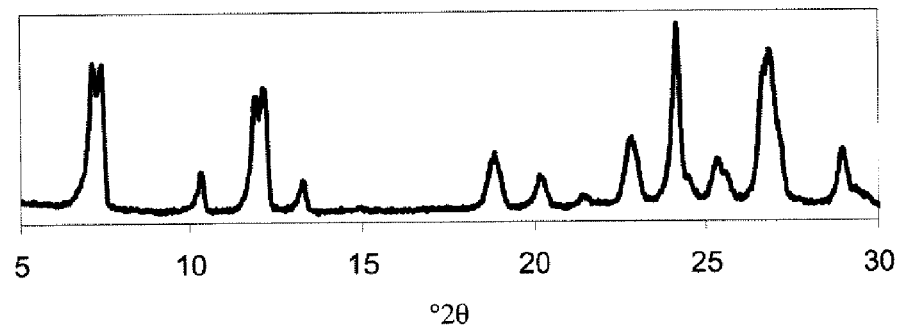
FIG. 28 represents an X-ray powder diagram of the product obtained in Example 33.

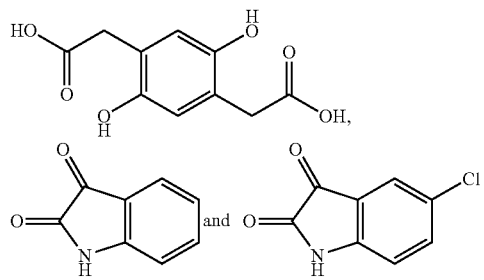

in a molar ratio of 1:1:1, comprising compounds of empirical formulae $C_{26}H_{12}N_2O_6$, $C_{26}H_{11}N_2O_6Cl$ and $C_{26}H_{10}N_2O_6Cl_2$, characterized by an X-ray powder diagram with lines at 7.2 s, 7.4 s, 10.3 w, 11.9 m, 12.2 s, 13.3 w, 18.9 w, 20.2 w, 22.8 m, 24.1 s, 25.3 w, 26.8 s and 29.0 m °2θ (FIG. 28). This crystal polymorph is different from those of the pure compounds of empirical formulae $C_{28}H_{16}N_2O_6$ and $C_{26}H_{10}N_2O_6Cl_2$ and is obtained, for example, in toluene with p-toluenesulphonic acid as catalyst.

The reaction product obtainable by acidic catalysis from

Figure 29:
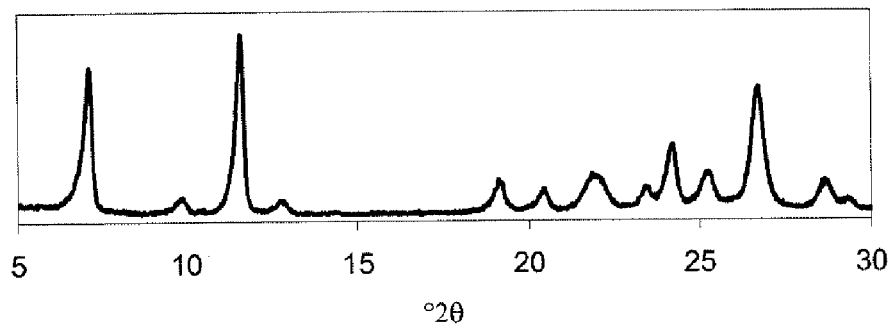
FIG. 29 represents an X-ray powder diagram of the product obtained in Example 34.

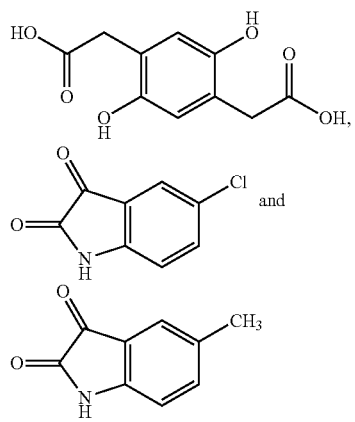

in a molar ratio of 1:1:1, comprising compounds of empirical formulae $C_{26}H_{10}N_2O_6Cl_2$, $C_{27}H_{13}N_2O_6C_1$ and $C_{28}H_{16}N_2O_6$, characterized by an X-ray powder diagram with lines at 7.1 s, 11.6 s, 19.2 w, 20.4 w, 21.9 w, 24.2 m, 25.2 w, 26.7 s and 28.7 w °2θ (FIG. 29). This crystal polymorph is different from those of the pure compounds of empirical formulae $C_{26}H_{10}N_2O_6Cl_2$ and $C_{28}H_{16}N_2O_6$ and is obtained, for example, in toluene with p-toluenesulphonic acid as catalyst.

The reaction product obtainable by acidic catalysis from

Figure 30:
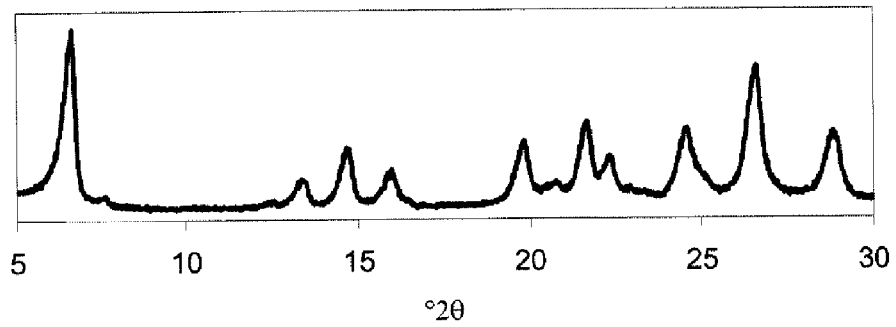
FIG. 30 represents an X-ray powder diagram of the product obtained in Example 35.

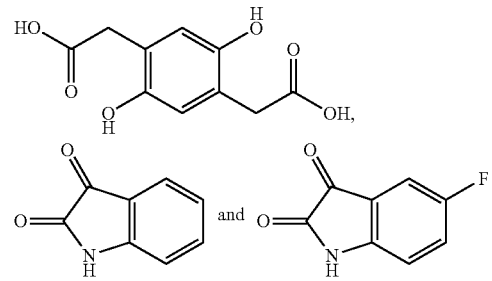

in a molar ratio of 1:1:1, comprising compounds of empirical formulae $C_{26}H_{12}N_2O_6$, $C_{26}H_{11}N_2O_6F$ and $C_{26}H_{10}N_2O_6F_2$, characterized by an X-ray powder diagram with lines at 6.6 s, 13.5 w, 14.7 m, 15.9 w, 19.8 m, 21.6 m, 22.3 w, 24.6 m, 26.6 s and 28.8 m °2θ (FIG. 30). This crystal polymorph is different from those of the pure compounds of empirical formulae $C_{26}H_{12}N_2O_6$ and $C_{26}H_{10}N_2O_6F_2$ and is obtained, for example, in chlorobenzene with p-toluenesulphonic acid as catalyst.

The reaction product obtainable by acidic catalysis from

Figure 31:
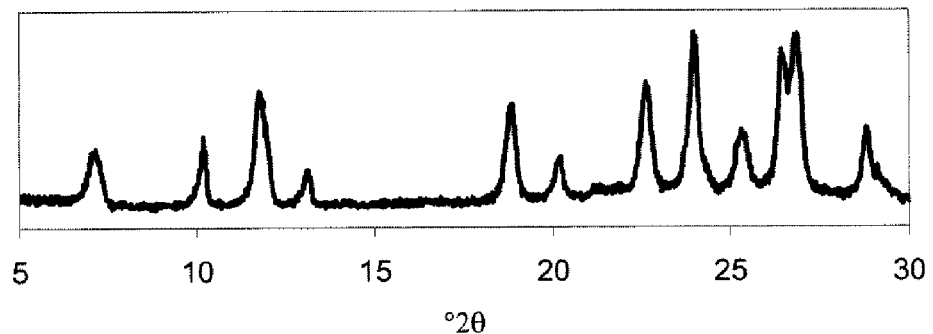
FIG. 31 represents an X-ray powder diagram of the product obtained in Example 36.

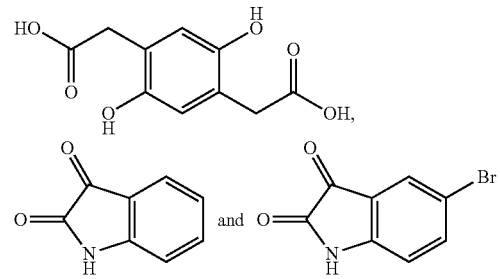

in a molar ratio of 1:1:1, comprising compounds of empirical formulae $C_{26}H_{12}N_2O_6$, $C_{26}H_{11}N_2O_6Br$ and $C_{26}H_{10}N_2O_6Br_2$, characterized by an X-ray powder diagram with lines at 7.1 m, 10.2 m, 11.8 s, 13.1 w, 18.8 m, 20.2 m, 22.7 s, 24.0 s, 25.3 m, 26.5 s, 26.8 s and 28.8 m °2θ (FIG. 31). This crystal polymorph is different from those of the pure compounds of empirical formulae $C_{26}H_{12}N_2O_6$ and $C_{26}H_{10}N_2O_6Br_2$ and is obtained, for example, in chlorobenzene with p-toluenesulphonic acid as catalyst.

The reaction product obtainable by acidic catalysis from

Figure 32:
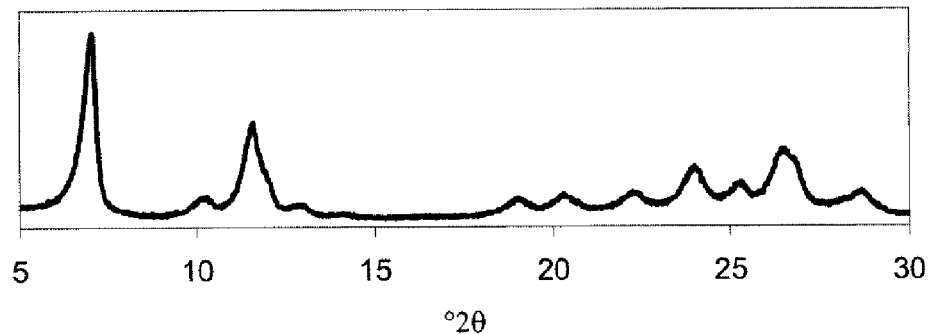
FIG. 32 represents an X-ray powder diagram of the product obtained in Example 37.

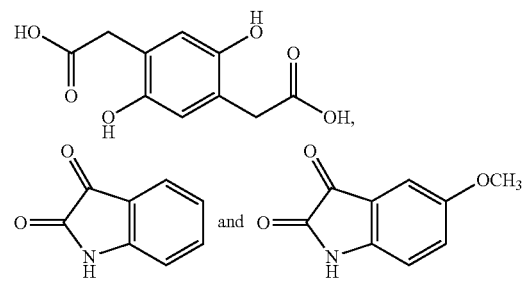

in a molar ratio of 1:1:1, comprising compounds of empirical formulae $C_{26}H_{12}N_2O_6$, $C_{27}H_{14}N_2O_7$ and $C_{28}H_{16}N_2O_8$, characterized by an X-ray powder diagram with lines at 7.0 s, 10.4 w, 11.6 m, 19.0 w, 20.3 w, 22.3 w, 24.0 w, 25.3 w, 26.5 m and 28.7 w °2θ (FIG. 32).

This crystal polymorph is different from those of the pure compounds of empirical formulae $C_{26}H_{12}N_2O_6$ and $C_{28}H_{16}N_2O_8$ and is obtained, for example, in chlorobenzene with p-toluenesulphonic acid as catalyst.

The reaction product obtainable by acidic catalysis from

Figure 33:
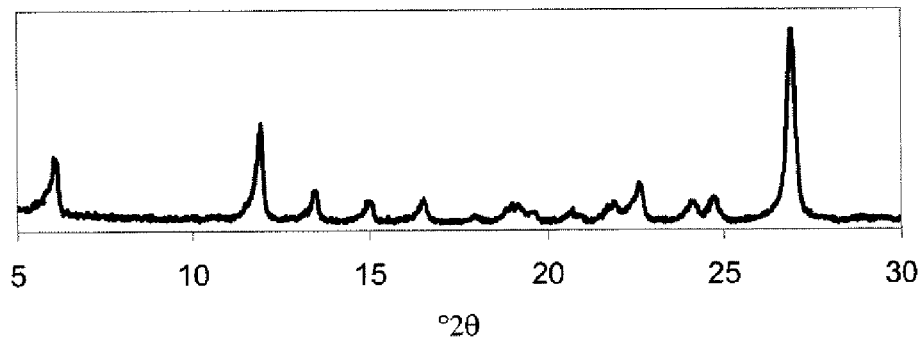
FIG. 33 represents an X-ray powder diagram of the product obtained in Example 38.

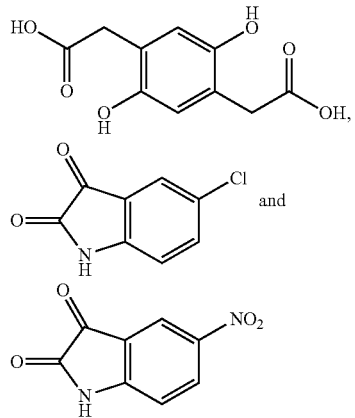

in a molar ratio of 1:1:1, comprising compounds of empirical formulae $C_{26}H_{10}N_2O_6Cl_2$, $C_{26}H_{10}N_3O_8Cl$ and $C_{26}H_{10}N_4O_{10}$, characterized by an X-ray powder diagram with lines at 6.1 m, 11.9 m, 13.5 w, 15.0 w, 16.5 w, 22.6 w, 24.1 w, 24.7 w and 26.9 s °2θ (FIG. 33). This crystal polymorph is different from those of the pure compounds of empirical formulae $C_{26}H_{10}N_2O_6Cl_2$ and $C_{26}H_{10}N_4O_{10}$ and is obtained, for example, in toluene with p-toluene-sulphonic acid as catalyst.

The reaction product obtainable by acidic catalysis from

Figure 34:
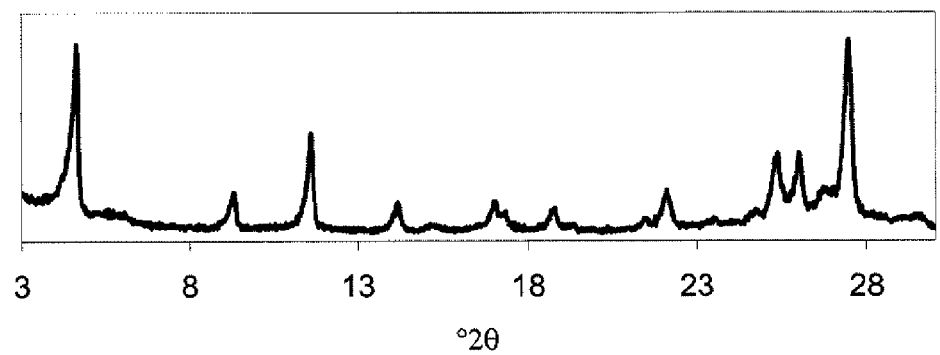
FIG. 34 represents an X-ray powder diagram of the product obtained in Example 39.

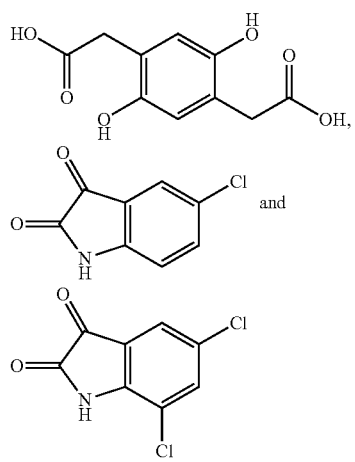

in a molar ratio of 1:1:1, comprising compounds of empirical formulae $C_{26}H_{10}N_2O_6Cl_2$, $C_{26}H_9N_2O_6Cl_3$ and $C_{26}H_8N_2O_6Cl_4$, characterized by an X-ray powder diagram with lines at 4.6 s, 9.3 w, 11.6 m, 14.2 w, 17.1 w, 18.8 w, 22.1 w, 25.4 m, 26.0 m and 27.5 s °2θ (FIG. 34). This crystal polymorph is different from those of the pure compounds of empirical formulae $C_{26}H_{10}N_2O_6Cl_2$ and $C_{26}H_8N_2O_6Cl_4$ and is obtained, for example, in toluene with p-toluene-sulphonic acid as catalyst.

The reaction product obtainable by acidic catalysis from

Figure 35:
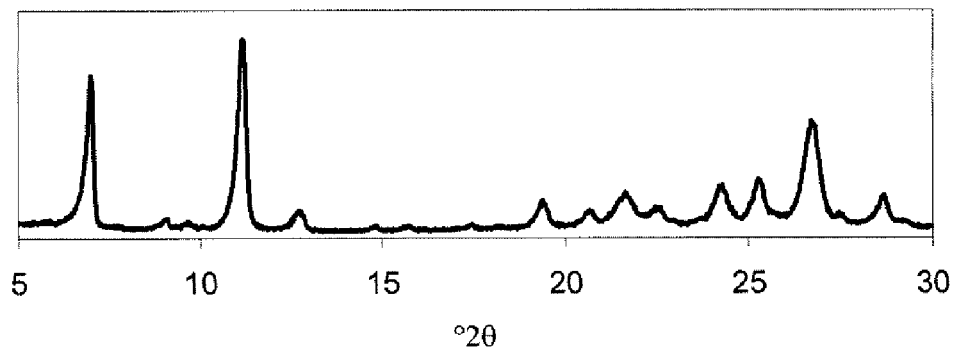
FIG. 35 represents an X-ray powder diagram of the product obtained in Example 40.

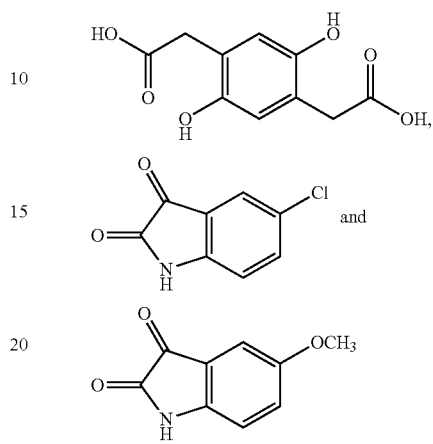

in a molar ratio of 1:1:1, comprising compounds of empirical formulae $C_{26}H_{10}N_2O_6Cl_2$, $C_{27}H_{13}N_2O_7Cl$ and $C_{28}H_{16}N_2O_8$, characterized by an X-ray powder diagram with lines at 7.0 s, 11.2 s, 12.7 w, 19.4 w, 20.7 w, 21.6 w, 22.5 w, 24.3 w, 25.3 w, 26.8 m and 28.7 w °2θ (FIG. 35). This crystal polymorph is different from those of the pure compounds of empirical formulae $C_{26}H_{10}N_2O_6Cl_2$ and $C_{28}H_{16}N_2O_8$ and is obtained, for example, in toluene with p-toluenesulphonic acid as catalyst.

If the preparation of true mixed crystals and solid solutions is not desired (for reasons of cost, for example), then it is also possible to increase the amount of main component of the formula (iv). In this case the secondary components of the formula (iv), at a concentration, for example, of 0.1% to 15% by weight, preferably of 0.5% to 12% by weight, based on the total amount of all compounds of the formula (iv), may advantageously inhibit crystal growth or bring about the target crystal polymorph.

Since it is irrelevant here whether solid solutions are produced, there is no restriction on the selection of secondary components for use as crystal growth inhibitors or crystal polymorph effectors. Alternatively to the simultaneous addition, of course, it is also possible first to react a portion of the compound of the formula (i) with a portion or the entirety of secondary component of the formula (iv), in an overall molar ratio of 1:2, and then to continue the reaction with the remainder of compound of the formula (i), of main component of the formula (iv) and, where present, the remainder of secondary component of the formula (iv), or it is possible first to react a portion of compound of formula (i) with a portion or the entirety of the main component of the formula (iv), in an overall molar ratio of 1:2, and then to continue the reaction with the remainder of compound of the formula (i), of secondary component of the formula (iv) and, where present, the remainder of main component of the formula (iv).

The invention therefore also provides a process for preparing a black colorant, characterized in that a compound of the formula

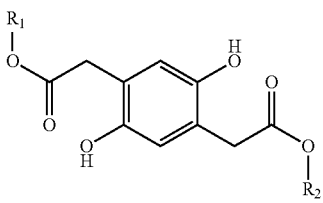

is reacted with 2 to 5 compounds of the formula

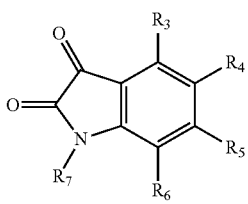

in an overall molar ratio (i):(ii) of 1:2 in the presence of a catalyst which in water at 25° C. has a pK≤4.5, the amount of one of the compounds of the formula (ii) being from 85% to 99.9% by weight, based on the total amount of all compounds of the formula (ii), and the compounds of the formula

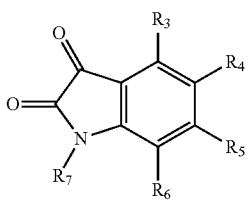

being added simultaneously or in any order before or during the reaction.

The invention, moreover, also provides a black colorant composition comprising the reaction products of a compound of the formula

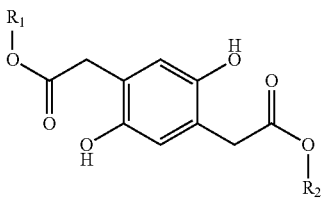

with a compound of the formula

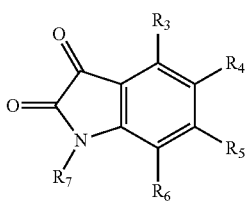

and 1 to 4 further compounds of the formula

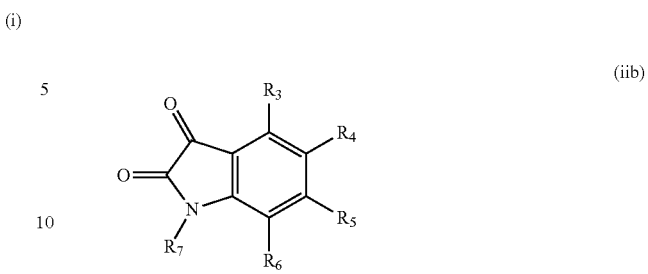

in an overall molar ratio (i):(ii) of 1:2 in the presence of a catalyst which in water at 25° C. has a pK≤4.5, the amount of the compound of the formula (iia) being from 85% to 99.9% by weight, based on the total amount of the compounds of the formulae (iia) and (iib), and $R_3$, $R_4$, $R_5$, $R_6$ and $R_7$ in the formulae (iia) and (iib) having, independently of one another, the same definition as in formula (ii) above. Of course, the compounds of the formula (iia) and all other compounds of the formula (iib) are different.

The compound of the formula (iia) is preferably unsubstituted isatin or 5-methylisatin, more preferably unsubstituted isatin.

In formulae (iia) and (iib), preferably one of the radicals $R_3$, $R_4$, $R_5$, $R_6$ or $R_7$, preferably $R_4$, is $C_1$-$C_{16}$alkyl, $C_1$-$C_{16}$alkoxy, $C_3$-$C_{16}$cycloalkyl, $C_3$-$C_{16}$cycloalkoxy, $C_2$-$C_{16}$alkenyl or $C_2$-$C_{16}$alkenoxy, more preferably $C_3$-$C_{12}$alkyl, $C_5$-$C_6$cycloalkyl, $C_3$-$C_{12}$alkoxy or $C_5$-$C_6$cycloalkoxy, very preferably $C_4$-$C_8$alkyl or $C_4$-$C_8$alkoxy, more particularly n-butyl, isobutyl, tert-butyl, 3-pentyl, n-hexyl, cyclohexyl, 2-ethylhexyl, n-octyl, lauryl or myristyl, and the other four of the radicals $R_3$, $R_4$, $R_5$, $R_6$ or $R_7$ are each H.

The pigments of the invention, modified by added components, are notable especially for high colour strength, advantageous jet-black shades and high fastnesses. They are advantageous in particular in paint applications and in the mass colouring of plastics.

It is of course also possible for all colorants, colorant mixtures, mixed crystals and solid solutions obtainable in accordance with the invention to undergo further chemical modification after their preparation, examples of such modification including sulphonation, reduction of nitro to amino groups, esterification or neutralization of acid groups to form salts. These modified black compounds may be used as colorants or pigments in the same way as their starting materials. Preference is given here to sulphonation, chlorosulphonation, the neutralization of carboxyl and sulpho groups, and the formation of amides from $SO_2Cl$ groups. Carboxyl and sulpho groups are advantageously converted into $COO^-$ and $SO_3^-$ groups with bases, more particularly strong bases. Examples of suitable bases include alkali metal and alkaline earth metal hydroxides, oxides or amides, aluminium oxide, ammonia, primary, secondary, tertiary or quaternary amines. Preference is given to alkaline earth metal hydroxides and quaternary amines. Primary, secondary, tertiary or quaternary amines are preferably substituted on the N by $C_1$-$C_{30}$alkyl, $C_2$-$C_{30}$alkenyl, $C_2$-$C_{30}$alkynyl, $C_7$-$C_{30}$aralkyl or $C_6$-$C_{30}$aryl, it being possible for these hydrocarbon substituents to be linear or branched, uninterrupted or interrupted one or more times by carbonyl, —O—, —S— and/or

and/or unsubstituted or substituted one or more times by halogen, hydroxyl, amino, carboxyl or sulpho. The colorants which have undergone further chemical modification likewise have pitch-black shades and are of interest more particularly for applications in which a relatively low surface polarity is required.

Surprisingly it has emerged that the colorants obtainable in accordance with the invention, in combination with basic additives, such as hindered amines (HALS) and/or UV absorbers of benzotriazole or triazine type, lead to jet-black paints and plastics in which the weather stability of the matrix material is increased in comparison with known black pigments such as carbon black.

The invention accordingly also provides for the use of a colorant of the invention for coloring a high molecular weight material in the mass, and also a mass-coloured, high molecular weight material containing from 0.01% to 70% by weight, preferably from 0.05% to 30% by weight, of a colorant of the invention, and from 0.01% to 20% by weight, preferably from 0.1% to 10% by weight, more preferably from 0.2% to 5%, of a basic light stabilizer or of a mixture of basic light stabilizers, based in each case on the total coloured, high molecular weight material.

Advantageous light stabilizers are those which lead to an increase in light stability by at least 50% at a concentration of 1.0% by weight, based on the total coloured, high molecular weight material. This means that the time until, in an accelerated light stability test, there is a significant change in surface structure or in mechanical properties, in the presence of 1% of light stabilizer, is at least 150% of the time which results in the same change to the surface structure or mechanical properties in the absence of the light stabilizer.

Basic light stabilizers preferably have a $pK_a$ or $pK_{BH^+}$ of ≥8. The $pK_a$ or $pK_{BH^+}$ of a light stabilizer can be measured in water or an aqueous, neutral solvent, or, if desired, can also be calculated by commonplace methods.

The light stabilizers preferably have a secondary amino, nitroxyl, hydroxylamino or alkoxy-amino group, or else a —N= group, which is in tautomerism with a phenol or forms a hydrogen bond to the proton of the phenol. It is of course also possible to use mixtures of light stabilizers, in which case, for example, from 2 to 12 light stabilizers with the same active substructures or else different active substructures may be combined.

Particularly preferred light stabilizers are those comprising the following substructures:

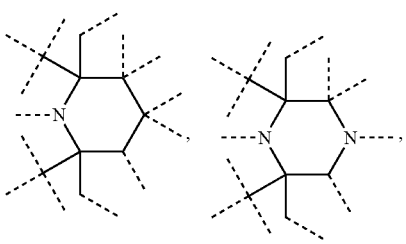

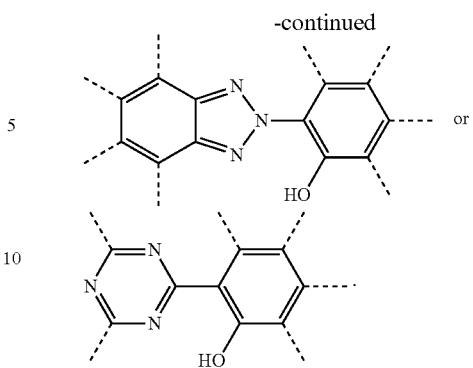

Sterically hindered amines are, for example, bis(2,2,6,6-tetramethylpiperid-4-yl)sebacate, bis(2,2,6,6-tetramethylpiperid-4-yl)succinate, bis(1,2,2,6,6-pentamethylpiperid-4-yl) sebacate, bis(1-octyloxy-2,2,6,6-tetramethylpiperid-4-yl) sebacate, n-butyl-3,5-di-tert-butyl-4-hydroxybenzylmalonic acid bis(1,2,2,6,6-pentamethylpiperidyl)ester, condensation product of 1-hydroxyethyl-2,2,6,6-tetramethyl-4-hydroxypiperidine and succinic acid, linear or cyclic condensation products of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)malonate, 3-n-octyl-7,7,9,9-tetramethyl-1,3,8-triazaspiro[4.5]-decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensation products of N,N'-bis(2,2,6,6-tetramethyl-4-piperidyl)hexamethylenediamine and 4-morpholino-2,6-dichloro-1,3,5-triazine, the condensation product of 2-chloro-4,6-di(4-n-butylamino-2,2,6,6-tetramethylpiperidyl)-1,3,5-triazine and 1,2-bis(3-aminopropylamino)ethane, the condensation product of 2-chloro-4,6-di (4-n-butylamino-1,2,2,6,6-pentamethylpiperidyl)-1,3,5-triazine and 1,2-bis(3-aminopropyl-amino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione, the mixture of 4-hexadecyloxy- and 4-stearyloxy-2,2,6,6-tetramethylpiperidine, the condensation product of N,N'-bis(2,2,6,6-tetramethyl-4-piperidyl)hexamethylenediamine and 4-cyclohexylamino-2,6-dichloro-1,3,5-triazine, condensation product of 1,2-bis(3-aminopropylamino)ethane and 2,4,6-trichloro-1,3,5-triazine and also 4-butylamino-2,2,6,6-tetramethylpiperidine (CAS Reg. No. [136504-96-6]); the condensation product of 1,6-diaminohexane and 2,4,6-trichloro-1,3,5-triazine and also N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro [4.5]decane, the reaction product of 7,7,9,9-tetramethyl-2-cycloundecyl-1-oxa-3,8-diaza-4-oxospiro[4.5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylene-diamine, the diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, the reaction product of maleic anhydride-α-olefin copolymer and 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperid-4-yl)-N-butylamino]-6-(2-hydroxyethyl)amino-1,3,5-triazines, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor® (Clariant; CAS Reg. No. 106917-31-1), 5-(2-ethylhexanoyl)oxymethyl-3,3,5-trimethyl-2-morpholinone, the reaction product of 2,4-bis[(1-cyclohexyloxy-2,2,6,6-piperid-4-yl)butylamino]-6-chloro-s-triazine with N,N'-bis(3-aminopropyl)ethylenediamine, 1,3,5-tris(N-cyclohexyl-N-(2,2,6,6-tetramethylpiperazin-3-on-4-yl)amino)-s-triazines or 1,3,5-tris(N-cyclohexyl-N-(1,2,2,6,6-pentamethylpiperazin-3-on-4-yl)amino)-s-triazines.

2-(2-Hydroxyphenyl)-1,3,5-triazines are, for example, 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)phenyl]-4,6-bis(2,4-dimethylphenyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine or 2,4-bis(4-[2-ethylhexyloxy]-2-hydroxyphenyl)-6-(4-methoxyphenyl)-1,3,5-triazine.

2-(2'-Hydroxyphenyl)benzotriazoles are, for example, 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)-benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyl-oxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)-phenyl)benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; transesterification product of 2-[3'-tert-butyl-5'-(2-methoxycarbonylethyl)-2'-hydroxyphenyl]benzotriazole with polyethylene glycol 300;

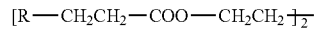

with R=3'-tert-butyl-4'-hydroxy-5'-2H-benzotriazol-2-ylphenyl; 2-[2'-hydroxy-3'-(α,α-dimethylbenzyl)-5'-(1,1,3,3-tetramethylbutyl)phenyl]benzo-triazole; 2-[2'-hydroxy-3'-(1,1,3,3-tetramethylbutyl)-5'-(α,α-dimethylbenzyl)phenyl]benzo-triazole.

Reference may additionally be made to the basic light stabilizers which are disclosed in U.S. Pat. No. 6,392,041, EP 1 263 855, U.S. Pat. No. 6,828,364, WO 03/016 388, CH 480 090, CH 480 091, CH 484 695, DE 4 444 258, DE 10 009 286, DE 19 500 441, DE 19 536 376, DE 19 538 950, DE 19 541 941, DE 19 701 718, DE 19 701 719, DE 19 723 582, EP 165 608, EP 200 190, EP 280 653, EP 280 654, EP 310 083, EP 345 212, EP 357 545, EP 395 938, EP 425 429, EP 434608, EP 434 619, EP 441 746, EP 442 847, EP 444 323, EP 453 396, EP 453 405, EP 458 741, EP 459 950, EP 466 647, EP 468 921, EP 483 488, EP 497 734, EP 500 496, EP 502 816, EP 502 821, EP 506 615, EP 512 946, EP 520 938, EP 523 006, EP 526 399, EP 530 135, EP 531 258, EP 546 993, EP 556156, EP 557 247, EP 577 559, EP 584 044, EP 603 130, EP 604 980, EP 618 205, EP 621 266, EP 648 753, EP 648 754, EP 649 841, EP 654 469, EP 659 877, EP 665 294, EP 679 691, EP 682145, EP 693 483, EP 697 481, EP 704 437, EP 704 444, EP 704 560, EP 706 083, EP 711 804, EP 743 309, EP 744 632, EP 750 011, EP 816 346, EP 824119, EP 824 909, EP 825 226, EP 826 675, EP 870 797, EP 878 469, EP 899 302, EP 900 823, EP 941 989, EP 946 631, EP 964 096, EP 1 005 325, EP 1 033 243, EP 1 104 781, EP 1 127 912, EP 1 298 126, EP 1 308 084, EP 1 308 308, EP 1 308 311, EP 1 346 845, FR 2363 133, GB 2 289 290, GB 2 290 745, GB 2 293 823, GB 2 297 091, GB 2 344 596, GB 2 361 005, GB 2 367 824, JP S48/38 338, JP H07/18 585, JP H07/134 360, JP H08/151 480, JP H08/188 737, JP H08/193 180, JP H08/267 915, JP H08/224049, JP H09/176 476, JP H09/187 906, JP H09/194682, JP H09/20 760, JP H09/22 099, JP H09/227 794, JP H09/52 916, JP H09/59 263, JP H10/1 599, JP H10/17 556, JP H10/44 356, JP H10/44 357, JP H10/44 358, JP H10/60 212, JP H10/110 140, JP H10/17 557, JP H10/204 284, JP H11/71 355, JP H11/71 356, JP H11/160 840, JP H11/174 638, JP H11/181 304, JP 2000/44 901, JP 2000/136 270, JP 2000/154 322, JP 2000/191 918, JP 2001/92 082, JP 2001/277 720, JP 2002/38 027, JP 2002/160 452, JP 2002/226 522, U.S. Pat. Nos. 3,113,940, 3,113,941, 3,113,942, 3,118,887, 3,134,749, 3,242,175, 3,244,708, 3,249,608, 3,423,360, 3,442,898, 3,444,164, 3,496,134, 3,535,318, 3,641,213, 3,843,371, 3,845,049, 4,826,978, 5,231,135, 5,288,867, 5,462,846, 5,489,503, 5,563,224, 5,585,422, 5,686,233, 5,714,530, 5,721,298, 5,726,310, 5,753,729, 5,760,228, 5,780,214, 5,871,669, 5,955,060, 5,959,008, 5,984,976, 5,998,116, 6,013,704, 6,057,444, 6,060,543, 6,111,103, 6,117,997, 6,184,375, 6,346,619, 6,495,122, 6,558,887, 6,562,083, 6,632,944, 6,706,215, 6,773,861, US 2003/0 146412, WO 86/03 528, WO 94/01 878, WO 94/05 645, WO 95/22 959, WO 96/17 009, WO 96/28 431, WO 96/29 302, WO 96/33 237, WO 97/03 642, WO 97/03 643, WO 97/36 880, WO 97/40 409, WO 98/03489, WO 98/06 575, WO 98/22447, WO 98/27146, WO 98/27 168, WO 98/55 526, WO 98/58 995, WO 99/26 934, WO 99/26 935, WO 99/55 471, WO 99/57 189, WO 99/67 223, WO 99/67 224, WO 99/67 225, WO 99/67 226, WO 99/67 227, WO 99/67 246, WO 00/14 074, WO 00/14 075, WO 00/14 076, WO 00/14 077, WO 00/22 020, WO 00/25 730, WO 00/25 731, WO 00/29 392, WO 00/39 209, WO 00/61 685, WO 00/66 675, WO 00/78 277, WO 01/47 900, WO 01/57 124, WO 01/62 821, WO 01/79 340, WO 01/90 233, WO 01/90 244, WO 02/28 854, WO 03/04 557, WO 03/35 734, WO 03/60 001, WO 03/70 819, WO 04/00 921, WO 04/104 081, WO 02/36 579, WO 06/82 145, WO 06/131 466, WO 06/131 469 and Mod. Plast. Proc. and Appl. 2002, 24, and also to the many commercial products which have the substructures disclosed above.

The black colorants of the invention can be used for colouring paints, printing inks and plastics in the mass. The invention accordingly also provides for the use of colorants of the invention and colorants prepared in accordance with the invention for colouring paints, printing inks and plastics in the mass, and also to a mass-coloured, high molecular weight material containing from 0.01% to 70% by weight, based on the total coloured, high molecular weight material, of a colorant of the invention or prepared in accordance with the invention. It is preferred to use single-phase pigments of the invention in which other crystal polymorphs are present in an amount of less than 20% by weight, preferably less than 10% by weight, based on the total amount of all crystal polymorphs.

The high molecular weight organic material to be coloured in accordance with the invention may be of natural or synthetic origin, and typically has a molecular weight in the range from $10^3$ to $10^8$ g/mol. Such materials may be, for example, natural resins or drying oils, rubber or casein, or modified natural substances, such as chlorinated rubber, oil-modified alkyd resins, viscose, cellulose ethers or esters, such as cellulose acetate, cellulose propionate, cellulose acetobutyrate or nitrocellulose, but more particularly all-synthetic organic polymers (both thermosets and thermoplastics), as are obtained by chain-growth addition polymerization, step-growth addition polymerization or condensation polymerization, for example polycarbonate, polyesters such as polyethylene terephthalate or polybutylene terephthalate, polyolefins such as polyethylene (HDPE, HDPE-HMW, HDPE-UHMW, LDPE, LLDPE, VLDPE, ULDPE), polypropylene or polyisobutylene, substituted polyolefins such as polymers of vinyl chloride, vinyl acetate, styrene, acrylonitrile or acrylic and/or methacrylic ester or butadiene, polystyrene or polymethyl methacrylate, and copolymers of the aforementioned monomers, especially acrylonitrile/butadiene/styrene (ABS), styrene/acrylonitrile (SAN) or EVA.

From the group of the step-growth addition polymerization resins and condensation polymerization resins, mention may be made of the condensation products of formaldehyde with phenols, known as phenolic resins, and of the condensation products of formaldehyde with urea, thiourea and melamine, known as amino resins, of the polyesters used as film-forming resins, including both saturated resins, such as alkyd resins, and unsaturated resins, such as maleate resins, and also of the linear polyesters and polyamides or silicones.

Furthermore, the high molecular weight organic material may be a binder for paints or printing inks, such as linseed oil varnish, nitrocellulose, alkyd resins, melamine resins, urea-formaldehyde resins, acrylic resins or other curable or polymerizable precursors.

The abovementioned high molecular weight compounds may be present individually or in mixtures, as plastic masses, solutions or melts, which if desired may be spun into fibres. The form in question may be either a ready-to-use composition or an article formed from it, or else a masterbatch, in the form of pellets, for example. If desired, for the colouring of high molecular weight organic materials in accordance with the invention, it is also possible to use customary adjuvants, which may be present in the uncoloured organic material, or may be added during incorporation.

Examples of such adjuvants are stabilizers, such as antioxidants, UV stabilizers or light stabilizers, surfactants, wetting agents, plasticizers or texture improvers. If texture improvers are required, they are, optionally, added preferably to the colorants of the invention during their actual synthesis, or during aftertreatment.

Examples of texture improvers are fatty acids having at least 12 carbon atoms, such as stearic acid or behenic acid in particular, stearamide, or behenamide, salts of stearic or behenic acid such as magnesium, zinc or aluminium stearate or behenate, or else quaternary ammonium compounds such as, in particular, tri($C_1$-$C_4$)alkylbenzylammonium salts such as trimethyl-, triethyl-, tri-n-propyl-, triisopropyl-, tri-n-butyl-, tri-sec-butyl- or tri-tert-butylbenzylammonium salts, or else plasticizers such as epoxidized soybean oil, waxes such as polyethylene wax, resin acids, such as abietic acid, rosin soap, hydrogenated or dimerized rosin, ($C_{12}$-$C_{18}$) paraffindisulphonic acid, alkylphenols or alcohols such as stearyl alcohol, or else laurylamine or stearylamine, and/or else aliphatic 1,2-diols such as dodecane-1,2-diol.

Preferred texture improvers are laurylamine or stearylamine, aliphatic 1,2-diols, stearic acid or its amides, salts or esters, epoxidized soybean oil, waxes or resin acids.

Such adjuvants may be added, for example, advantageously in amounts of 0.05% to 25% by weight, preferably of 0.5% to 15% by weight, based on the composition of the invention, before, during or after its preparation.

The high molecular weight organic substances are pigmented with the colorants of the invention, for example, by mixing such a colorant, optionally in the form of a masterbatch, into these substrates, using roll mills, mixing apparatus or milling apparatus. Thereafter the coloured material is generally brought into the desired ultimate form by means of techniques which are known per se, such as calendering, compression moulding, extrusion, coating, spraying, casting, printing or injection moulding. In order to produce mouldings that are not rigid, or to reduce their brittleness, it is often desirable to incorporate plasticizers into the high molecular weight compounds prior to their shaping. Examples of useful plasticizers include esters of phosphoric acid, phthalic acid or sebacic acid. In the process of the invention, the plasticizers can be incorporated into the polymers before or after the colorant has been incorporated. A further possibility, in order to obtain different hues, is to admix the high molecular weight organic materials not only with the colorant compositions but also with fillers, reinforcing materials (organic or inorganic fibres, for example), and/or other colouring components such as white, chromatic or black pigments, and also effect pigments, in the quantity desired in each case.

The admixing of the colorant may also be carried out immediately prior to the actual processing step, by continuously metering, for example, a powderous colorant of the invention and a pelletized, high molecular weight organic material, and also, optionally, adjuvants such as additives, for example, simultaneously and directly to the feed zone of an extruder, with incorporation taking place shortly prior to processing. Generally speaking, however, it is preferred to mix the colorant into the high molecular weight organic material during operation, since more uniform results can be obtained.

For the colouring of paints and printing inks, the high molecular weight organic materials and the colorants of the invention, optionally together with adjuvants such as stabilizers, dispersants, gloss enhancers, fillers, other pigments, siccatives or plasticizers, are finely dispersed or dissolved, in general, in an organic and/or aqueous solvent or solvent mixture. One possible procedure in this context is to disperse or dissolve the individual components by themselves, or else two or more together, and only then to combine all of the components.

Paints are applied, for example, by dipping, knife coating, film application, brushing or spraying, to give—after drying and curing, advantageously thermally or by irradiation—coatings of the invention. Further methods of application that lead to coatings are powder coating or roll-coating (coil coating) techniques, which in all their details are known per se to a person skilled in the art.

Where the high molecular weight material to be coloured is a paint, it may be a customary paint, or else a speciality paint, such as an automotive finish, for example. The paint may be part of a multi-coat paint system. Effect finishes are possible through addition of metal flakes, optionally coated micas and/or interference pigments. The advantages of the colorants of the invention are particularly striking in paint applications, and include, for example, increased colour strength in tandem with higher opacity and only a low level of heating in the sun.

Preferably the paint of the invention is provided additionally with a clear varnish in customary thickness as protection, this varnish comprising, for example, one or more UV absorbers or effect pigments. Where the coating of the invention is located on a metallic substrate, the substrate is preferably a primer-coated substrate.

The articles coloured in accordance with the invention have outstanding jet-black shades with good fastnesses that are largely inert towards near-infrared radiation. For the properties and applications, reference may be made here in particular to page 9/line 13 to page 29/line 11 of WO-2009/010 521, the black colorants prepared in accordance with the invention being superior to those of WO-2009/010 521 in terms of colour strength, shade and fastness properties.

Surprisingly, the black colorants of the invention, in powder coatings or coil coatings, lead to outstanding results, particularly in comparison with carbon black (C. I. Pigment Black 7). In addition to the jet-black shade, adhesion, through-curing and gloss, and also a particularly smooth and regular surface, are advantageous.

A further embodiment, of particular interest, of the black colorants of the invention is their use in mulch films, instrument panels or woven fabrics, especially those for installation in vehicles, for garden furniture, such as benches, chairs, recliners and tables, or in materials and elements for the construction industry, such as roofing elements or facade elements, window and doors. Mulch films are especially subject to sun exposure and have a tendency towards premature decomposition, losing their function and tarnishing the landscape with scraps that flutter around. If, on the other hand, the amount of light stabilizers is increased, then the desired complete biodegradation of the mulch films at the end of the vegetation cycle is slowed down, and the pollution of the soil is increased. Mulch films of the invention also have less of a preventive effect on the growth of the crop plants in the early growth phase as compared with mulch films pigmented conventionally (with carbon black, for example). Automotive, garden and construction articles are likewise strongly exposed to the sun, and, depending on their colouring, become excessively hot, and deform or break down prematurely. These problems are largely avoided by the colorants and compositions of the invention.

The examples below illustrate the invention without restricting its scope (unless otherwise indicated, "%" is always % by weight):

EXAMPLE 1

A mixture of 2.3 g of 2,5-dihydroxybenzene-1,4-diacetic acid (Aldrich), 3.0 g of isatin (98%, Aldrich) and 0.7 g of p-toluenesulphonic acid monohydrate (Fluka purum) in 75 ml of toluene is heated to 110° C. It is stirred for 7 hours with elimination of water, and stirred for a further 14 hours. The mixture is cooled and the black suspension is filtered. The residue is washed with 100 ml of methanol and dried at 60° C./$10^4$ Pa. The X-ray powder diagram has lines at 7.8 s, 10.2 w, 12.6 s, 18.6 w, 21.8 w, 22.4 w, 24.4 m, 25.0 w, 26.7 m, 27.2 m and 28.8 w °2θ (cf. FIG. 1).

EXAMPLE 2

2.3 g of 2,5-dihydroxybenzene-1,4-diacetic acid (Aldrich), 3.0 g of isatin (98%, Aldrich) and 1.9 g of p-toluenesulphonic acid hydrate (Fluka purum) are stirred in a mixture of 57 ml of concentrated acetic acid and 10 ml of water, and the resulting mixture is heated to reflux temperature and stirred at this temperature for 20 hours. Then the reaction mixture is stirred further, without heating, until the temperature has dropped to 90° C., at which point it is filtered and the residue is washed first with 30 ml of cold concentrated acetic acid and then with 150 ml of methanol. The product is dried for 24 hours at 40° C./$10^4$ Pa. The X-ray powder diagram of the black powder (4.2 g) has lines at 6.6 s, 13.3 w, 14.8 w, 21.6 w, 24.5 w, 26.4 m and 28.7 w °2θ (cf. FIG. 2).

EXAMPLE 3

6 g of the compound prepared in Example 2 are heated to 130° C. in 60 ml of dimethyl sulphoxide and stirred at this temperature for 18 hours. The reaction mixture is stirred further, without heating, until the temperature has dropped to 100° C., at which point it is filtered and the residue is washed first with 10 ml of dimethyl sulphoxide and then with 150 ml of water. The product is dried for 24 hours at 40° C./$10^4$ Pa. The X-ray powder diagram of the black powder (4 g) has lines at 7.3 s, 10.9 w, 12.7 w, 14.6 w, 24.5 w, 26.4 m and 28.7 w °2θ (cf. FIG. 3).

EXAMPLE 4

A kneading apparatus with a capacity of 0.5 liter is charged with 33 g of product from Example 1, 196 g of sodium chloride and 77 g of N-methylpyrrolidone and the rotary speed is set at 65 rpm. The walls of the apparatus are thermostated at 80° C. After 6 hours, 150 ml of water are added. The mixture obtained is poured into a porcelain suction filter, and the solid material on the filter is washed further with water until the wash water is salt-free. The product is dried for 12 hours at 80° C./$10^4$ Pa and passed through a sieve with a mesh size of 0.4 mm. The X-ray powder diagram has lines at 7.8 s, 10.2 w, 12.6 s, 18.6 w, 21.8 w, 22.4 w, 24.4 m, 25.0 w, 26.7 m, 27.2 m and 28.8 w °2θ (cf. FIG. 1).

EXAMPLE 5

A kneading apparatus with a capacity of 0.5 liter is charged with 30 g of product from Example 1, 180 g of sodium chloride and 85 g of N-methylpyrrolidone and the rotary speed is set at 65 rpm. The walls of the apparatus are thermostated at 20° C. After 4½ hours, 150 ml of water are added. The resulting mixture is poured into a porcelain suction filter and the solid material on the filter is washed further with water until the wash water is salt-free. The X-ray powder diagram has lines at 6.6 s, 13.3 w, 14.8 w, 21.6 w, 24.5 w, 26.4 m and 28.7 w °2θ (cf. FIG. 2).

EXAMPLE 6

A kneading apparatus with a capacity of 0.5 liter is charged with 35 g of product from Example 41, 210 g of sodium chloride and 105 g of dimethyl sulphoxide and the rotary speed is set at 65 rpm. The walls of the apparatus are thermostated at 45° C. After 6 hours, 150 ml of water are added. The resulting mixture is poured into a porcelain suction filter and the solid material on the filter is washed further with water until the wash water is salt-free. The product is dried for 12 hours at 80° C./$10^4$ Pa and passed through a sieve with a mesh size of 0.4 mm. The X-ray powder diagram has lines at 7.3 s, 10.9 w, 12.7 w, 14.6 w, 24.5 w, 26.4 m and 28.7 °2θ (cf. FIG. 3).

EXAMPLE 7

A procedure similar to that of Example 1 is followed, but with isatin replaced by an equimolar amount of 5-methylisatin (Aldrich 97%). The X-ray powder diagram has lines at 7.2 s, 9.7 w, 11.6 s, 12.7 w, 19.2 w, 20.4 w, 21.5 w, 24.3 w, 25.0 w, 26.6 w and 28.5 w °2θ (FIG. 4).

EXAMPLE 8

A mixture of 5.65 g of 2,5-dihydroxybenzene-1,4-diacetic acid (Aldrich), 9.9 g of 5-nitroisatin (97%, Aldrich) and 1.8 g of p-toluenesulphonic acid (Fluka purum) in 175 ml of acetic acid is heated to 110° C. and stirred for 20 hours more. The mixture is cooled and the black suspension is filtered. The residue is washed with 200 ml of methanol and dried at 60° C./$10^4$ Pa. The X-ray powder diagram has lines at 6.7 w, 12.6 m, 14.1 w, 15.7 w, 17.2 w, 19.6 w, 23.3 w, 24.8 w, 25.4 w, 27.6 s, 31.0 w and 34.3 w °2θ (FIG. 5).

EXAMPLE 9

A procedure similar to that of Example 2 is followed, but with isatin replaced by 3.9 g of 5-nitroisatin (97%, Aldrich). The X-ray powder diffractogram of the black powder (4.1 g) has lines at 6.6 s, 9.7 w, 13.3 w, 16.2 w, 19.9 w, 22.1 w, 24.9 w, 26.9 w and 29.1 w °2θ (cf. FIG. 6; at ~22.1 °2θ a number of lines are poorly resolved).

EXAMPLE 10

A procedure similar to that of Example 8 is followed, but with 5-nitroisatin replaced by an equimolar amount of 5-methoxyisatin (Aldrich 98%). The X-ray powder diagram has lines at 7.0 s, 10.1 m, 11.8 s, 20.5 m, 21.8 m, 24.2 m, 26.3 s and 27.9 m °2θ (FIG. 7).

EXAMPLE 11

A procedure similar to that of Example 2 is followed, but with isatin replaced by 3.6 g of 5-methoxyisatin. The X-ray powder diffractogram of the black powder (3.6 g) has main lines at 6.2 s, 7.0 m, 10.1 m, 11.8 m, 20.5 w, 21.8 w, 26.3 w, 26.9 m and 27.8 w °2θ (cf. FIG. 8).

EXAMPLE 12

A procedure similar to that of Example 1 is followed, but with isatin replaced by an equimolar amount of 5-chloroisatin (97%, Aldrich), and 2,5-dihydroxybenzene-1,4-diacetic acid replaced by an equimolar amount of its diisobutyl ester. The X-ray powder diagram has lines at 7.1 m, 11.7 s, 19.2 w, 20.5 w, 22.6 m, 24.3 m, 25.6 w, 26.7 m, 27.1 m and 29.0 w °2θ (FIG. 9). Instead of the diisobutyl ester, as an alternative, it is also possible to use the diisopropyl ester.

EXAMPLE 13

A procedure similar to that of Example 2 is followed, but with isatin replaced by 3.7 g of 5-chloroisatin. This gives 4.2 g of a black powder whose X-ray powder diagram has lines at 4.7 s, 6.6 w, 9.3 w, 12.5 w, 14.5 w, 16.0 w, 19.7 w, 21.8 w, 24.6 w and 27.4 w °2θ. In addition to the crystal polymorph obtained according to Example 12, a further crystal polymorph is present, characterized by an X-ray powder diagram with lines at 4.7 s, 9.3 w, 14.5 w, 16.0 w, 19.7 w and 24.6 w °2θ (cf. FIG. 10).

EXAMPLE 14

A procedure similar to that of Example 1 is followed, but with isatin replaced by an equimolar amount of 5-chloroisatin (Aldrich 97%). The X-ray powder diagram has lines at 4.8 m, 12.6 m, 21.8 w, 24.9 m and 27.4 s °2θ (cf. FIG. 11).

EXAMPLE 15

A procedure similar to that of Example 1 is followed, but with isatin replaced by an equimolar amount of 5,7-dichloroisatin (Aldrich 97%). The X-ray powder diagram has lines at 5.9 w, 15.2 w, 23.9 w, 25.1 m and 26.8 s °2θ (cf. FIG. 12).

EXAMPLE 16

A procedure similar to that of Example 2 is followed, but with isatin replaced by 4.4 g of 5,7-dichloroisatin. The X-ray powder diffractogram of the black powder (3.6 g) has lines at 23.9 w and 26.9 s °2θ (cf. FIG. 13).

EXAMPLE 17

A procedure similar to that of Example 1 is followed, but with isatin replaced by an equimolar amount of 5-fluoroisatin (Aldrich 97%). The X-ray powder diagram has lines at 6.7 s, 14.8 m, 16.1 m, 19.9 m, 21.8 m, 22.3 m, 24.8 m, 26.8 s and 29.1 m °2θ (cf. FIG. 14).

EXAMPLE 18

A procedure similar to that of Example 2 is followed, but with isatin replaced by 3.4 g of 5-fluoroisatin (97%, Aldrich). The X-ray powder diffractogram of the black powder (3.2 g) has lines at 6.7 s, 9.7 w, 13.3 w, 14.9 w, 16.3 w, 20.0 w, 22.3 w, 25.0 w, 26.9 w and 29.2 w °2θ (cf. FIG. 15, at ~22.3 °2θ a number of lines are poorly resolved).

EXAMPLE 19

A procedure similar to that of Example 1 is followed, but replacing isatin by an equimolar amount of 5-bromoisatin (90%, Aldrich) and toluene by chlorobenzene. The X-ray powder diagram has lines at 10.0 w, 11.6 m, 19.3 m, 20.6 w, 22.1 s, 23.3 w, 24.3 m, 25.4 m, 26.0 w, 26.8 w, 26.9 s, 28.8 w and 31.3 w °2θ (cf. FIG. 16).

EXAMPLE 20

A procedure similar to that of Example 1 is followed, but replacing isatin by an equimolar amount of 5-chloro-7-methylisatin (97%, Aldrich). The X-ray powder diagram has lines at 6.0 m, 7.0 m, 9.2 w, 11.1 s, 19.7 w, 20.6 m, 22.4 w, 25.0 m, 26.5 s and 28.3 w °2θ (cf. FIG. 17)

EXAMPLE 21

A procedure similar to that of Example 19 is followed, but replacing isatin by an equimolar amount of 1-phenylisatin (97%, Aldrich). The X-ray powder diagram has lines at 6.7 s, 9.6 w, 10.7 w, 14.4 w, 15.2 w, 19.9 w, 21.6 w and 25.3 w °2θ (cf. FIG. 18)

EXAMPLE 22

A procedure similar to that of Example 19 is followed, but replacing isatin by an equimolar amount of 1-methylisatin (97%, Aldrich). The X-ray powder diagram has lines at 8.5 s, 10.7 w, 12.6 w, 13.2 w, 21.0 w, 21.9 w, 22.7 w, 24.5 w, 26.9 w and 28.6 w °2θ (cf. FIG. 19).

EXAMPLE 23

A procedure similar to that of Example 1 is followed, but with isatin replaced by an equimolar amount of 5,7-dimethylisatin (97%, Aldrich). The X-ray powder diagram has lines at 6.4 s, 11.1 m, 11.8 m, 26.4 m and 26.9 m °2θ (cf. FIG. 20; at 6.9 and 26.2-27.0 °2θ, the lines are poorly resolved).

EXAMPLE 24

The product obtained from Example 23 is recrystallized from glacial acetic acid at 110° C. for 16 hours. The X-ray powder diagram has lines at 6.9 s, 9.2 w, 11.1 s, 14.2 w, 20.3 w, 22.4 w and 26.3 m °2θ (cf. FIG. 21).

EXAMPLE 25

A procedure similar to that of Example 2 is followed, but with isatin replaced by 3.6 g of 5,7-dimethylisatin (97%, Aldrich). The X-ray powder diffractogram of the black powder (3.9 g) has lines at 6.9 s, 11.0 s, 20.3 w and 26.3 m °2θ (cf. FIG. 22). This product also appears to contain a trace of the polymorph obtained from Example 24.

EXAMPLE 26

A procedure similar to that of Example 1 is followed, but with isatin replaced by 4.0 g of 2,1-naphthisatin (prepared according to CH 93487 [1920]) and with toluene replaced by the same amount of aqueous acetic acid (60-90% by weight). The mass spectrum (MALDI) of the black powder (4.4 g) has a molecular peak at m/z 548.1.

EXAMPLE 27

A procedure similar to that of Example 1 is followed, but replacing isatin by an equimolar amount of 2,3-dioxoindoline-7-carboxylic acid (97%, Aldrich). The X-ray powder diagram has lines at 10.6 s, 14.4 w, 16.7 w, 19.1 w, 23.7 w, 25.2 w, 26.6 w and 27.9 w °2θ (cf. FIG. 23).

EXAMPLE 28

A procedure similar to that of Example 1 is followed, but with isatin replaced by an equimolar amount of isatin-5-sulphonic acid sodium salt (98%, Aldrich) and toluene replaced by aqueous acetic acid (80% by weight). The X-ray powder diagram of the black product has lines at 7.9 w, 9.7 w, 11.5 w, 12.6 s, 13.5 w, 15.9 w, 19.6 w, 21.4 m, 22.8 w, 23.5 w, 24.0 w, 25.4 m, 25.6 s, 27.9 w, 28.3 w, 29.1 w and 30.7 w °2θ (cf. FIG. 24).

EXAMPLE 29

A mixture of 9.2 g of 2,5-dihydroxybenzene-1,4-diacetic acid (Aldrich), 6.0 g of isatin (98%, Aldrich), 7.3 g of 5,7-dimethylisatin (98%, Aldrich) and 2.8 g of p-toluenesulphonic acid monohydrate (Fluka purum) in 160 ml of chlorobenzene is stirred at 23° C. and then heated to 130° C. and stirred for 7 hours with elimination of water, and then for 14 hours more. The mixture is cooled and the black suspension is filtered. The residue is washed with 200 ml of methanol and 200 ml of water and dried at 60° C./$10^4$ Pa. The X-ray powder diagram has lines at 7.6 s, 9.5 w, 11.8 s, 20.7 w, 24.7 m, 26.4 m and 28.4 m °2θ (cf. FIG. 25).

EXAMPLE 30

A mixture of 2.3 g of 2,5-dihydroxybenzene-1,4-diacetic acid (Aldrich), 1.5 g of isatin (98%, Aldrich), 1.7 g of 5-methylisatin (98%, Aldrich), 0.7 g of p-toluenesulphonic acid monohydrate (Fluka purum) and 40 ml of chlorobenzene is stirred at 23° C., heated to 130° C., then stirred at 110° C. for 16 hours and worked up as in Example 29. The X-ray powder diagram has lines at 7.4 s, 10.0 w, 11.9 s, 18.8 w, 20.1 w, 22.1 w, 24.1 m, 25.0 w, 26.6 m and 28.6 w °2θ (cf. FIG. 26) and corresponds essentially to that of the pure compound from Example 7 (cf. FIG. 4).

EXAMPLE 31

A kneading apparatus having a capacity of 0.5 liter is charged with 15 g of product from Example 1, 15 g of product from Example 7, 198 g of sodium chloride and 77 g of N-methylpyrrolidone and the rotary speed is set at 65 rpm. The walls of the apparatus are thermostated at 20° C. After 6 hours, 150 ml of water are added. The mixture obtained is poured onto a porcelain suction filter and the solid filter product is washed further with water until the wash water is salt-free. The product is dried for 12 hours at 80° C./$10^4$ Pa and passed through a sieve having a mesh size of 0.4 mm. The X-ray powder diagram has lines at 7.4 s, 10.0 w, 11.9 s, 18.8 w, 20.1 w, 22.1 w, 24.1 m, 25.0 w, 26.6 m and 28.6 w °2θ (virtually identical to FIG. 26).

EXAMPLE 32

A procedure similar to that of Example 30 is followed, but using a mixture of 2.0 g of the product from Example 12b of WO 00/24 736, 1.6 g of 5-methylisatin (98%, Aldrich), 1.8 g of 5,7-dimethylisatin (96%, Aldrich), 0.5 g of p-toluenesulphonic acid monohydrate (Fluka purum) and 40 ml of toluene. The X-ray powder diagram has lines at 7.2 s, 9.3 w, 11.3 s, 19.4 w, 20.6 w, 24.5 w, 26.4 m, 26.9 w and 28.3 w °2θ (cf. FIG. 27).

EXAMPLE 33

A procedure similar to that of Example 30 is followed, but using a mixture of 2.3 g of 2,5-dihydroxybenzene-1,4-diacetic acid (Aldrich), 1.5 g of isatin (98%, Aldrich), 1.9 g of 5-chloroisatin (97%, Aldrich), 0.7 g of p-toluenesulphonic acid monohydrate (Fluka purum) and 40 ml of toluene. The X-ray powder diagram has lines at 7.2 s, 7.4 s, 10.3 w, 11.9 m, 12.2 s, 13.3 w, 18.9 w, 20.2 w, 22.8 m, 24.1 s, 25.3 w, 26.8 s and 29.0 m °2θ (cf. FIG. 28).

EXAMPLE 34

A procedure similar to that of Example 32 is followed, but using a mixture of 1.6 g of 5-methylisatin (98%, Aldrich), 1.9 g of 5-chloroisatin (97%, Aldrich), p-toluenesulphonic acid and toluene. The X-ray powder diagram has lines at 7.1 s, 11.6 s, 19.2 w, 20.4 w, 21.9 w, 24.2 m, 25.2 w, 26.7 s and 28.7 w °2θ (cf. FIG. 29).

EXAMPLE 35

A procedure similar to that of Example 30 is followed, but using a mixture of 1.5 g of isatin (98%, Aldrich), 1.7 g of 5-fluoroisatin (97%, Aldrich), p-toluenesulphonic acid and chlorobenzene. The X-ray powder diagram has lines at 6.6 s, 13.5 w, 14.7 m, 15.9 w, 19.8 m, 21.6 m, 22.3 w, 24.6 m, 26.6 s and 28.8 m °2θ (cf. FIG. 30).

EXAMPLE 36

A procedure similar to that of Example 30 is followed, but using a mixture of 1.5 g of isatin (98%, Aldrich), 2.5 g of 5-bromoisatin (90%, Aldrich), p-toluenesulphonic acid and chlorobenzene. The X-ray powder diagram has lines at 7.1 m, 10.2 m, 11.8 s, 13.1 w, 18.8 m, 20.2 m, 22.7 s, 24.0 s, 25.3 m, 26.5 s, 26.8 s and 28.8 m °2θ (cf. FIG. 31).

EXAMPLE 37

A procedure similar to that of Example 30 is followed, but using a mixture of 1.5 g of isatin (98%, Aldrich), 1.8 g of 5-methoxyisatin (98%, Aldrich), p-toluenesulphonic acid and chlorobenzene. The X-ray powder diagram has lines at 7.0 s, 10.4 w, 11.6 m, 19.0 w, 20.3 w, 22.3 w, 24.0 w, 25.3 w, 26.5 m and 28.7 w °2θ (cf. FIG. 32).

EXAMPLE 38

A procedure similar to that of Example 32 is followed, but using a mixture of 2 g of 5-nitroisatin (97%, Aldrich), 1.8 g of 5-chloroisatin (97%, Aldrich), p-toluenesulphonic acid and toluene. The X-ray powder diagram has lines at 6.1 m, 11.9 m, 13.5 w, 15.0 w, 16.5 w, 22.6 w, 24.1 w, 24.7 w and 26.9 s °2θ (cf. FIG. 33).

EXAMPLE 39

A procedure similar to that of Example 32 is followed, but using a mixture of 1.1 g of 5,7-dichloroisatin (97%, Aldrich), 0.9 g of 5-chloroisatin (97%, Aldrich), p-toluenesulphonic acid and toluene. The X-ray powder diagram has lines at 4.6 s, 9.3 w, 11.6 m, 14.2 w, 17.1 w, 18.8 w, 22.1 w, 25.4 m, 26.0 m and 27.5 s °2θ (cf. FIG. 34).

EXAMPLE 40

A procedure similar to that of Example 38 is followed, but using a mixture of 1.8 g of 5-methoxyisatin (98%, Aldrich), 0.9 g of 5-chloroisatin (97%, Aldrich), p-toluenesulphonic acid and toluene. The X-ray powder diagram has lines at 7.0 s, 11.2 s, 12.7 w, 19.4 w, 20.7 w, 21.6 w, 22.5 w, 24.3 w, 25.3 w, 26.8 m and 28.7 w °2θ (cf. FIG. 35).

EXAMPLE 41

The procedure of Example 1 is repeated but replacing the compound of the formula

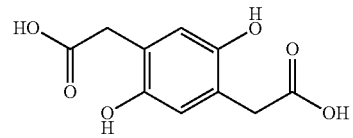 [SMILES: O=C(O)Cc1cc(O)c(CC(=O)O)cc1O]

by an equimolar amount of the compound of the formula

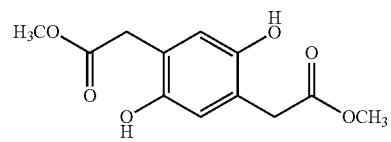 [SMILES: COC(=O)Cc1cc(O)c(CC(=O)OC)cc1O]

(prepared according to J. Org. Chem. 32, 3155-3159 [1967]). In a good yield, the same product as in Example 1 is obtained.

EXAMPLE 42

The procedure of Example 1 is repeated but replacing the compound of the formula

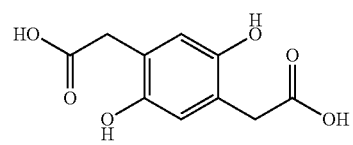

by an equimolar amount of the compound of the formula

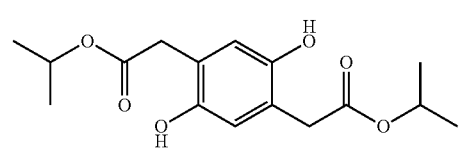 [SMILES: CC(C)OC(=O)Cc1cc(O)c(CC(=O)OC(C)C)cc1O]

(prepared according to J. Org. Chem. 32, 3155-3159 [1967]). In a good yield, the same product as in Example 1 is obtained.

EXAMPLE 43

5.0 g of the product from Example 1 are introduced in portions over the course of 5 minutes at 23° C. into 30 ml of chlorosulphonic acid. The reaction solution is stirred for 3 hours and then stirred over the course of 30 minutes into 500 ml of ice-water. The suspension is filtered and the residue is washed with 100 ml of ice-water. 6 hours of drying at 30° C./$10^4$ Pa gives 3.2 g of a black powder. According to methods of mass spectroscopy, the product is composed primarily of the dichlorosulphonyl-substituted compound of Example 1.

In the ESI mass spectrum, a molecular peak is evident at m/z=644.9 (singly protonated molecule).

EXAMPLE 44

5.0 g of the product from Example 1 are stirred into 30 ml of 25% oleum. The reaction solution is cooled from 30° C. to 20° C., stirred at 23° C. for 4 hours, introduced into 500 ml of ice-water and stirred again for an hour. 25 g of tributylamine (large excess) are added over the course of 5 minutes. The suspension is stirred for 30 minutes and filtered and the residue is washed with 50 ml of water and suspended again in 100 ml of water. A further 5 g of tributylamine are added to the suspension, and then the product is extracted with twice 150 ml of methylene chloride. The two organic phases are combined and stirred into 1200 ml of hexane; the product is precipitated in the form of fine crystals. The suspension is stirred for 30 minutes more and filtered through a glass fibre filter. Since the product tends to run apart on the filter, it is advantageous to dissolve it in 100 ml of methylene chloride and isolate it by stripping off the solvent on a rotary evaporator at only a slightly elevated temperature (<40° C.). After 24 hours of drying at 30° C./$10^4$ Pa, 2.1 g of black solid are obtained. In the ESI mass spectrum a molecular peak is evident at m/z=606.0, corresponding to the dianion of the disulphonated compound. The position of the sulpho groups, however, cannot be unambiguously assigned by $^1$H-NMR spectroscopy (the product is possibly an isomer mixture; cf. Example 28).

EXAMPLE 45

A procedure similar to that of Example 44 is followed, but replacing tributylamine by the same amount of trioctylmethylammonium bromide. This gives 1.6 g of black product which corresponds approximately to the doubly neutralized sulpho salt.

| Elemental analysis [%]: | theor.: | C 67.92 | H 8.85 | N 4.17 | O 14.29 | S 4.77; |
|---|---|---|---|---|---|---|
| $C_{76}H_{118}N_4O_{12}S_2$ | found: | C 66.35 | H 9.11 | N 3.77 | O 14.30 | S 5.45. |

EXAMPLE 46

A procedure similar to that of Example 44 is followed, but replacing tributylamine by the same amount of octadecyltrimethylammonium bromide. This gives 8.3 g of black product which corresponds approximately to the singly neutralized sulpho salt.

| Elemental analysis [%]: | theor.: | C 61.35 | H 6.24 | N 4.57 | O 20.87 | S 6.97; |
|---|---|---|---|---|---|---|
| $C_{47}H_{57}N_3O_{12}S_2$ | found: | C 58.90 | H 7.47 | N 4.01 | O 21.25 | S 6.74. |

EXAMPLE 47

A procedure similar to that of Example 44 is followed, but replacing tributylamine by the same amount of tetraethylammonium bromide. This gives 1.2 g of black product.

EXAMPLE 48

A procedure similar to that of Example 1 is followed, but replacing toluene by ethyl acetate. The principal product is the same as in Example 1, but the reaction takes place much more slowly than in toluene, and the product contains a trace of the product from Example 2.

EXAMPLES 49-50 AND COMPARATIVE EXAMPLE 51

An oxo-biodegradable mulch film is produced by mixing Dowlex® NG 5056-G LLDPE (melt index 1.1 g/10 min; 190° C./2.16 kg; contains 0.10% by weight tris(2,4-di-t-butylphenyl)phosphite and 0.032% by weight octadecyl 3-(3,5-di-tert-butyl-4-hydroxyphenyl)propionate) in a turbo mixer (Labo 10, Caccia®) with the following additives, and then processing the mixture to pellets at not more than 200° C. (O.M.C. twin-screw extruder, Ø=19; L/D=25) and finally processing the pellets by blowmoulding (Formac® laboratory blown-film extruder) at a maximum 210° C. to give a film with a thickness of 12 µm:

| | | Example | | |
|---|---|---|---|---|
| Additives | | 49 Film 1 | 50 Film 2 | 51 Film 3 |
| EB 51-733 (experimental pro-degradant) | | 2 | 2 | 2 |
| Tinuvin ® 783 (mixture of hindered amines) | | 0.4 | 0.4 | 0.4 |
| Product from Example 1 | | 6 | | |
| Product from Example 2 | | | 6 | |
| Plasblack ® 2642 | C.I.Pigment Black 7 | | | 6 |
| | Polyethylene | | | 9 |

All quantities are based on 100 parts by weight of film. Plasblack® 2642 is a PE masterbatch containing 40% carbon black.

The films are exposed in a Weather-O-meter® (Ci65 A/AT-LAS, 6500 W xenon without cycle, black standard temperature 63° C.), the specimens being examined periodically for the appearance of surface cracks, which indicate the beginning of macroscopic decomposition.

| Example | 49 | 50 | 51 |
|---|---|---|---|
| Additives | Film 1 | Film 2 | Film 3 |
| Time to beginning of decomposition [h] | 686 | 606 | 368 |
| Biooxidatively degradable | ✓ | ✓ | ✓ |

The mulch films of the invention (Examples 49 and 50) have a greatly improved light stability as compared with a conventional mulch film pigmented with carbon black (C. I. Pigment Black 7) (Comparative Example 51).

EXAMPLE 52 AND COMPARATIVE EXAMPLES 53-54

By means of two-stage dispersion (first 20 minutes with the Dispermat®, then 4 hours with 70 parts by weight of glass beads in a Skandex®), base formulations are prepared with the following components (all amounts are in parts by weight):

| Example | 52 | 53 | 54 |
|---|---|---|---|
| Dynapol ® LH 530 (60%) | 27.35 | 15.32 | 27.35 |
| Disparlon ® L 1984 | 0.39 | 0.80 | 0.39 |
| Solvesso ® 150 | 7.16 | 5.96 | 7.16 |
| Butyl glycol | 2.30 | 1.92 | 2.30 |
| Product from Example 1 | 2.80 | — | — |
| TiO$_2$ (Tiona ® 696, C.I. Pigment White 6) | — | 16.00 | — |
| Carbon black (FW 200 ™, C.I. Pigment Black 7) | — | — | 2.80 |
| Total | 40.00 | 40.00 | 40.00 |

These base formulations are then diluted with further components to give NIR-curable paints:

| Example | 52 | 53 | 54 |
|---|---|---|---|
| Base formulation (millbase) | 71.43 | 75.00 | 71.43 |
| Dynapol ® LH 530 (60%) | 9.28 | 6.91 | 9.28 |
| Shamrock ® S 381-N1 | 0.50 | 0.50 | 0.50 |
| Cymel ® 303 (99%) | 8.57 | 5.59 | 8.57 |
| Dynapol ® Catalyst 1203 (50%) | 1.14 | 0.74 | 1.14 |
| Byk ® Catalyst 450 | 0.20 | 0.20 | 0.20 |
| Solvesso ® 150 | 6.45 | 10.81 | 6.45 |
| Tinuvin ® 123 (100%, 1% on binder solids) | 0.37 | 0.24 | 0.37 |
| Total | 100.00 | 100.00 | 100.00 |
| Pigment concentration | 5.0% | 30.0% | 5.0% |
| Binder concentration | 41.8% | 54.0% | 41.8% |
| Colour | black | white | black |

These paints are applied to sheet aluminium with coil coated primer in a film thickness of 20 μm (after drying). For curing, heating takes place first at 300° C. for 30 s (peak metal temperature 225° C.), followed by passage on a conveyor belt through an infrared oven (distance from the belt 50 mm, belt speed 2 m/min, 6 Adphos® HB-NIR lamps). The temperature of the samples is measured at the exit from the oven, and then the samples are assessed visually and subjected to a rubbing test with methyl ethyl ketone. In contrast to Comparative Examples 53-54, the Inventive Example 52 gives excellent results:

| Example | Specimen temperature at exit from infrared oven | Visual | Double rubs withstood |
|---|---|---|---|
| 52 | 227° C. | cured, OK | ≥100 |
| 53 | 212° C. | tacky | 0 |
| 54 | 430° C. | partly burnt | — |

What is claimed is:
1. A process for preparing a black colorant comprising: reacting a compound of the formula

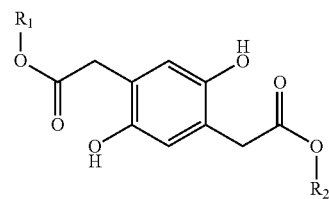

(i)

with a compound of the formula

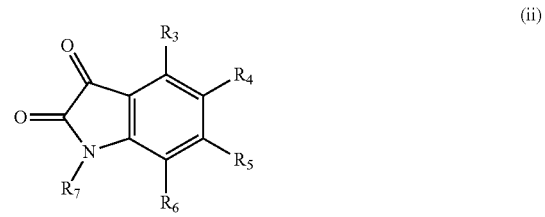

(ii)

in a molar ratio of 1:2 in the presence of a catalyst which in water at 25° C. has a pK≤4.5,
wherein
R$_1$ and R$_2$ independently of one another are H or are C$_1$-C$_{24}$alkyl, C$_3$-C$_{24}$cycloalkyl, C$_2$-C$_{24}$alkenyl, C$_3$-C$_{24}$cycloalkenyl or C$_2$-C$_{24}$alkynyl each unsubstituted or substituted by halogen or C$_1$-C$_8$alkoxy; are C$_7$-C$_{24}$aralkyl which is unsubstituted or substituted one or more times by halogen, nitro, cyano, C$_1$-C$_8$alkyl and/ or C$_1$-C$_8$alkoxy; or are C$_6$-C$_{24}$aryl which is unsubstituted or substituted one or more times by halogen, nitro, cyano, C$_1$-C$_8$alkyl and/ or C$_1$-C$_8$alkoxy;
R$_3$ is H, F, Cl, R$_8$ or OR$_8$;
R$_4$, R$_5$ and R$_6$ independently of one another are H, F, Br, Cl, COOH, COOR$_8$, CONH$_2$, CONHR$_8$, CONR$_8$R$_8$, CN, COR$_8$, SO$_3$H, SO$_2$Cl, SO$_2$NH$_2$, SO$_2$NHR$_8$, SO$_2$NR$_8$R$_8$, SO$_2$R$_8$, NO$_2$, R$_8$, OR$_8$, SR$_8$, NR$_8$R$_8$, NHCOR$_8$ or

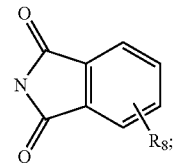

or R$_3$ and R$_4$, R$_4$ and R$_5$ or R$_5$ and R$_6$ in pairs together form a C$_1$-C$_8$alkylenedioxy, C$_3$-C$_6$alkylene, C$_3$-C$_6$alkenylene or 1,4-butadienylene radical, each unsubstituted or substituted one or more times by F, OR$_8$, NO$_2$, oxo, thioxo or SO$_3$H;
R$_7$ is H or is C$_1$-C$_{24}$alkyl, C$_3$-C$_{24}$cycloalkyl, C$_2$-C$_{24}$alkenyl, C$_3$-C$_{24}$cycloalkenyl, C$_2$-C$_{24}$alkynyl or C$_2$-C$_{12}$heterocycloalkyl, each unsubstituted or substituted one or more times by F, oxo or thioxo and uninterrupted or interrupted one or more times by O, S or NR$_8$; or is C$_7$-C$_{24}$aralkyl, C$_1$-C$_{12}$heteroaryl-C$_1$-C$_8$alkyl, C$_6$-C$_{24}$aryl or C$_1$-C$_{12}$heteroaryl, each unsubstituted or substituted one or more times by oxo, thioxo, F, Br, Cl, COOH, COOR$_8$, CONH$_2$, CONHR$_8$, CONR$_8$R$_8$, CN, COR$_8$, SO$_3$H, SO$_2$Cl, SO$_2$NH$_2$, SO$_2$NHR$_8$, SO$_2$NR$_8$R$_8$, SO$_2$R$_8$, NO$_2$, R$_8$, OR$_8$, SR$_8$, NR$_8$R$_8$, NHCOR$_8$ or

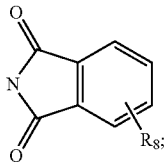

and each R$_8$, independently of all other R$_8$s, is C$_1$-C$_{24}$alkyl, C$_3$-C$_{24}$cycloalkyl, C$_2$-C$_{24}$alkenyl, C$_3$-C$_{24}$cycloalkenyl, C$_2$-C$_{24}$alkynyl or C$_2$-C$_{12}$heterocycloalkyl, each unsubstituted or substituted one or more times by F, oxo, thioxo, OR$_9$, SR$_9$ or NR$_9$R$_9$; or is C$_7$-C$_{24}$aralkyl, C$_1$-C$_{12}$heteroaryl-C$_1$-C$_8$alkyl, C$_6$-C$_{24}$aryl or C$_1$-C$_{12}$heteroaryl, each unsubstituted or substituted one or more times by oxo, F, Br, Cl, COOH, CONH$_2$, CONHR$_9$, CONR$_9$R$_9$, SO$_3$H, SO$_2$Cl, SO$_2$NH$_2$, SO$_2$NHR$_9$, SO$_2$NR$_9$R$_9$, CN, NO$_2$, OR$_9$, SR$_9$, NR$_9$R$_9$, NHCOR$_9$ or

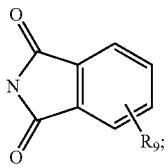

or two vicinal R$_8$s together
form —O—CO—O—, —O—CS—O—, —CO—N—CO—, —N—CO—N—, —N=S=N—, —N=C=C—, —O—C=C—, —S—C=C—, —O—C=N—, —S—C=N—, —N—N=N—, —N=C—C=C—, —C=N—C=C—, —N=C—C=N—, —C=N—N=C— or —C=N—C=N— or —C=C—C=C—, in which each —C= and —N—, independently of all other —C= and —N—, is substituted by H or R$_9$;
or two geminal or vicinal R$_8$s together form a C$_3$-C$_8$alkylene or C$_3$-C$_8$alkenylene radical, each unsubstituted or substituted one or more times by F, oxo or thioxo, and in which 0, 1 or 2 non-vicinal methylene units may be replaced by O, S or NR$_9$; and
each R$_9$, independently of all other R$_9$s, is C$_1$-C$_8$alkyl, C$_3$-C$_6$cycloalkyl or benzyl, each unsubstituted or substituted one or more times by oxo, thioxo, F and/or O—C$_1$-C$_8$alkyl; or is phenyl or C$_1$-C$_5$heteroaryl, each unsubstituted or substituted one or more times by F, Br, Cl, CO—C$_1$-C$_8$alkyl, COOH, CONH$_2$, CONHC$_1$-C$_8$alkyl, CON(C$_1$-C$_8$alkyl)$_2$, SO$_3$H, SO$_2$Cl, SO$_2$NH$_2$, SO$_2$NHC$_1$-C$_8$alkyl, SO$_2$N(C$_1$-C$_8$alky)$_2$, CN, NO$_2$, C$_1$-C$_8$alkyl, OC$_1$-C$_8$alkyl, SC$_1$-C$_8$alkyl or N(C$_1$-C$_8$alky)$_2$;
or two vicinal R$_9$s together
form —O—CO—O—, —O—CS—O—, —CO—N—CO—, —N—CO—N—, —N=S=N—, —N=C=C—, —O—C=C—, —S—C=C—, —O—C=N—, —S—C=N—, —N—N=N—, —N=C—C=C—, —C=N—C=C—, —N=C—C=N—, —C=N—N=C— or —C=N—C=N— or —C=C—C=C—, in which each —C= and —N— independently of all other —C= and —N— is substituted by H, F, oxo, thioxo, C$_1$-C$_8$alkyl or OC$_1$-C$_8$alkyl;
or two geminal or vicinal R$_9$s together form a C$_3$-C$_8$alkylene or C$_3$-C$_8$alkenylene radical, each unsubstituted or substituted one or more times by oxo or thioxo, and in which 0, 1 or 2 non-vicinal methylene units may be replaced by O, S or N(C$_1$-C$_8$alkyl).

2. A process according to claim 1, in which R$_3$, R$_5$ and R$_7$ are H, and R$_4$ and R$_6$ independently of one another are H, F, Br, Cl, COOH, COOR$_8$, CONH$_2$, CONHR$_8$, CONR$_8$R$_8$, CN, COR$_8$, SO$_3$H, SO$_2$Cl, SO$_2$NH$_2$, SO$_2$NHR$_8$, SO$_2$NR$_8$R$_8$, SO$_2$R$_8$, NO$_2$, R$_8$, OR$_8$ or NHCOR$_8$, or R$_5$ and R$_6$ together form a 1,4-butadienylene radical.

3. A process for preparing a black colorant comprising:
reacting a compound of the formula

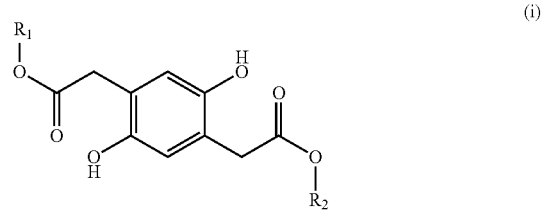

with 2 to 5 compounds of the formula

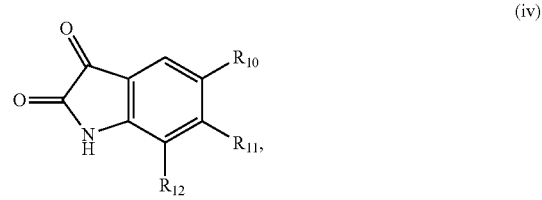

wherein
R$_1$ and R$_2$ independently of one another are H, or are C$_1$-C$_{24}$alkyl, C$_3$-C$_{24}$cycloalkyl, C$_2$-C$_{24}$alkenyl, C$_3$-C$_{24}$cycloalkenyl or C$_2$-C$_{24}$alkynyl, each unsubstituted or substituted by halogen or C$_1$-C$_8$alkoxy; or are C$_7$-C$_{24}$aralkyl which is unsubstituted or substituted one or more times by halogen, nitro, cyano, C$_1$-C$_8$alkyl and/or C$_1$-C$_8$alkoxy; or are C$_6$-C$_{24}$aryl which is unsubstituted or substituted one or more times by halogen, nitro, cyano, C$_1$-C$_8$alkyl and/or C$_1$-C$_8$alkoxy, R$_{10}$ is H, CH$_3$, C$_2$H$_5$, OCH$_3$, OC$_2$H$_5$, F, Cl, Br, NO$_2$, CN, COOH or SO$_3$H, R$_{11}$ is H, NO$_2$, CN, COOH or SO$_3$H, and R$_{12}$ is H, CH$_3$, C$_2$H$_5$, OCH$_3$, OC$_2$H$_5$, F, or Cl, in an overall molar ratio (i):(iv) of 1:2 in the presence of a catalyst which in water at 25° C. has a pK≤4.5, the amount of one of the compounds of the formula (iv) being from 50% to 80% by weight, based on the total amount of all compounds of the formula (iv).

4. A process according to claim 3, in which R$_{10}$ is H, CH$_3$, OCH$_3$, F, Cl, Br, NO$_2$ or SO$_3$H, R$_{11}$ is H or SO$_3$H, and R$_{12}$ is H, CH$_3$ or Cl.

5. A process according to claim 3, in which, as a main component of the formula (iv), the compound of the formula

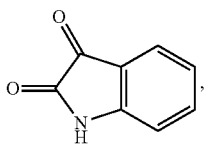 [SMILES: O=C1Nc2ccccc2C1=O]

and, as a secondary component of the formula (iv), a compound of the formula

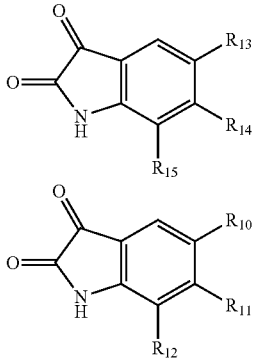

are reacted with the compound of the formula (i), where
$R_{13}$ is H, $C_1$-$C_8$alkyl, $OC_1$-$C_8$alkoxy, F, Cl, Br, $NO_2$, CN, COOH or $SO_3H$,
$R_{14}$ is H, $NO_2$, CN, COOH or $SO_3H$, and $R_{15}$ is H, Cl or $C_1$-$C_8$alkyl.

6. A process for preparing a black colorant comprising: reacting a compound of the formula

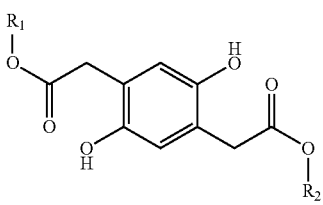

with 2 to 5 compounds of the formula

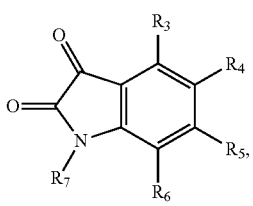

wherein $R_1$ to $R_7$ have the same definition as in claim 1, in an overall molar ratio (i):(ii) of 1:2 in the presence of a catalyst which in water at 25° C. has a pK≤4.5, the amount of one of the compounds of the formula (ii) being from 85% to 99.9% by weight, based on the total amount of all compounds of the formula (ii), and the compounds of the formula

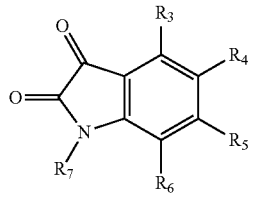

being added simultaneously or in any order before or during the reaction.

7. A process according to claim 1, in which a compound of the formula (ii) is selected from the group consisting of compounds having the following substitution patterns:
$R_3=R_4=R_5=R_6=R_7=H$;
$R_3=R_5=R_6=R_7=H$, $R_4=NO_2$;
$R_3=R_5=R_6=R_7=H$, $R_4=OCH_3$;
$R_3=R_5=R_6=R_7=H$, $R_4=Cl$;
$R_3=R_5=R_6=R_7=H$, $R_4=F$;
$R_3=R_5=R_6=R_7=H$, $R_4=Br$;
$R_3=R_5=R_6=R_7=H$, $R_4=SO_3H$;
$R_3=R_5=R_6=R_7=H$, $R_4=COOH$;
$R_3=R_5=R_6=R_7=H$, $R_4=N(CH_3)_2$;
$R_3=R_5=R_6=R_7=H$, $R_4=NHCOC_1$-$C_{18}$alkyl;
$R_3=R_5=R_6=R_7=H$, $R_4=C_1$-$C_{20}$alkyl;
$R_3=R_5=R_6=R_7=H$, $R_4=C_2$-$C_{20}$alkoxy;
$R_3=R_5=R_7=H$, $R_4=R_6=CH_3$;
$R_3=R_5=R_7=H$, $R_4=R_6=Cl$;
$R_3=R_5=R_7=H$, $R_4=Cl$, $R_6=CH_3$;
$R_3=R_4=R_5=R_6=H$, $R_7=CH_3$;
$R_3=R_4=R_5=R_6=H$, $R_7=C_6H_5$; and
$R_3=R_4=R_7=H$, $R_5$ and $R_6$ together=1,4-butadienylene.

8. A process according to claim 1, in which the reaction takes place with $5·10^{-3}$ to 5 mol of catalyst per mole of compound of the formula (i), at a pressure of $2·10^2$ to $2·10^6$ Pa, at a temperature of 20 to 250° C., and in a reaction time of ½ to 100 hours.

9. A process according to claim 1, in which the black colorant is composed of non-aggregated pigment particles, characterized by an average particle size L of 10 nm to 10 μm, with 60%-100% by weight, of the particles having a particle size of L±½ L.

10. A black colorant obtained according to claim 1 selected from the group consisting of:
the reaction product, obtained by acidic catalysis from

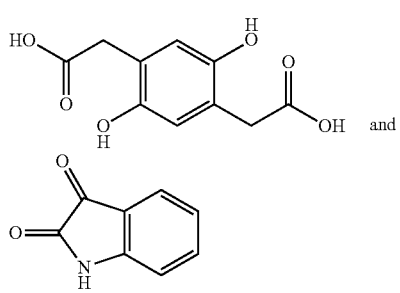

in a molar ratio of 1:2, of empirical formula $C_{26}H_{12}N_2O_6$, characterized by an X-ray powder diagram with lines at 7.8 s, 10.2 w, 12.6 s, 18.6 w, 21.8 w, 22.4 w, 24.4 m, 25.0 w, 26.7 m, 27.2 m and 28.8 w °2θ;

the reaction product, obtained by acidic catalysis from

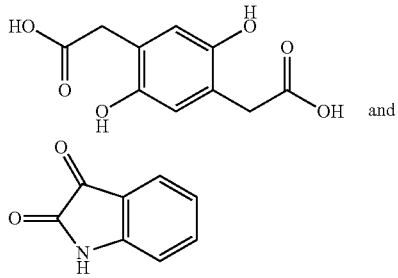

and in a molar ratio of 1:2, of empirical formula $C_{26}H_{12}N_2O_6$, characterized by an X-ray powder diagram with lines at 6.6 s, 13.3 w, 14.8 w, 21.6 w, 24.5 w, 26.4 m and 28.7 w °2θ;

the reaction product, obtained by acidic catalysis from

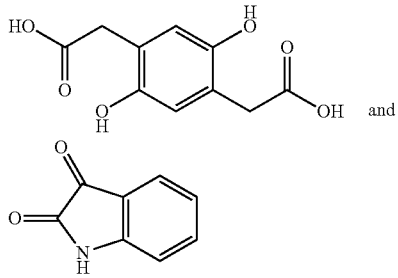

and in a molar ratio of 1:2, of empirical formula $C_{26}H_{12}N_2O_6$, characterized by an X-ray powder diagram with lines at 7.3 s, 10.9 w, 12.7 w, 14.6 w, 24.5 w, 26.4 m and 28.7 w °2θ;

the reaction product, obtained by acidic catalysis from

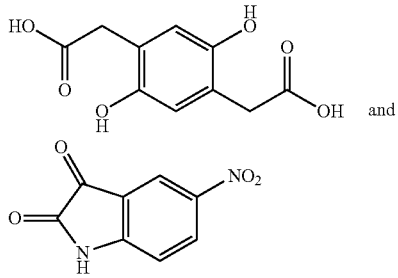

and in a molar ratio of 1:2, of empirical formula $C_{26}H_{10}N_4O_{10}$, characterized by an X-ray powder diagram with lines at 6.7 w, 12.6 m, 14.1 w, 15.7 w, 17.2 w, 19.6 w, 23.3 w, 24.8 w, 25.4 w, 27.6 s, 31.0 w and 34.3 w °2θ;

the reaction product, obtained by acidic catalysis from

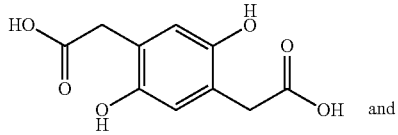

and

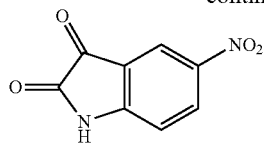

in a molar ratio of 1:2, of empirical formula $C_{26}H_{10}N_4O_{10}$, characterized by an X-ray powder diagram with lines at 6.6 s, 9.7 w, 13.3 w, 16.2 w, 19.9 w, 22.1 w, 24.9 w, 26.9 w and 29.1 w °2θ;

the reaction product, obtained by acidic catalysis from

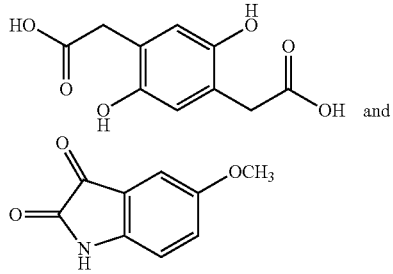

and in a molar ratio of 1:2, of empirical formula $C_{28}H_{16}N_2O_8$, characterized by an X-ray powder diagram with lines at 7.0 s, 10.1 m, 11.8 s, 20.5 m, 21.8 m, 24.2 m, 26.3 s and 27.9 m °2θ;

the reaction product, obtained by acidic catalysis from

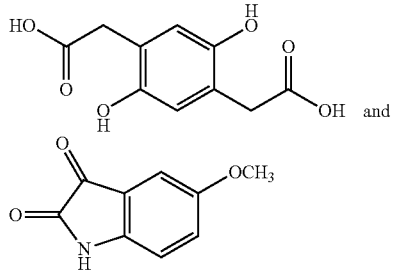

and in a molar ratio of 1:2, of empirical formula $C_{28}H_{16}N_2O_8$, characterized by an X-ray powder diagram with lines at 6.2 s, 13.3 m, 17.8 w, 22.8 w, 23.0 w, 25.0 w and 26.9 m °2θ;

the reaction product, obtained by acidic catalysis from

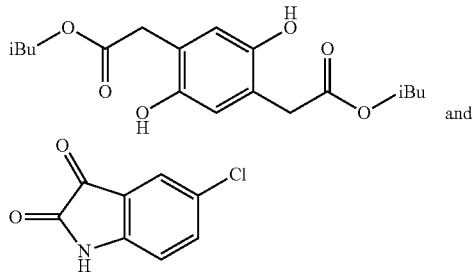

and in a molar ratio of 1:2, of empirical formula $C_{26}H_{10}N_2O_6Cl_2$, characterized by an X-ray powder diagram with lines at 7.1 m, 11.7 s, 19.2 w, 20.5 w, 22.6 m, 24.3 m, 25.6 w, 26.7 m, 27.1 m and 29.0 w °2θ;

the reaction product, obtained by acidic catalysis from

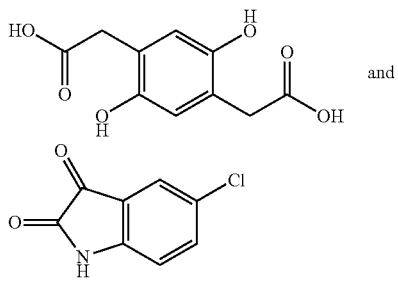

and in a molar ratio of 1:2, of empirical formula $C_{26}H_{10}N_2O_6Cl_2$, characterized by an X-ray powder diagram with lines at 4.8 m, 12.6 m, 21.8 w, 24.9 m and 27.4 s °2θ;

the reaction product, obtained by acidic catalysis from

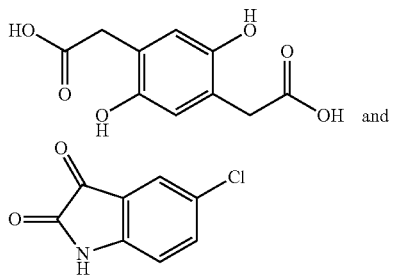

and in a molar ratio of 1:2, of empirical formula $C_{26}H_{10}N_2O_6Cl_2$, characterized by an X-ray powder diagram with lines at 4.7 s, 9.3 w, 14.5 w, 16.0 w, 19.7 w and 24.6 w °2θ;

the reaction product, obtained by acidic catalysis from

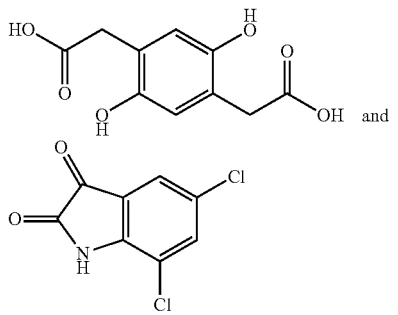

and in a molar ratio of 1:2, of empirical formula $C_{26}H_8N_2O_6Cl_4$, characterized by an X-ray powder diagram with lines at 5.9 w, 15.2 w, 23.9 w, 25.1 m and 26.8 s °2θ;

the reaction product, obtained by acidic catalysis from

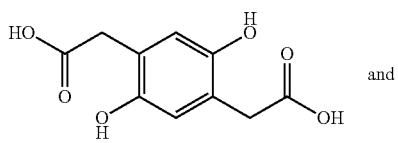

and

-continued

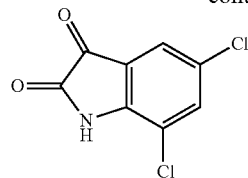

in a molar ratio of 1:2, of empirical formula $C_{26}H_8N_2O_6Cl_4$, characterized by an X-ray powder diagram with lines at 23.9 w and 26.9 s °2θ;

the reaction product, obtained by acidic catalysis from

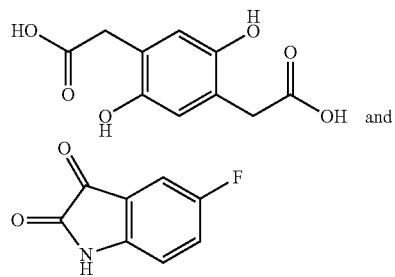

and in a molar ratio of 1:2, of empirical formula $C_{26}H_{10}N_2O_6F_2$, characterized by an X-ray powder diagram with lines at 6.7 s, 14.8 m, 16.1 m, 19.9 m, 21.8 m, 22.3 m, 24.8 m, 26.8 s and 29.1 m °2θ;

the reaction product, obtained by acidic catalysis from

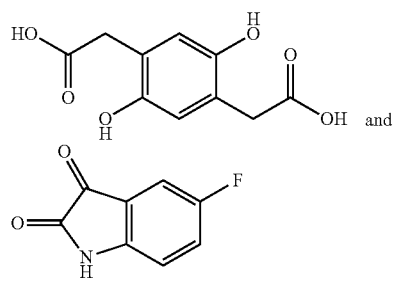

and in a molar ratio of 1:2, of empirical formula $C26H_{10}N_2O_6F_2$, characterized by an X-ray powder diagram with lines at 6.7 s, 9.7 w, 13.3 w, 14.9 w, 16.3 w, 20.0 w, 22.3 w, 25.0 w, 26.9 w and 29.2 w °2θ;

the reaction product, obtained by acidic catalysis from

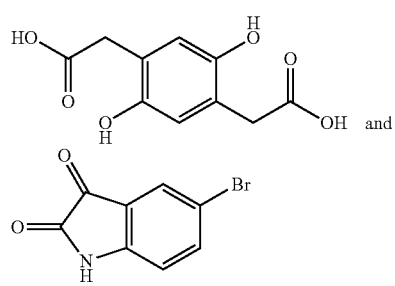

and in a molar ratio of 1:2, of empirical formula $C_{26}H_{10}N_2O_6Br_2$, characterized by an X-ray powder diagram with lines at 10.0 w, 11.6 m, 19.3 m, 20.6 w, 22.1 s, 23.3 w, 24.3 m, 25.4 m, 26.0 w, 26.8 w, 26.9 s, 28.8 w and 31.3 w °2θ;

the reaction product, obtained by acidic catalysis from

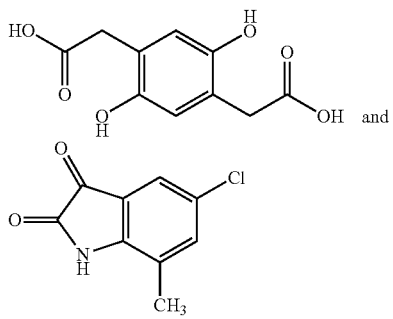

in a molar ratio of 1:2, of empirical formula $C_{28}H_{14}N_2O_6Cl_2$, characterized by an X-ray powder diagram with lines at 6.0 m, 7.0 m, 9.2 w, 11.1 s, 19.7 w, 20.6 m, 22.4 w, 25.0 m, 26.5 s and 28.3 w °2θ;

the reaction product, obtained by acidic catalysis from

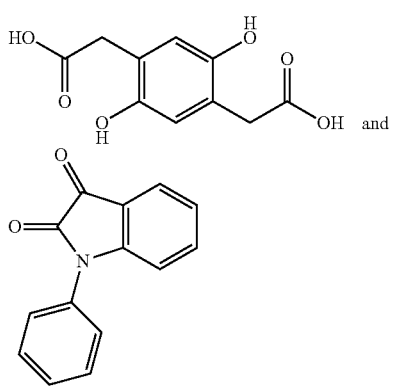

in a molar ratio of 1:2, of empirical formula $C_{38}H_{20}N_2O_6$, characterized by an X-ray powder diagram with lines at 6.7 s, 9.6 w, 10.7 w, 14.4 w, 15.2 w, 19.9 w, 21.6 w and 25.3 w °2θ;

the reaction product, obtained by acidic catalysis from

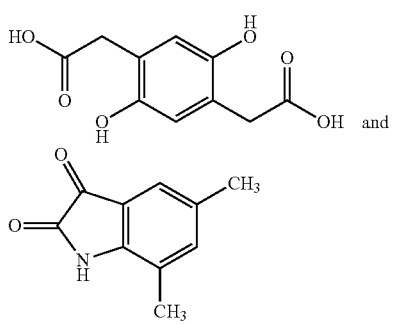

in a molar ratio of 1:2 in toluene with p-toluenesulphonic acid, followed by recrystallization from glacial acetic acid or N-methylpyrrolidone, of empirical formula $C_{30}H_{20}N_2O_6$, characterized by an X-ray powder diagram with lines at 6.9 s, 9.2 s, 11.1 s, 14.2 w, 20.3 w, 22.4 w and 26.3 m °2θ;

the reaction product, obtained by acidic catalysis from

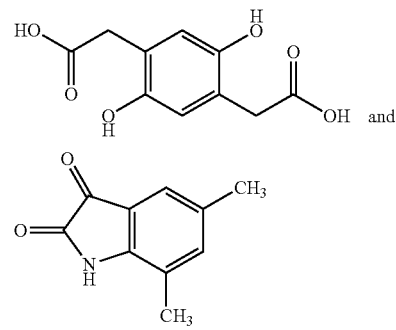

in a molar ratio of 1:2, of empirical formula $C_{30}H_{20}N_2O_6$, characterized by an X-ray powder diagram with lines at 6.9 s, 11.0 s, 20.3 w and 26.3 m °2θ;

the reaction product, obtained by acidic catalysis from

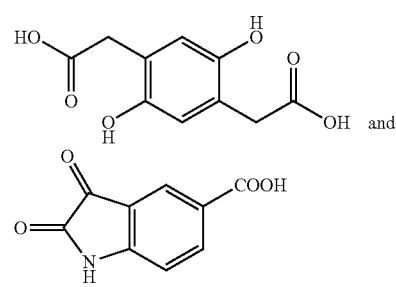

in a molar ratio of 1:2 with p-toluenesulphonic acid, of empirical formula $C_{30}H_{16}N_2O_{10}$, characterized by an X-ray powder diagram with lines at 10.6 s, 14.4 w, 16.7 w, 19.1 w, 23.7 w, 25.2 w, 26.6 w and 27.9 w °2θ;

the reaction product, obtained by acidic catalysis from

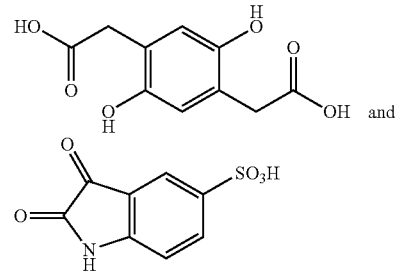

in a molar ratio of 1:2 with p-toluenesulphonic acid, of empirical formula $C_{28}H_{16}N_2O_{12}S_2$, characterized by an X-ray powder diagram with lines at 7.9 w, 9.7 w, 11.5 w, 12.6 s, 13.5 w, 15.9 w, 19.6 w, 21.4 m, 22.8 w, 23.5 w, 24.0 w, 25.4 m, 25.6 s, 27.9 w, 28.3 w, 29.1 w and 30.7 w °2θ; and the reaction product, obtained by acidic catalysis from

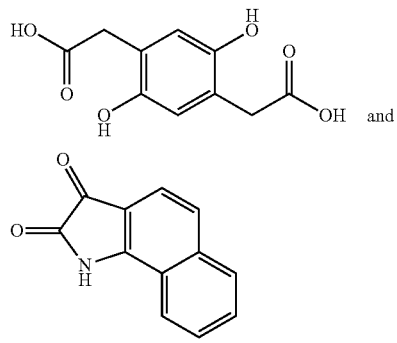

in a molar ratio of 1:2, of empirical formula $C_{34}H_{16}N_2O_6$, characterized by a mass spectrum with molecular ion m/z 548.1.

11. A black colorant obtained according to claim 3, selected from the group consisting of:

the reaction product obtained by acidic catalysis from

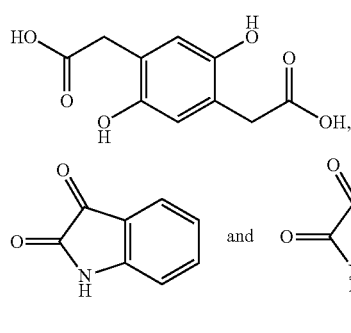

in a molar ratio of 1:1:1, comprising compounds of empirical formulae $C_{26}H_{12}N_2O_6$, $C_{28}H_{16}N_2O_6$ and $C_{30}H_{20}N_2O_6$, characterized by an X-ray powder diagram with lines at 7.6 s, 9.5 w, 11.8 s, 20.7 w, 24.7 m, 26.4 m and 28.4 m °2θ;

the reaction product obtained by acidic catalysis from

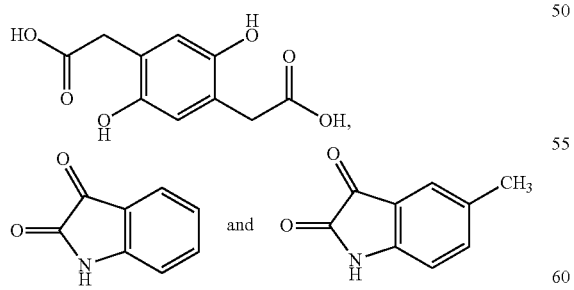

in a molar ratio of 1:1:1, comprising compounds of empirical formulae $C_{26}H_{12}N_2O_6$, $C_{27}H_{14}N_2O_6$ and $C_{28}H_{16}N_2O_6$, characterized by an X-ray powder diagram with lines at 7.4 s, 10.0 w, 11.9 s, 18.8 w, 20.1 w, 22.1 w, 24.1 m, 25.0 w, 26.6 m and 28.6 w °2θ;

the reaction product obtained by acidic catalysis from

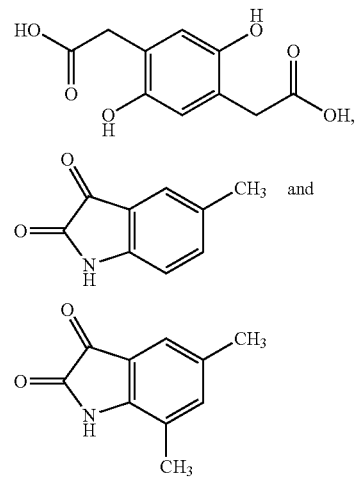

in a molar ratio of 1:1:1, comprising compounds of empirical formulae $C_{28}H_{16}N_2O_6$, $C_{29}H_{18}N_2O_6$ and $C_{30}H_{20}N_2O_6$, characterized by an X-ray powder diagram with lines at 7.2 s, 9.3 w, 11.3 s, 19.4 w, 20.6 w, 24.5 w, 26.4 m, 26.9 w and 28.3 w °2θ;

the reaction product obtained by acidic catalysis from

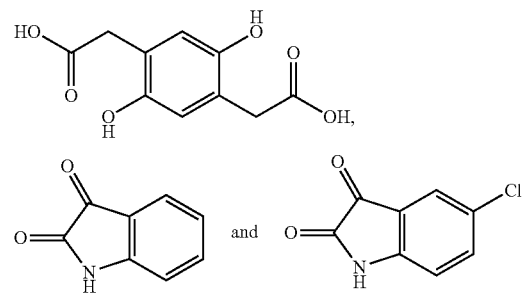

in a molar ratio of 1:1:1, comprising compounds of empirical formulae $C_{26}H_{12}N_2O_6$, $C_{26}H_{11}N_2O_6Cl$ and $C_{26}H_{10}N_2O_6Cl_2$, characterized by an X-ray powder diagram with lines at 7.2 s, 7.4 s, 10.3 w, 11.9 m, 12.2 s, 13.3 w, 18.9 w, 20.2 w, 22.8 m, 24.1 s, 25.3 w, 26.8 s and 29.0 m °2θ;

the reaction product obtained by acidic catalysis from

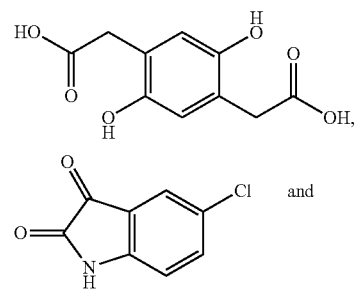

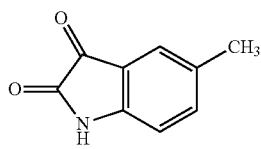

in a molar ratio of 1:1:1, comprising compounds of empirical formulae $C_{26}H_{10}N_2O_6Cl_2$, $C_{27}H_{13}N_2O_6Cl$ and $C_{28}H_{16}N_2O_6$, characterized by an X-ray powder diagram with lines at 7.1 s, 11.6 s, 19.2 w, 20.4 w, 21.9 w, 24.2 m, 25.2 w, 26.7 s and 28.7 w °2θ;

the reaction product obtained by acidic catalysis from

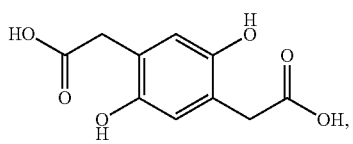

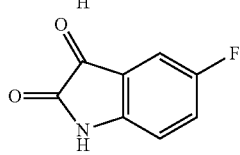

in a molar ratio of 1:1:1, comprising compounds of empirical formulae $C_{26}H_{12}N_2O_6$, $C_{26}H_{11}N_2O_6F$ and $C_{26}H_{10}N_2O_6F_2$, characterized by an X-ray powder diagram with lines at 6.6 s, 13.5 w, 14.7 m, 15.9 w, 19.8 m, 21.6 m, 22.3 w, 24.6 m, 26.6 s and 28.8 m °2θ;

the reaction product obtained by acidic catalysis from

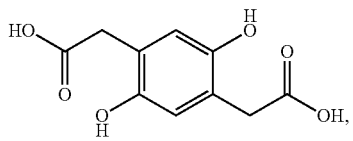

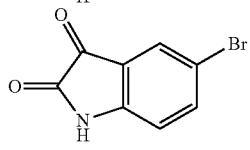

in a molar ratio of 1:1:1, comprising compounds of empirical formulae $C_{26}H_{12}N_2O_6$, $C_{26}H_{11}N_2O_6Br$ and $C_{26}H_{10}N_2O_6Br_2$, characterized by an X-ray powder diagram with lines at 7.1 m, 10.2 m, 11.8 s, 13.1 m, 18.8 m, 20.2 m, 22.7 s, 24.0 s, 25.3 m, 26.5 s, 26.8 s and 28.8 m °2θ;

the reaction product obtained by acidic catalysis from

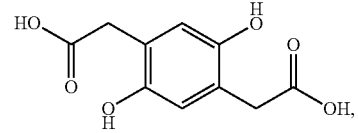

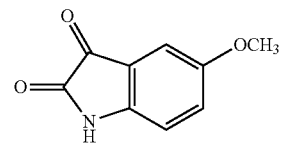

in a molar ratio of 1:1:1, comprising compounds of empirical formulae $C_{26}H_{12}N_2O_6$, $C_{27}H_{14}N_2O_7$ and $C_{28}H_{16}N_2O_8$, characterized by an X-ray powder diagram with lines at 7.0 s, 10.4 w, 11.6 m, 19.0 w, 20.3 w, 22.3 w, 24.0 w, 25.3 w, 26.5 m and 28.7 w °2θ;

the reaction product obtained by acidic catalysis from

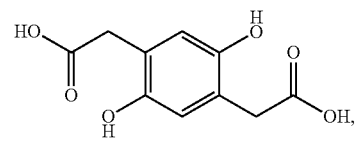

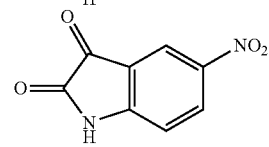

in a molar ratio of 1:1:1, comprising compounds of empirical formulae $C_{26}H_{10}N_2O_6Cl_2$, $C_{26}H_{10}N_3O_8Cl$ and $C_{26}H_{10}N_4O_{10}$, characterized by an X-ray powder diagram with lines at 6.1 m, 11.9 m, 13.5 w, 15.0 w, 16.5 w, 22.6 w, 24.1 w, 24.7 w and 26.9 s °2θ;

the reaction product obtained by acidic catalysis from

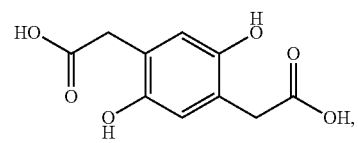

in a molar ratio of 1:1:1, comprising compounds of empirical formulae $C_{26}H_{10}N_2O_6Cl_2$, $C_{26}H_9N_2O_6Cl_3$ and $C_{26}H_8N_2O_6Cl_4$, characterized by an X-ray powder diagram with lines at 4.6 s, 9.3 w, 11.6 m, 14.2 w, 17.1 w, 18.8 w, 22.1 w, 25.4 m, 26.0 m and 27.5 s °2θ; and the reaction product obtained by acidic catalysis from in a molar ratio of 1:1:1, comprising compounds of empirical formulae $C_{26}H_{10}N_2O_6Cl_2$, $C_{27}H_{13}N_2O_7Cl$ and $C_{28}H_{16}N_2O_8$, characterized by an X-ray powder diagram with lines at 7.0 s, 11.2 s, 12.7 w, 19.4 w, 20.7 w, 21.6 w, 22.5 w, 24.3 w, 25.3 w, 26.8 m and 28.7 w °2θ.

12. A black colorant composition comprising the reaction products of a compound of the formula (i)

with a compound of the formula (iia)

and 1 to 4 further compounds of the formula (iib)

in an overall molar ratio (i):(ii) of 1:2 in the presence of a catalyst which in water at 25° C. has a pK≤4.5, the amount of the compound of the formula (iia) being from 85% to 99.9% by weight, based on the total amount of the compounds of the formulae (iia) and (iib), and $R_3$, $R_4$, $R_5$, $R_6$ and $R_7$ in the formulae (iia) and (iib) having, independently of one another, the same definition as in formula (ii) according to claim 1.

13. A method of utilizing a black colorant obtained according to claim 1 for coloring paints, printing inks and plastics in the mass.

14. A method of utilizing a black colorant according to claim 13, in which other crystal polymorphs are present in an amount of less than 20% by weight based on the total amount of all of the crystal polymorphs of the colorant.

15. A mass-coloured, high molecular weight material containing from 0.01% to 70% by weight, based on the total coloured high molecular weight material, of a black colorant obtained according to claim 1.

16. A mass-coloured, high molecular weight material containing from 0.01% to 70% by weight of a black colorant obtained according to claim 1 and from 0.01% to 20% by weight of a basic light stabilizer or of a mixture of basic light stabilizers, in each case based on the overall coloured high molecular weight material.

17. A mulch film, instrument panel, woven fabric, garden furniture item or element for the construction industry, comprising mass-coloured, high molecular weight material according to claim 15.

18. A process for preparing a colorant, in which a black colorant obtained according to claim 1 is sulphonated, chlorosulphonated, neutralized at carboxyl or sulpho groups, or amidated at $SO_2Cl$ groups.

19. A process according to claim 3, in which a compound of the formula (iv) is selected from the group consisting of compounds having the following substitution patterns:
$R_3=R_4=R_5=R_6=R_7=H$;
$R_3=R_5=R_6=R_7=H, R_4=NO_2$;
$R_3=R_5=R_6=R_7=H, R_4=OCH_3$;
$R_3=R_5=R_6=R_7=H, R_4=Cl$;
$R_3=R_5=R_6=R_7=H, R_4=F$;
$R_3=R_5=R_6=R_7=H, R_4=Br$;
$R_3=R_5=R_6=R_7=H, R_4=SO_3H$;
$R_3=R_5=R_6=R_7=H, R_4=COOH$;
$R_3=R_5=R_6=R_7=H, R_4=N(CH_3)_2$;
$R_3=R_5=R_6=R_7=H, R_4=NHCOC_1$-$C_{18}$alkyl;
$R_3=R_5=R_6=R_7=H, R_4=C_1$-$C_{20}$alkyl;
$R_3=R_5=R_6=R_7=H, R_4=C_2$-$C_{20}$alkoxy;
$R_3=R_5=R_7=H, R_4=R_6=CH_3$;
$R_3=R_5=R_7=H, R_4=R_6=Cl$;
$R_3=R_5=R_7=H, R_4=Cl, R_6=CH_3$;
$R_3=R_4=R_5=R_6=H, R_7=CH_3$;
$R_3=R_4=R_5=R_6=H, R_7=C_6H_5$; and
$R_3=R_4=R_7=H, R_5$ and $R_6$ together=1,4-butadienylene.

20. A process for preparing a colorant, in which a black colorant obtained according to claim 3 is sulphonated, chlorosulphonated, neutralized at carboxyl or sulpho groups, or amidated at $SO_2Cl$ groups.

* * * * *